(12) United States Patent
Rector et al.

(10) Patent No.: US 12,349,933 B2
(45) Date of Patent: Jul. 8, 2025

(54) TISSUE CUSHION ADJUNCT FOR SURGICAL STAPLER END EFFECTOR

(71) Applicant: Cilag GmbH International, Zug (CH)

(72) Inventors: Jason M. Rector, Maineville, OH (US); Mark S. Zeiner, Mason, OH (US)

(73) Assignee: Cilag GmbH International, Zug (CH)

(*) Notice: Subject to any disclaimer, the term of this patent is extended or adjusted under 35 U.S.C. 154(b) by 246 days.

(21) Appl. No.: 17/704,079

(22) Filed: Mar. 25, 2022

(65) Prior Publication Data

US 2023/0301674 A1    Sep. 28, 2023

(51) Int. Cl.
*A61B 17/29* (2006.01)
*A61B 17/00* (2006.01)
(Continued)

(52) U.S. Cl.
CPC ........ *A61B 17/29* (2013.01); *A61B 17/00234* (2013.01); *A61B 17/0684* (2013.01);
(Continued)

(58) Field of Classification Search
CPC ............ A61B 17/072; A61B 17/07292; A61B 2017/07214; A61B 2017/07242; A61B 2017/07271
(Continued)

(56) References Cited

U.S. PATENT DOCUMENTS

| 5,810,855 A | 9/1998 | Rayburn et al. |
| 7,380,696 B2 | 6/2008 | Shelton, IV et al. |

(Continued)

FOREIGN PATENT DOCUMENTS

| EP | 2090248 A2 | 8/2009 |
| EP | 3150134 A1 | 4/2017 |

(Continued)

OTHER PUBLICATIONS

Steel wool scrubber, by EleQit Store, first available for sale on Jul. 20, 2020. URL https://www.amazon.com/EleQit-Stainless-Scrubber-Stovetops-Kitchenware/dp/B08DBYG6YM (Year: 2020).*

(Continued)

*Primary Examiner* — Nathaniel C Chukwurah
(74) *Attorney, Agent, or Firm* — Frost Brown Todd LLC

(57) ABSTRACT

An adjunct configured for use with an end effector of a surgical stapler includes a plurality of resiliently compressible elements interconnected with each other. The adjunct also includes a tissue-engaging face configured to contact tissue clamped by the end effector during closure thereof, and a stapler-engaging face configured to be releasably secured to a stapling surface of the end effector. Each resiliently compressible element of the plurality of resiliently compressible elements includes a hollow interior and an open end at one of the tissue-engaging or stapler-engaging faces. The hollow interior expands outwardly toward the open end. Each resiliently compressible element of the plurality of resiliently compressible elements is configured to be captured and compressed by a corresponding staple ejected from the end effector into the clamped tissue and thereby reinforce the engagement between the ejected staples and the clamped tissue.

20 Claims, 26 Drawing Sheets

(51) Int. Cl.
*A61B 17/068* (2006.01)
*A61B 17/072* (2006.01)

(52) U.S. Cl.
CPC .. *A61B 17/072* (2013.01); *A61B 2017/07214* (2013.01); *A61B 2017/07242* (2013.01); *A61B 2017/2927* (2013.01)

(58) Field of Classification Search
USPC ...................................................... 227/175.1
See application file for complete search history.

(56) References Cited

U.S. PATENT DOCUMENTS

| | | | |
|---|---|---|---|
| 7,845,533 | B2 | 12/2010 | Marczyk et al. |
| 8,034,396 | B2 | 10/2011 | Kapiamba et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 9,186,142 | B2 | 11/2015 | Fanelli et al. |
| 9,271,706 | B2 | 3/2016 | Stopek et al. |
| 9,364,233 | B2 | 6/2016 | Alexander, III et al. |
| 9,517,065 | B2 | 12/2016 | Simms et al. |
| 9,622,746 | B2 | 4/2017 | Simms et al. |
| 9,649,110 | B2 | 5/2017 | Parihar et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,907,554 | B2 | 3/2018 | Morgan et al. |
| 10,092,292 | B2 | 10/2018 | Boudreaux et al. |
| 10,166,023 | B2 | 1/2019 | Vendely et al. |
| 10,349,939 | B2 | 7/2019 | Shelton, IV et al. |
| 10,426,481 | B2 | 10/2019 | Aronhalt et al. |
| 10,441,285 | B2 | 10/2019 | Shelton, IV et al. |
| 10,524,788 | B2 | 1/2020 | Vendely et al. |
| 10,568,621 | B2 | 2/2020 | Shelton, IV et al. |
| 10,588,623 | B2 | 3/2020 | Schmid et al. |
| 10,624,861 | B2 | 4/2020 | Widenhouse et al. |
| 10,639,039 | B2 | 5/2020 | Vendely et al. |
| 10,667,808 | B2 | 6/2020 | Baxter, III et al. |
| 10,758,398 | B2 | 9/2020 | Murthy Aravalli et al. |
| 10,945,731 | B2 | 3/2021 | Baxter, III et al. |
| 10,966,722 | B2 | 4/2021 | Shelton, IV et al. |
| 10,987,107 | B2 | 4/2021 | Sgroi, Jr. et al. |
| 11,058,425 | B2 | 7/2021 | Widenhouse et al. |
| 11,382,625 | B2 | 7/2022 | Huitema et al. |
| 11,660,093 | B2 | 5/2023 | Bakos et al. |
| 11,857,190 | B2 | 1/2024 | Strang et al. |
| 2002/0165563 | A1 | 11/2002 | Grant et al. |
| 2005/0263562 | A1 | 12/2005 | Shelton, IV et al. |
| 2009/0020584 | A1 | 1/2009 | Soltz et al. |
| 2009/0206143 | A1* | 8/2009 | Huitema .......... A61B 17/07292 227/176.1 |
| 2010/0331880 | A1 | 12/2010 | Stopek et al. |
| 2011/0077629 | A1 | 3/2011 | Tanaka et al. |
| 2012/0080336 | A1 | 4/2012 | Shelton, IV et al. |
| 2012/0080498 | A1 | 4/2012 | Shelton, IV et al. |
| 2012/0080503 | A1 | 4/2012 | Woodard, Jr. et al. |
| 2012/0083836 | A1 | 4/2012 | Shelton, IV et al. |
| 2012/0125792 | A1 | 5/2012 | Cassivi |
| 2012/0136345 | A1 | 5/2012 | Takashino |
| 2012/0241492 | A1 | 9/2012 | Shelton, IV et al. |
| 2012/0241503 | A1 | 9/2012 | Baxter, III et al. |
| 2012/0241505 | A1* | 9/2012 | Alexander, III ... A61B 17/1155 227/179.1 |
| 2013/0146641 | A1 | 6/2013 | Shelton, IV et al. |
| 2013/0146643 | A1* | 6/2013 | Schmid ................ A61B 17/072 227/176.1 |
| 2013/0153635 | A1 | 6/2013 | Hodgkinson |
| 2013/0214030 | A1 | 8/2013 | Aronhalt et al. |
| 2013/0221062 | A1 | 8/2013 | Hodgkinson |
| 2013/0256376 | A1 | 10/2013 | Barton et al. |
| 2014/0131419 | A1 | 5/2014 | Bettuchi |
| 2014/0158741 | A1 | 6/2014 | Woodard, Jr. et al. |
| 2014/0166721 | A1 | 6/2014 | Stevenson et al. |
| 2014/0209658 | A1 | 7/2014 | Skalla et al. |
| 2014/0224686 | A1 | 8/2014 | Aronhalt et al. |
| 2014/0291382 | A1 | 10/2014 | Lloyd et al. |
| 2015/0136831 | A1* | 5/2015 | Baxter, III .......... A61B 17/105 227/176.1 |
| 2015/0196296 | A1 | 7/2015 | Swayze et al. |
| 2015/0196348 | A1 | 7/2015 | Yates et al. |
| 2015/0282809 | A1* | 10/2015 | Shelton, IV ......... A61B 17/068 227/176.1 |
| 2016/0278764 | A1 | 9/2016 | Shelton, IV et al. |
| 2016/0278765 | A1 | 9/2016 | Shelton, IV et al. |
| 2016/0278774 | A1 | 9/2016 | Shelton, IV et al. |
| 2017/0055981 | A1 | 3/2017 | Vendely et al. |
| 2017/0055986 | A1 | 3/2017 | Harris et al. |
| 2017/0086832 | A1* | 3/2017 | Harris ..................... B32B 3/266 |
| 2017/0086837 | A1* | 3/2017 | Vendely ................. B32B 5/024 |
| 2017/0086838 | A1 | 3/2017 | Harris et al. |
| 2017/0086841 | A1 | 3/2017 | Vendely et al. |
| 2017/0086845 | A1 | 3/2017 | Vendely et al. |
| 2017/0119379 | A1* | 5/2017 | Shelton, IV .......... A61L 24/046 |
| 2017/0119390 | A1 | 5/2017 | Schellin et al. |
| 2017/0119392 | A1 | 5/2017 | Shelton, IV et al. |
| 2018/0103952 | A1 | 4/2018 | Aronhalt et al. |
| 2018/0235624 | A1 | 8/2018 | Shelton, IV et al. |
| 2018/0235626 | A1* | 8/2018 | Shelton, IV ..... A61B 17/07292 |
| 2019/0008518 | A1 | 1/2019 | Sgroi, Jr. et al. |
| 2019/0200978 | A1 | 7/2019 | Shelton, IV et al. |
| 2019/0269402 | A1 | 9/2019 | Murray et al. |
| 2019/0298338 | A1 | 10/2019 | Vendely et al. |
| 2019/0314016 | A1 | 10/2019 | Huitema et al. |
| 2019/0314018 | A1 | 10/2019 | Huitema et al. |
| 2020/0205825 | A1 | 7/2020 | Vendely et al. |
| 2020/0305963 | A1 | 10/2020 | Wagner et al. |
| 2020/0390944 | A1 | 12/2020 | Williams et al. |
| 2021/0077095 | A1* | 3/2021 | Harris .............. A61B 17/07292 |
| 2021/0128129 | A1 | 5/2021 | George et al. |
| 2022/0061843 | A1 | 3/2022 | Vendely et al. |
| 2022/0160360 | A1 | 5/2022 | Harris et al. |
| 2022/0313247 | A1 | 10/2022 | Shelton, IV et al. |
| 2023/0301656 | A1* | 9/2023 | Seow .................. A61B 17/0686 |
| 2023/0301657 | A1* | 9/2023 | Zeiner .............. A61B 17/07207 |
| 2023/0301674 | A1* | 9/2023 | Rector ............. A61B 17/00234 |
| 2023/0301675 | A1* | 9/2023 | Seow ............... A61B 17/07207 |
| 2023/0320742 | A1* | 10/2023 | Bakos .............. A61B 17/07207 227/175.1 |

FOREIGN PATENT DOCUMENTS

| | | |
|---|---|---|
| EP | 3150142 A2 | 4/2017 |
| EP | 3162384 A1 | 5/2017 |
| EP | 3363387 A1 | 8/2018 |
| EP | 3424441 A2 | 1/2019 |
| EP | 3530213 A2 | 8/2019 |
| EP | 3791802 A1 | 3/2021 |
| EP | 3791805 A1 | 3/2021 |
| EP | 3791806 A1 | 3/2021 |

OTHER PUBLICATIONS

Flank, definition by Merriam-Webster, URL https://www.merriam-webster.com/dictionary/flank (Year: 2024).*
Include, definition by Merriam-Webster, URL https://www.merriam-webster.com/dictionary/INCLUDE (Year: 2024).*
Overlie, definition by Merriam-Webster, URL https://www.merriam-webster.com/dictionary/OVERLIE (Year: 2024).*
International Search Report and Written Opinion dated Aug. 2, 2023, for International Application No. PCT/IB2023/052793, 20 pages.
International Search Report and Written Opinion dated Jul. 31, 2023, for International Application No. PCT/IB2023/052804, 21 pages.
International Search Report and Written Opinion dated Aug. 7, 2023, for International Application No. PCT/IB2023/052805, 21 pages.

(56) References Cited

OTHER PUBLICATIONS

International Search Report and Written Opinion dated Aug. 9, 2023, for International Application No. PCT/IB2023/052809, 20 pages.
International Search Report and Written Opinion dated Jun. 20, 2023, for International Application No. PCT/IB2023/052810, 16 pages.

* cited by examiner

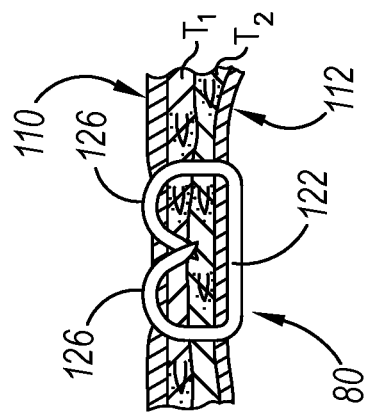
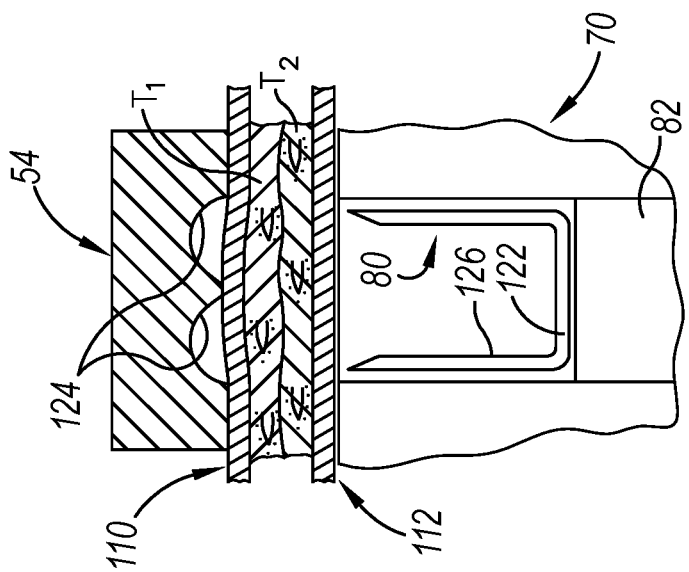
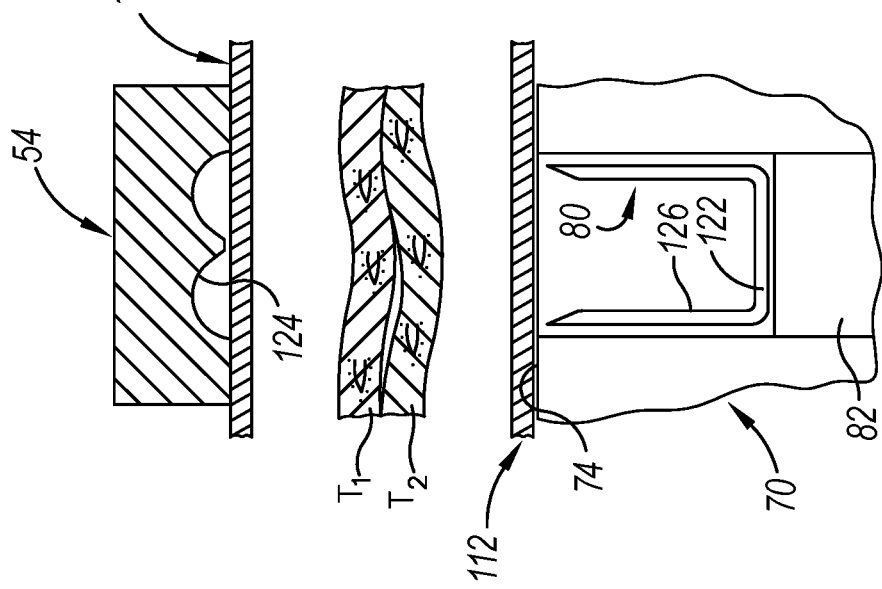
FIG. 8C
FIG. 8B
FIG. 8A

TISSUE CUSHION ADJUNCT FOR SURGICAL STAPLER END EFFECTOR

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patenttent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws;

FIG. 8B depicts a cross-sectional end view of the end effector and buttress assemblies of FIG. 8A, showing the end effector jaws in a closed state on the tissue;

FIG. 8C depicts a cross-sectional view of a formed staple and the buttress assemblies of FIG. 8A after having been secured to the tissue by the end effector of FIG. 3;

Figure 1:
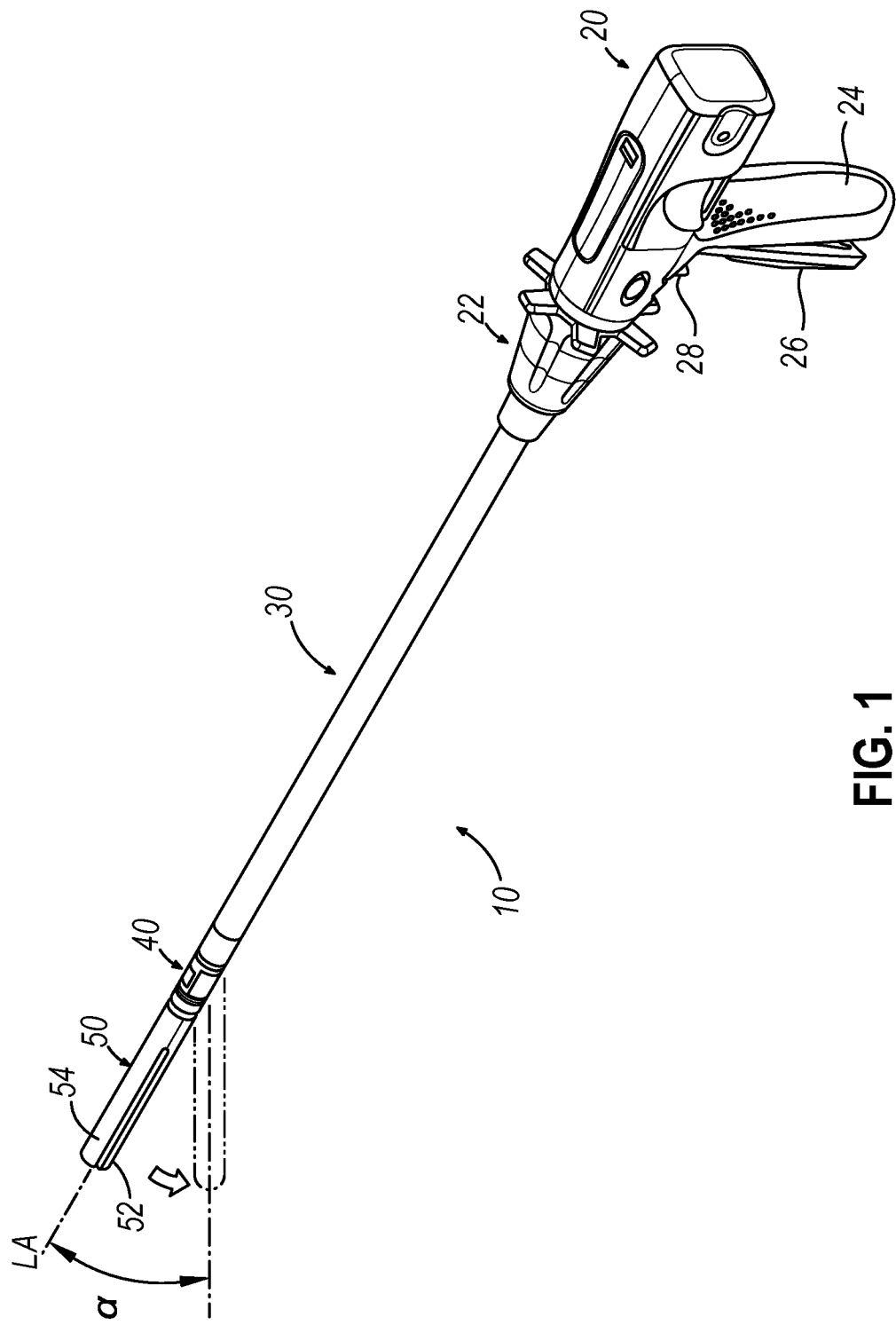
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

Figure 2:
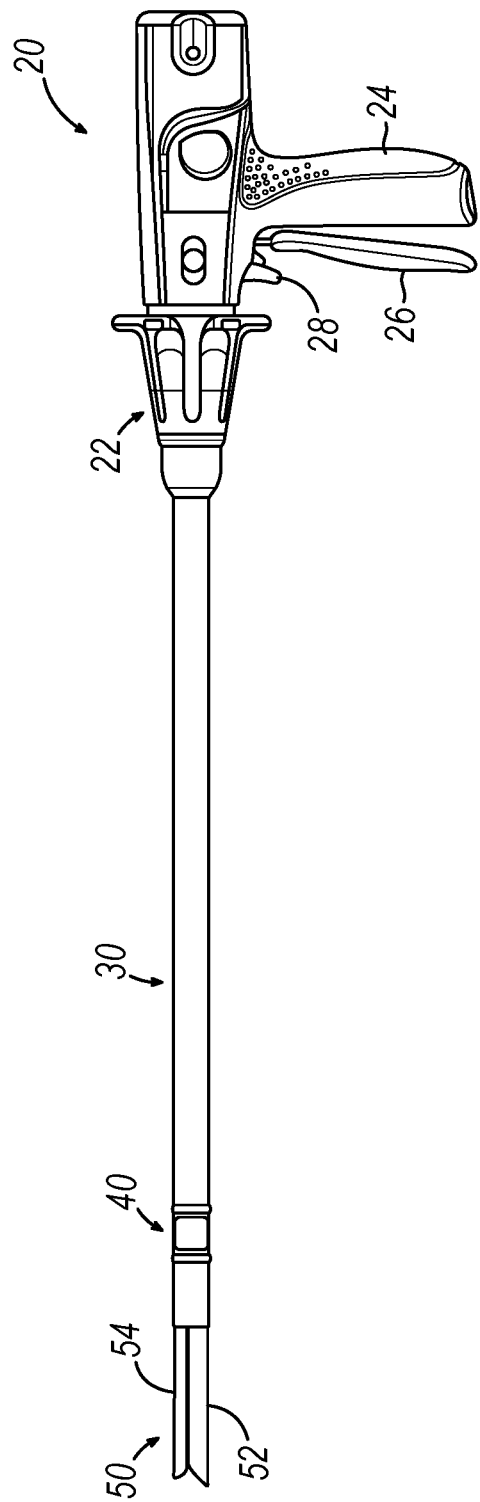
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (α) via actuation of an articulation control feature (22) of handle assembly (20).

Figure 3:
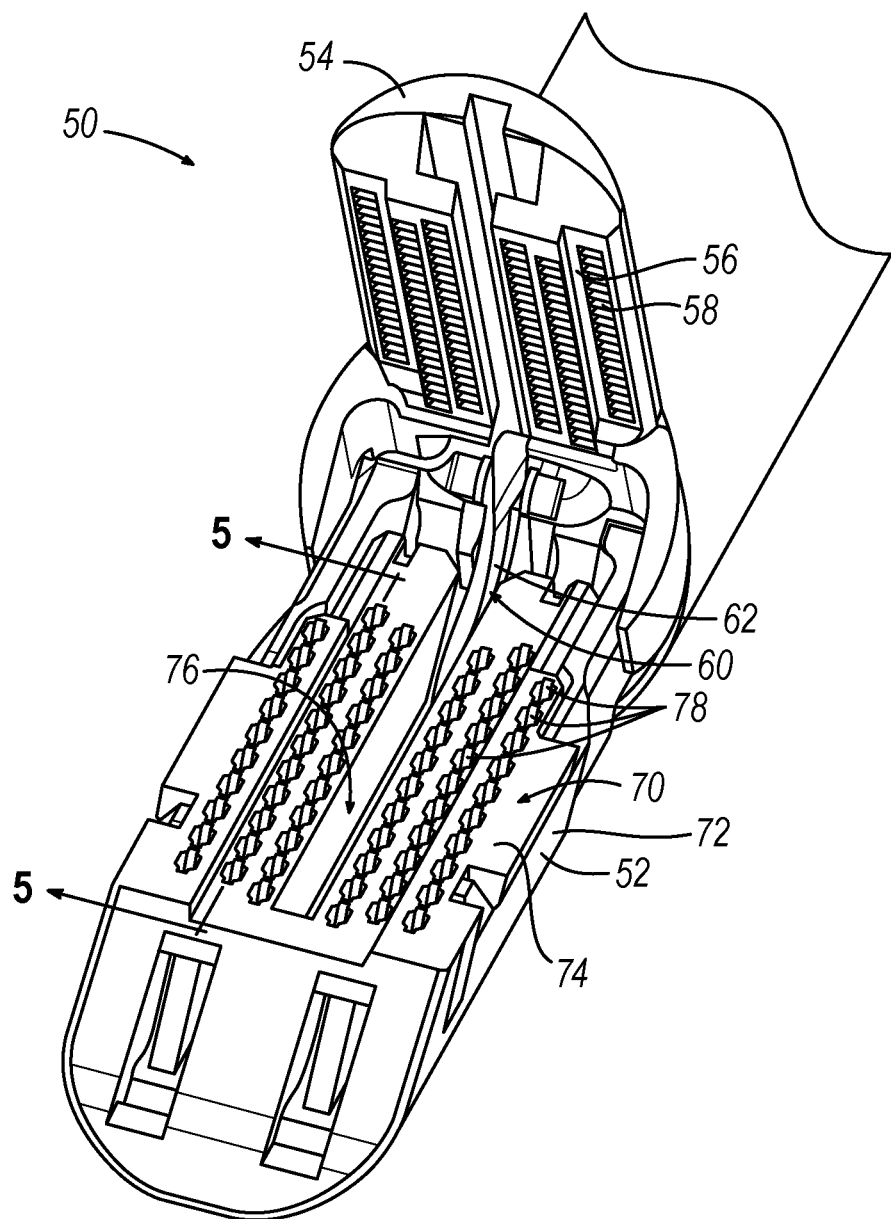
FIG. 3 depicts a perspective view of an end effector of the surgical stapler of FIG. 1 in an open state.
Figure 4:
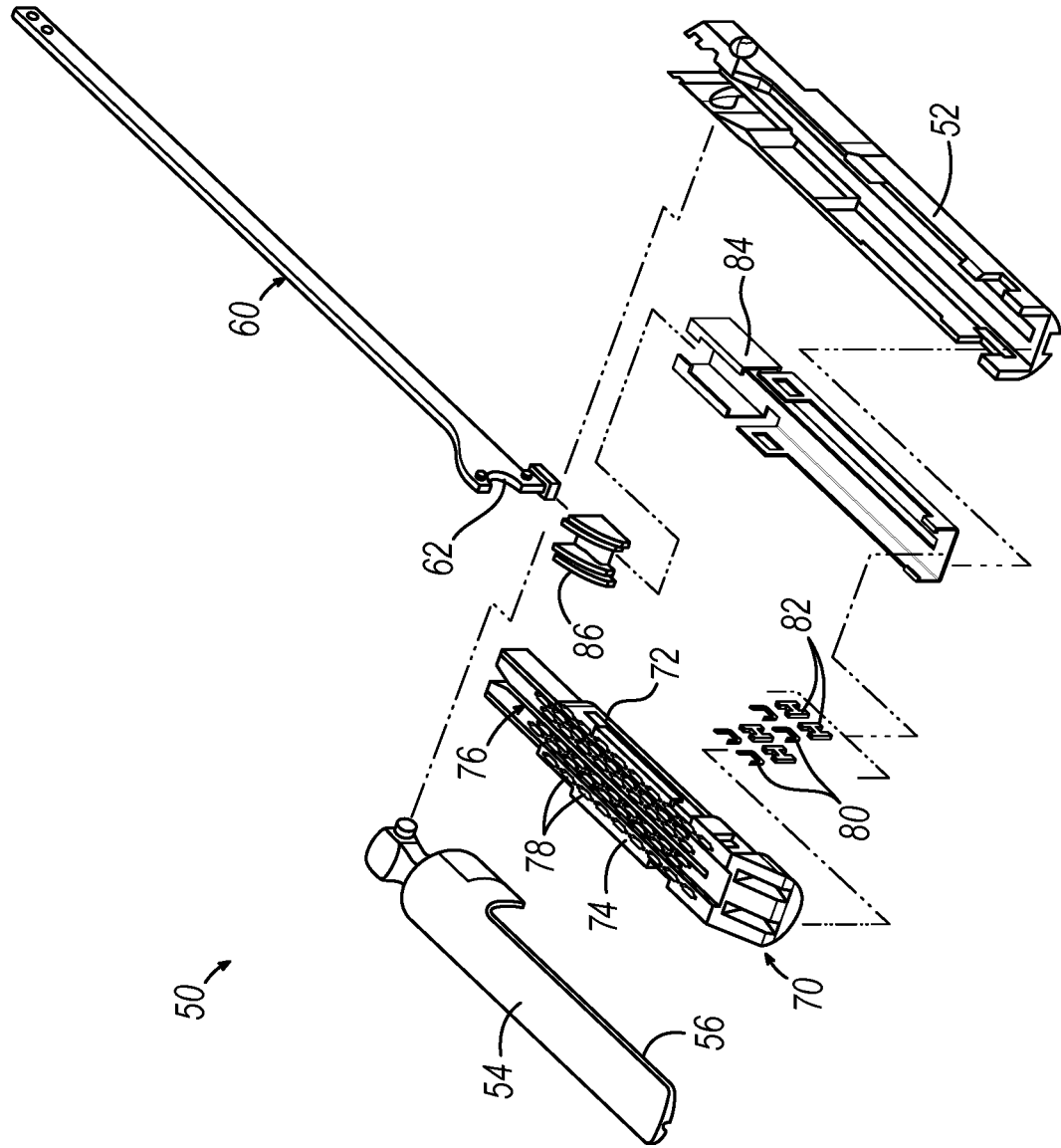
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (52) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
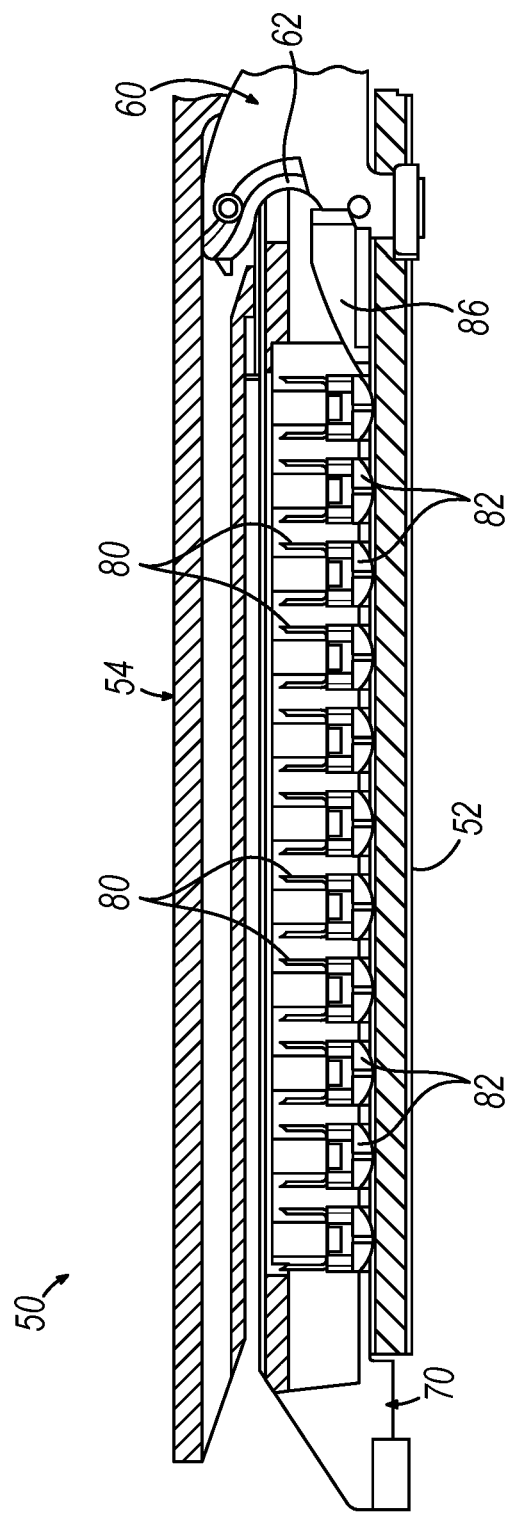
FIG. 5A depicts a side cross-sectional view of the end effector of FIG. 3, taken along line 5-5 of FIG. 3, with a firing member in a proximal position.
Figure 5B:
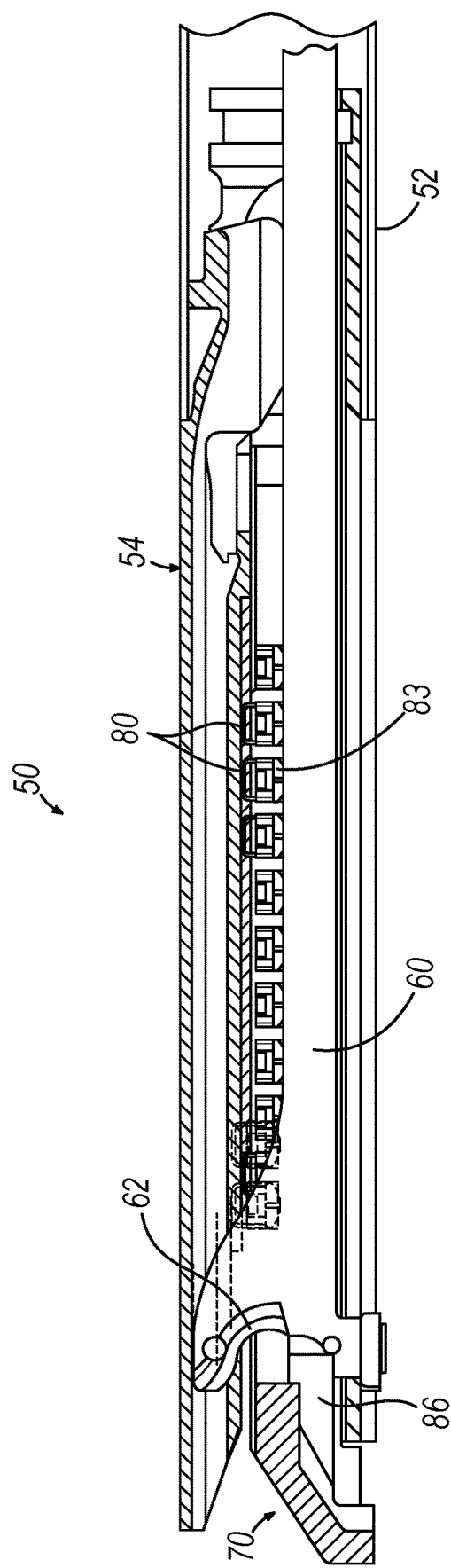
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
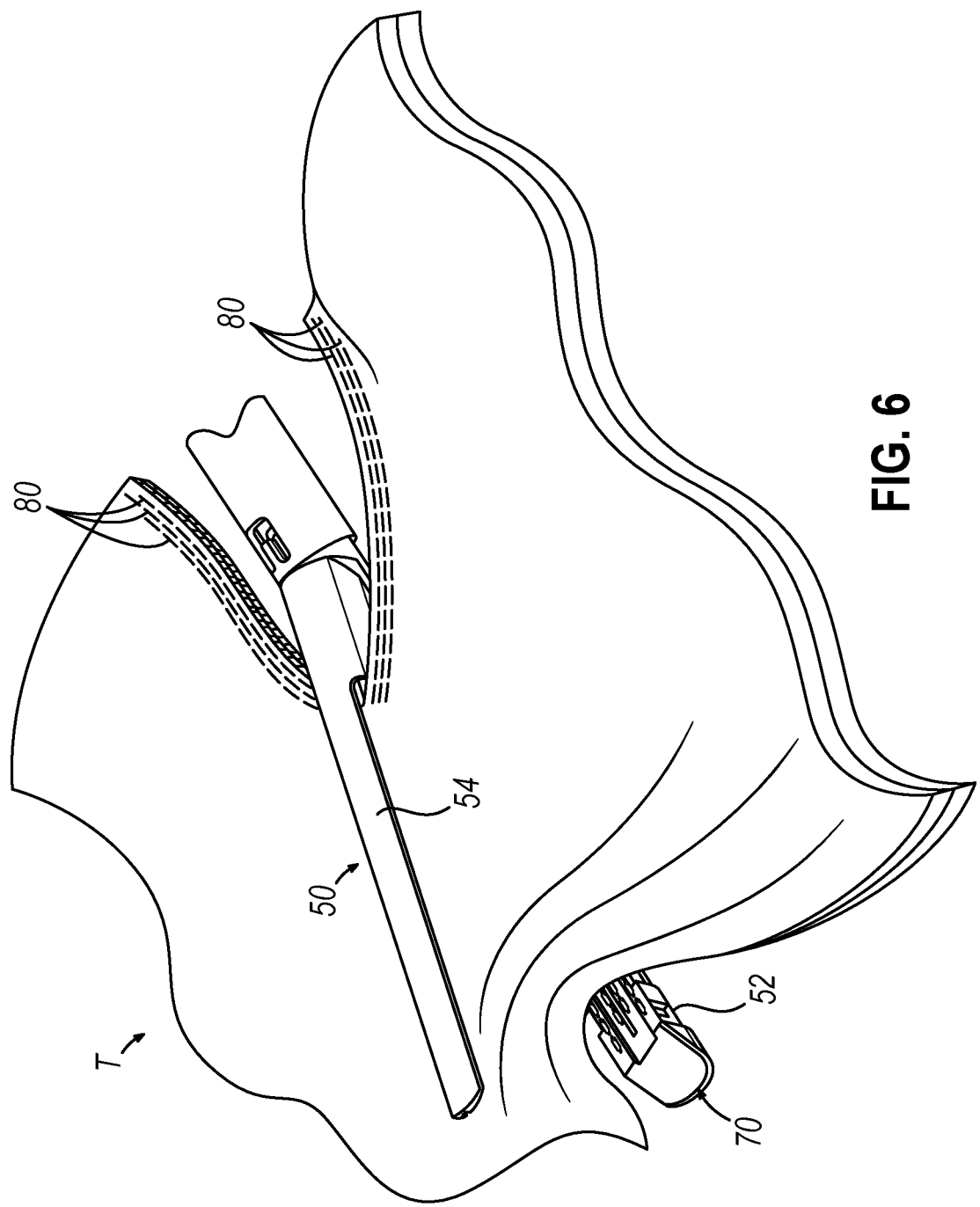
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
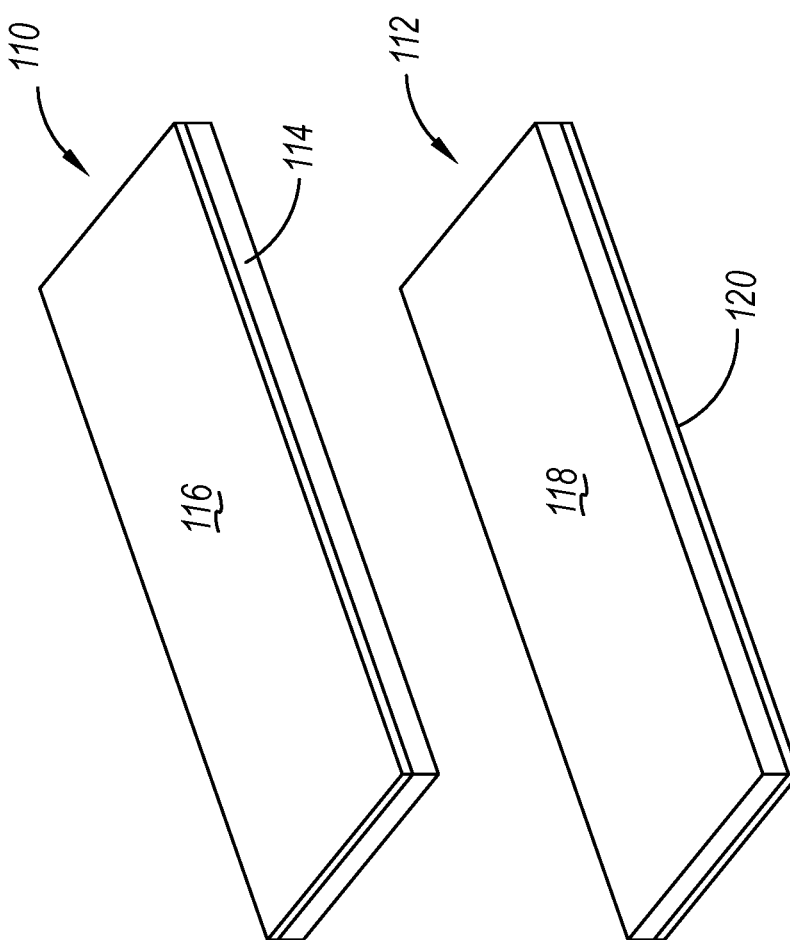
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
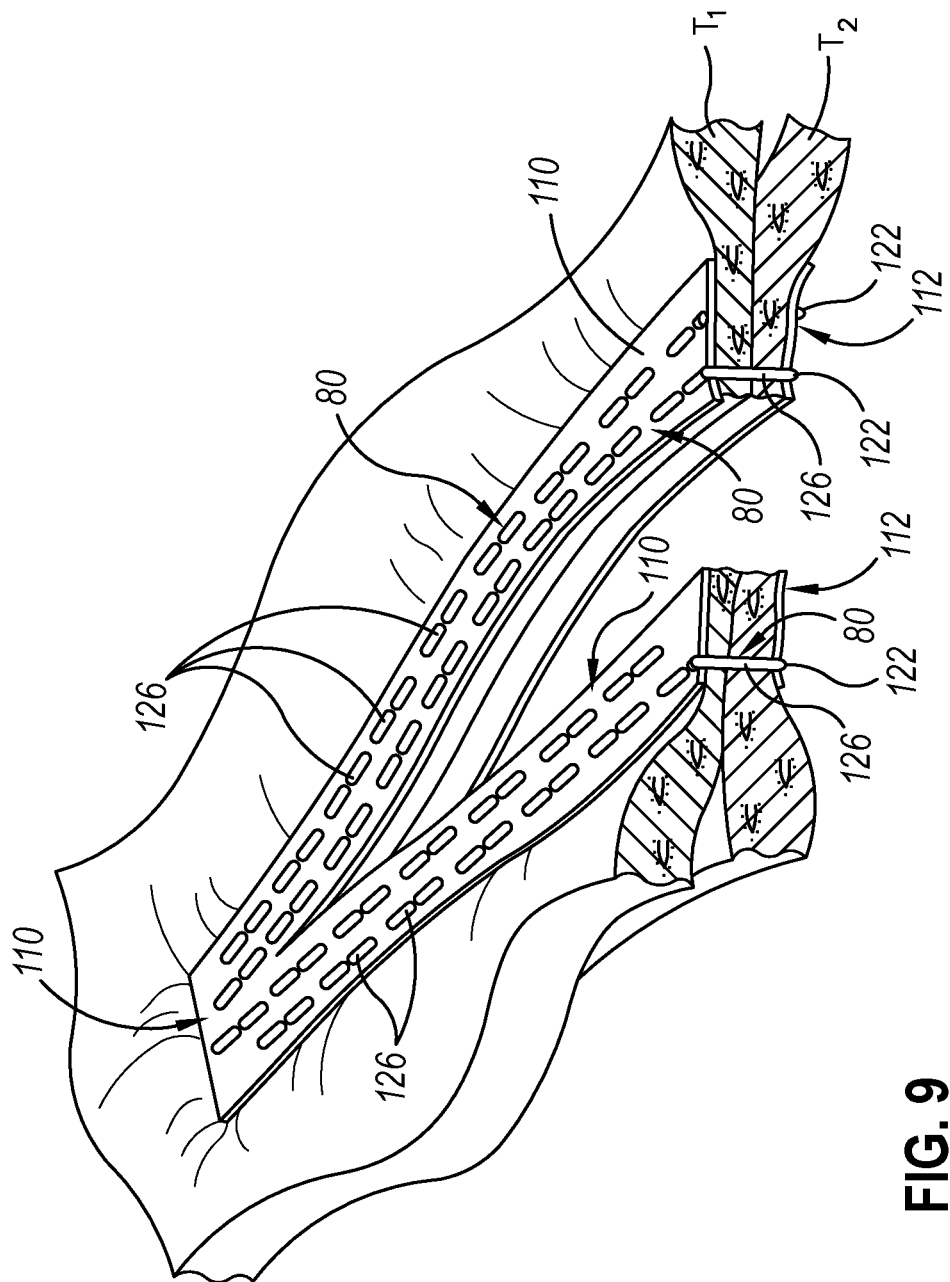
FIG. 9 depicts a perspective view of formed staples and the buttress assemblies of FIG. 8A after having been secured to the tissue by the end effector of FIG. 3.
Figure 10:
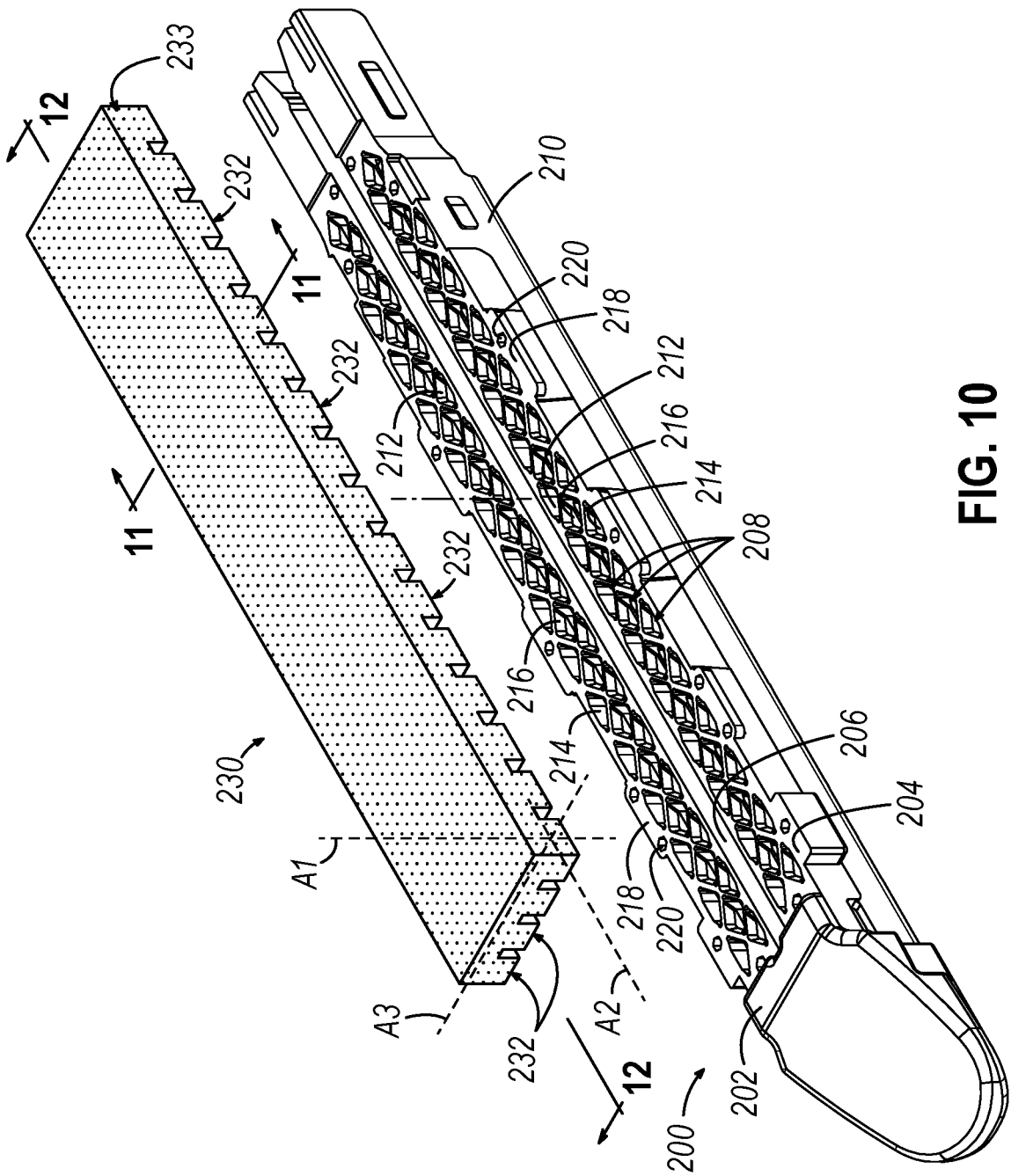
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,660,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Compressible Adjunct

Figure 11:
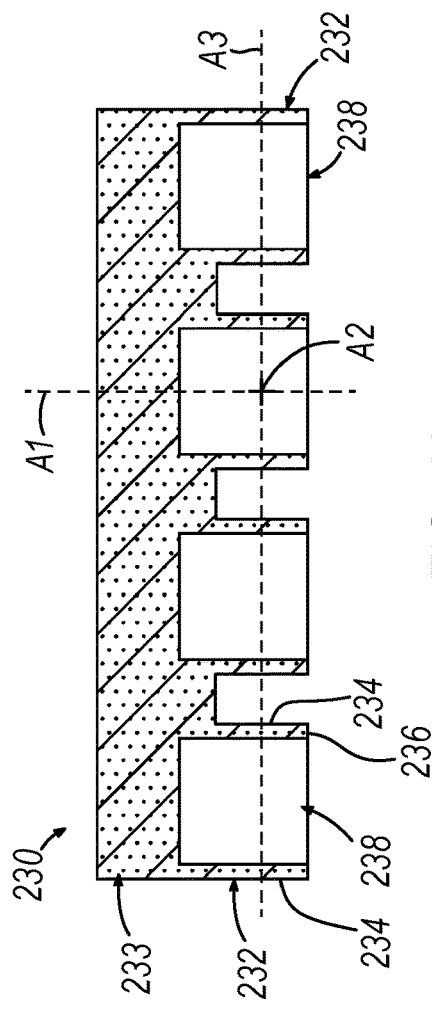
FIG. 11 depicts a cross-sectional view of the adjunct of FIG. 10, taken along line 11-11 of FIG. 10.
Figure 12:
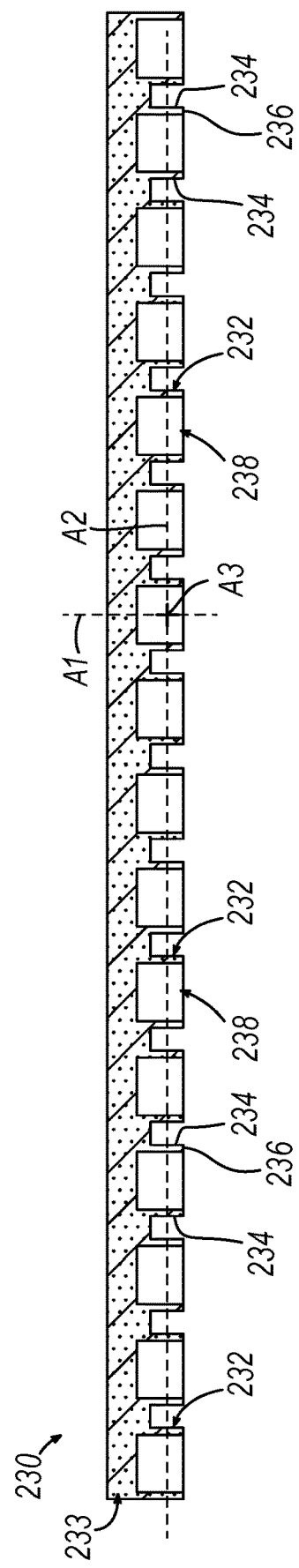
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape.

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid.

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3).

IV. Exemplary Compressible Adjuncts Having Improved Manufacturability

In some instances, it may be desirable to provide an adjunct with one or more features for improving the manufacturability of the adjunct. For example, it may be desirable to provide an adjunct with one or more features for promoting the ability of the adjunct to be manufactured using traditional manufacturing techniques, such as techniques utilized prior to the advent of additive manufacturing (also referred to as 3D-printing). Such techniques may include injection molding, thermoforming, vacuum forming, extruding, drawing, and/or laminating, for example. Exemplary versions of such features are described in greater detail below. Unless otherwise described, it will be appreciated that such features may be applied to a multi-layer adjunct similar to buttress assemblies (110, 112) described above in connection with FIGS. 7-9, or alternatively to a compressible monolithic adjunct similar to adjunct (230) described above in connection with FIGS. 10-12.

A. Exemplary Injection-Moldable Adjunct with Nodules Configured to be Flanked by Staple Legs FIGS. 13-16 show another exemplary compressible unitary (e.g., monolithic) adjunct (330) configured for releasable attachment to a staple cartridge (300). Staple cartridge (300) and adjunct (330) are configured for use with end effector (50) and are similar to staple cartridge (200) and adjunct (230) described above except as otherwise described below. In this regard, staple cartridge (300) includes a cartridge body (302) having an upwardly facing deck (304), an elongate slot (306) extending along a central axis of cartridge body (302) and opening upwardly through deck (304), and a plurality of staple openings (308) extending through deck (304) on each side of elongate slot (306). Each staple opening (308) slidably houses an unformed staple (80) (FIG. 16), and a respective staple driver (not shown), similar to staple driver (82), configured to drive the corresponding staple (80) outwardly toward anvil (56) to be formed. A lower tray (not shown) of staple cartridge (300) retains staples (80) and the staple drivers within cartridge body (302). Cartridge body (302) of the present example further includes a plurality of upwardly-opening recesses (312, 314, 316) formed in deck (304) and having base surfaces through which staple openings (308) extend. More specifically, on each side of elongate slot (306), deck (304) includes an inner row of triangular recesses (312) each having a medial apex that points transversely away from elongate slot (306); an outer row of triangular recesses (314) each having a medial apex that points transversely toward elongate slot (306); and a middle row of diamond-shaped recesses (316) each having an inner medial apex that points transversely toward elongate slot (306) and an opposed outer medial apex that points transversely away from elongate slot (306).

Adjunct (330) has a plurality of three-dimensional, resiliently compressible nodules (332) that are integrally connected with one another in a plurality of linear arrays defining a lattice structure having an elongate rectangular shape. In the present example, adjunct (330) includes two lateral adjunct sections (330a, 330b) configured for placement on respective sides of staple cartridge slot (306), each including inner and outer axial rows of nodules (332) each extending in a proximal-distal direction, and nine transverse rows of nodules (332) each extending in a direction transverse to a length of staple cartridge (300). In the example shown, each lateral adjunct section (330a, 330b) also includes a medial axial row of nodules (332) extending in the proximal-distal direction and offset from each of the inner and outer axial rows of nodules (332) in the proximal-distal direction. Additionally, adjunct (330) of the present example has a height of only one nodule (332). It will be appreciated that adjunct (330) of other versions may have various other quantities and configurations of nodules (332). In some versions, lateral adjunct sections (330a, 330b) may be coupled to each other by one or more webs (not shown) extending therebetween. For example, a plurality of such webs may be disposed at discrete locations along a length of adjunct (330). In any event, such web(s) may be configured to be severed by cutting edge (62) of firing member (60) during translation thereof through staple cartridge slot (306) to separate lateral adjunct sections (330a, 330b) from each other.

Each compressible nodule (332) of adjunct (330) is symmetrical about a pair of planes (not shown) that extend through a centroid of nodule (332), including: a first vertical plane that extends parallel to the sidewalls of staple cartridge slot (306); and a second vertical plane that extends transversely to the length of staple cartridge slot (306). Each nodule (332) of the present example has a hollow interior and includes a generally truncated cuboid central body (334) and five tapered trunks (336a, 336b, 336c, 336d, 336e) projecting outwardly from central body (334) to define the symmetrical geometrical configuration described above. More specifically, each nodule (332) includes a lower trunk (336a) extending along a vertical first axis (A1); a proximal, laterally-inner trunk (336b) and a distal, laterally-outer trunk (336c) aligned coaxially along a horizontal second axis (A2), which extends obliquely relative to the length of staple cartridge slot (306); and a proximal, laterally-outer trunk (336d) and a distal, laterally-inner trunk (336e) aligned coaxially along a horizontal third axis (A3), which also extends obliquely relative to the length of staple cartridge slot (306), where each axis (A1, A2, A3) extends through the centroid. Each trunk (336a, 336b, 336c, 336d, 336e) tapers in a direction away from central body (334). Each lower trunk (336a) has a generally O-shaped cross-section, while each proximal and distal laterally-inner and laterally-outer trunk (336b, 336c, 336d, 336e) has a generally U-shaped cross-section, as described in greater detail below. In some versions, the ratio of the overall height of adjunct (330) to the wall thickness(es) of each nodule (332) may be between about 4:1 and about 8:1.

As shown, each inner and outer nodule (332) is interconnected with one or two laterally-adjacent medial nodule(s) (332), via trunks (336b, 336c, 336d, 336e). Each medial nodule (332) is interconnected with one or two laterally-adjacent inner nodule(s) (332) and with one or two laterally-adjacent outer nodule(s) (332), via trunks (336b, 336c, 336d, 336e). In some versions, at least some of the inner nodules (332) of one lateral adjunct section (330a) may be coupled to laterally-adjacent inner nodules (332) of the other lateral adjunct section (330b) by the aforementioned webs. Adjunct (330) may be formed of an elastic, bioabsorbable polymeric (e.g., elastomeric) material having a suitable degree of elasticity that enables adjunct (330) to compress and resiliently resume its original shape. In the present example, each nodule (332) of adjunct (330) is resiliently compressible in such a manner along at least each of its three axes (A1, A2, A3). Additionally, adjunct (330) may be formed as a unitary (e.g., monolithic) structure via an injection molding process, for example.

In this regard, the U-shaped cross-sections of proximal and distal laterally-inner and laterally-outer trunks (336b, 336c, 336d, 336e) in conjunction with the truncated cuboid shape of central body (334) enable the upper portions of each proximal and distal laterally-inner and laterally-outer trunk (336b, 336c, 336d, 336e) opposite the corresponding lower trunk (336a) to collectively define an open upper end, also referred to as a free end (338), of the respective nodule (332) at a tissue-engaging face of adjunct (330). In other words, each nodule (332) lacks an upper trunk opposite lower trunk (336a) along its vertical first axis (A1). Thus, free ends (338) of each nodule (332) are devoid of any undercuts (e.g., internal undercuts, occluded undercuts, etc.) or other geometrical features extending over the hollow interior of the respective nodule (332) such that each hollow interior opens uninterruptedly to the respective free end (338) (e.g., without constricting inwardly). In some versions, each free end (338) may have an inner cross dimension greater than or equal to each inner cross dimension of the respective hollow interior. Adjunct (330) may have at least one undulating cross-sectional side profile, such as with laterally-inner and laterally-outer trunks (336b, 336c, 336d, 336e) defining peaks of the undulating cross-sectional side profile and with lower trunks (336a) defining valleys of the undulating cross-sectional side profile.

It will be appreciated that the absence of undercuts or other geometrical features extending over the hollow interiors of nodules (332) at free ends (338) may enable injection molding of adjunct (330), since the presence of such undercuts or other geometrical features might otherwise interfere with the ability of two mold halves to be separated (e.g., opened) after injection molding adjunct (330) therein. More particularly, a first mold half (not shown) may include a cavity configured to receive molten material for producing the external features of adjunct (330) while a second mold half (not shown) may include a core configured to extend into the cavity for producing the internal features of adjunct (330). Due to the absence of undercuts or other geometrical features extending over the hollow interiors of nodules (332) at free ends (338), such first and second mold halves may be readily separated from each other (e.g., along a horizontal parting line) after injection molding adjunct (330) therein without disrupting the structural integrity of adjunct (330) or of either mold half.

As shown, the hollow interior of each nodule (332) expands (e.g., tapers and/or curves) outwardly from the respective lower trunk (336a) toward (e.g., to) the respective free end (338) at one or more corresponding positive draft angles (e.g., relative to a vertical plane perpendicular to the horizontal parting line of the mold halves) for assisting with separation of the mold halves after injection molding adjunct (330) therein.

Figure 13:
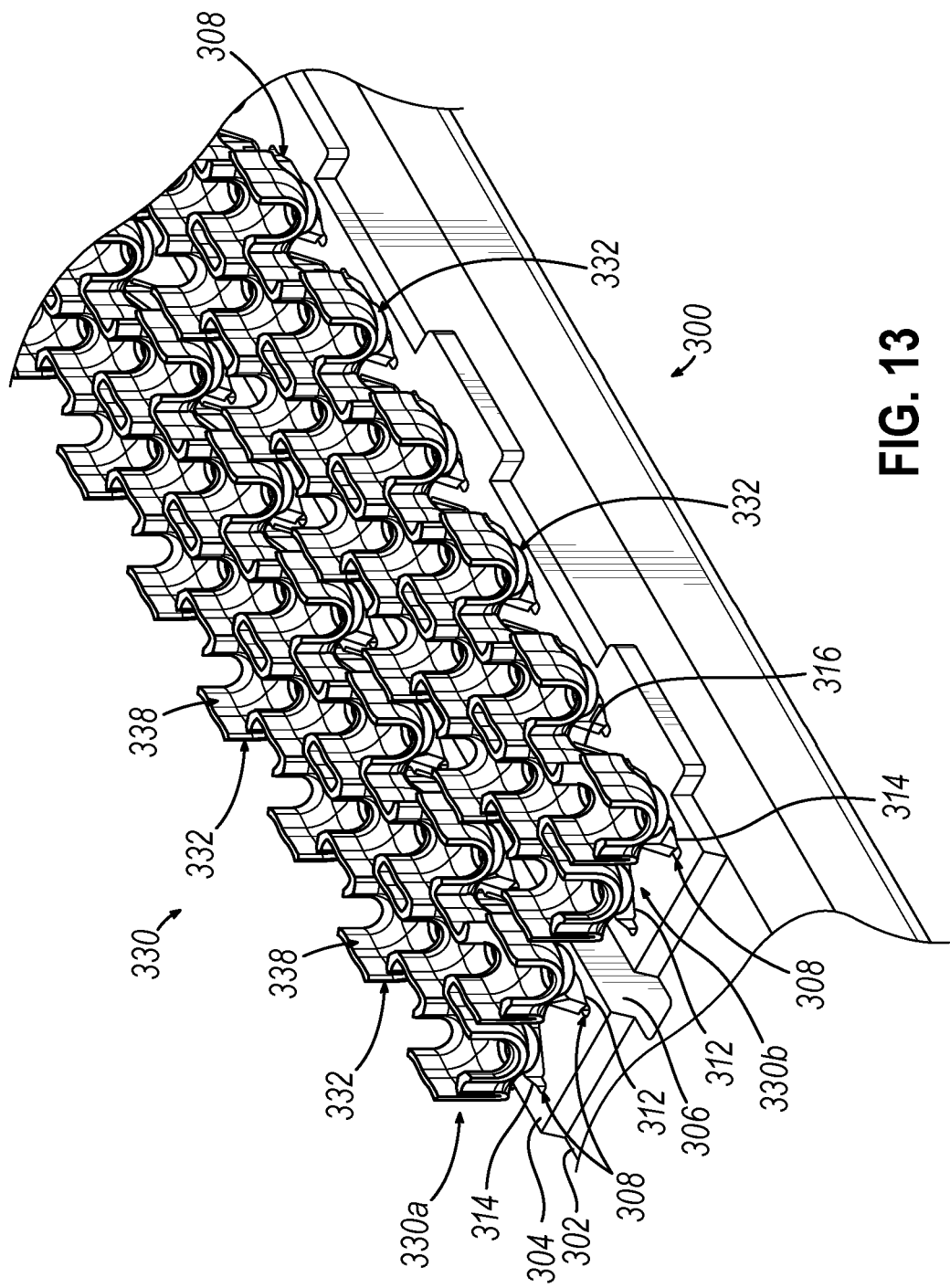
FIG. 13 depicts a partial top perspective view of another exemplary staple cartridge in combination with another alternative exemplary adjunct that is injection-moldable and has nodules configured to be flanked by the legs of staples deployed from the staple cartridge.
Figure 14:
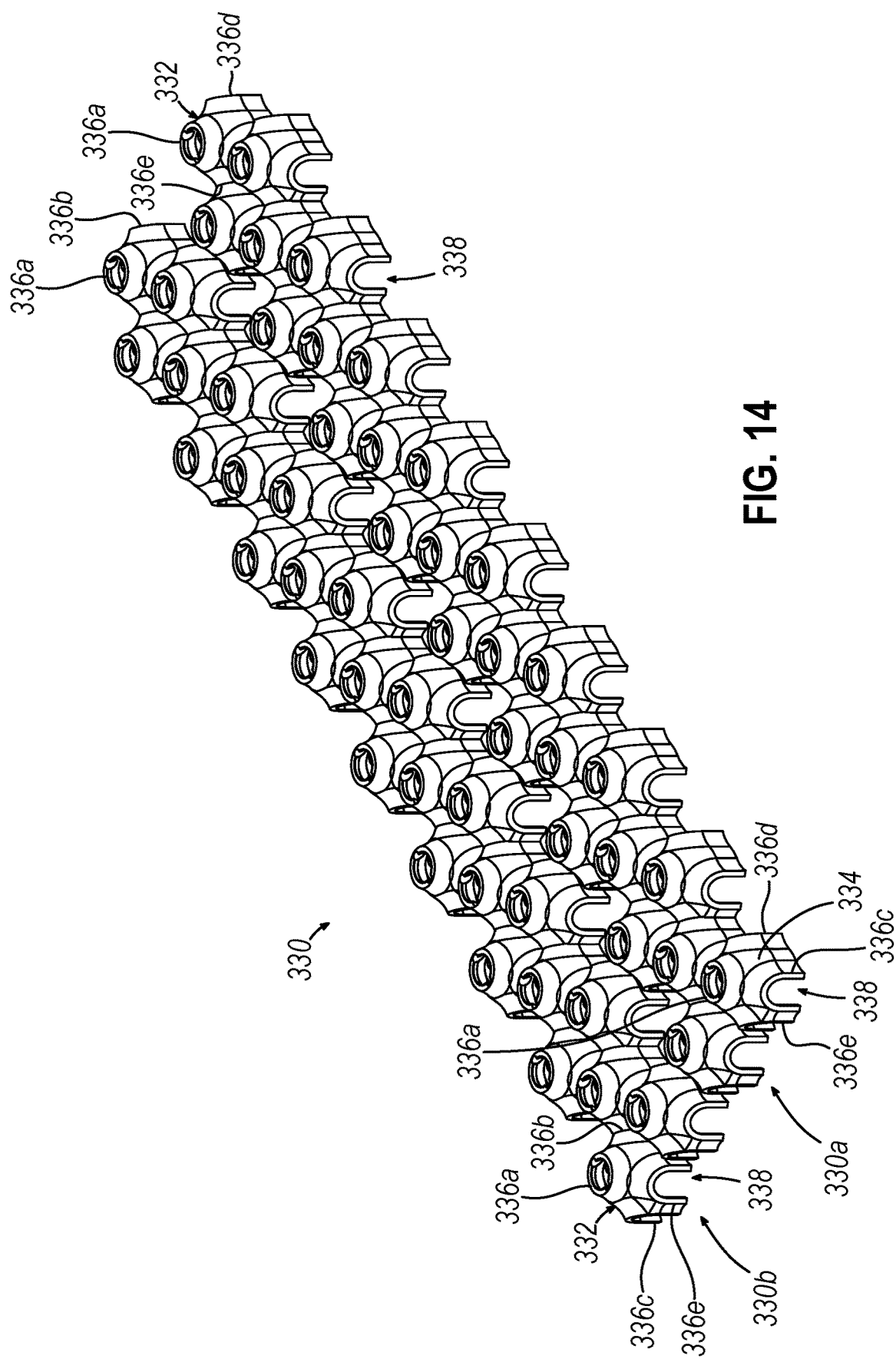
FIG. 14 depicts a bottom perspective view of the adjunct of FIG. 13.
Figure 15:
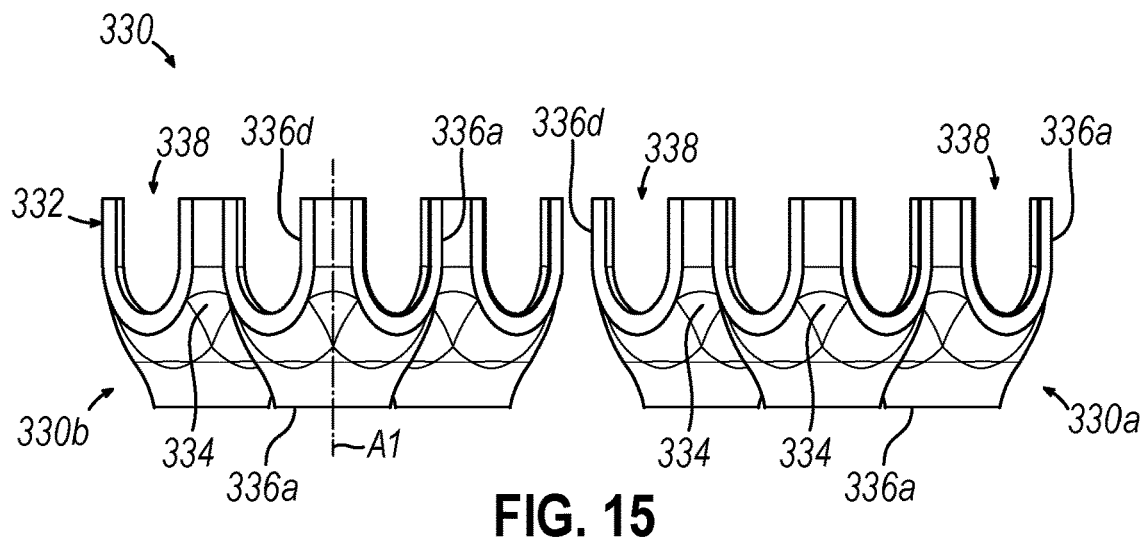
FIG. 15 depicts a front elevational view of the adjunct of FIG. 13.

As shown in FIG. 13, each nodule (332) of adjunct (330) is configured to overlie a corresponding recess (312, 314, 316) and/or a corresponding staple opening (308) of staple cartridge (300). In some versions, at least a portion of the lower trunk (336a) of each nodule (332) may be received within the corresponding recess (312, 314, 316) to promote such overlying of nodules (332) relative to the corresponding recesses (312, 314, 316).

Figure 16:
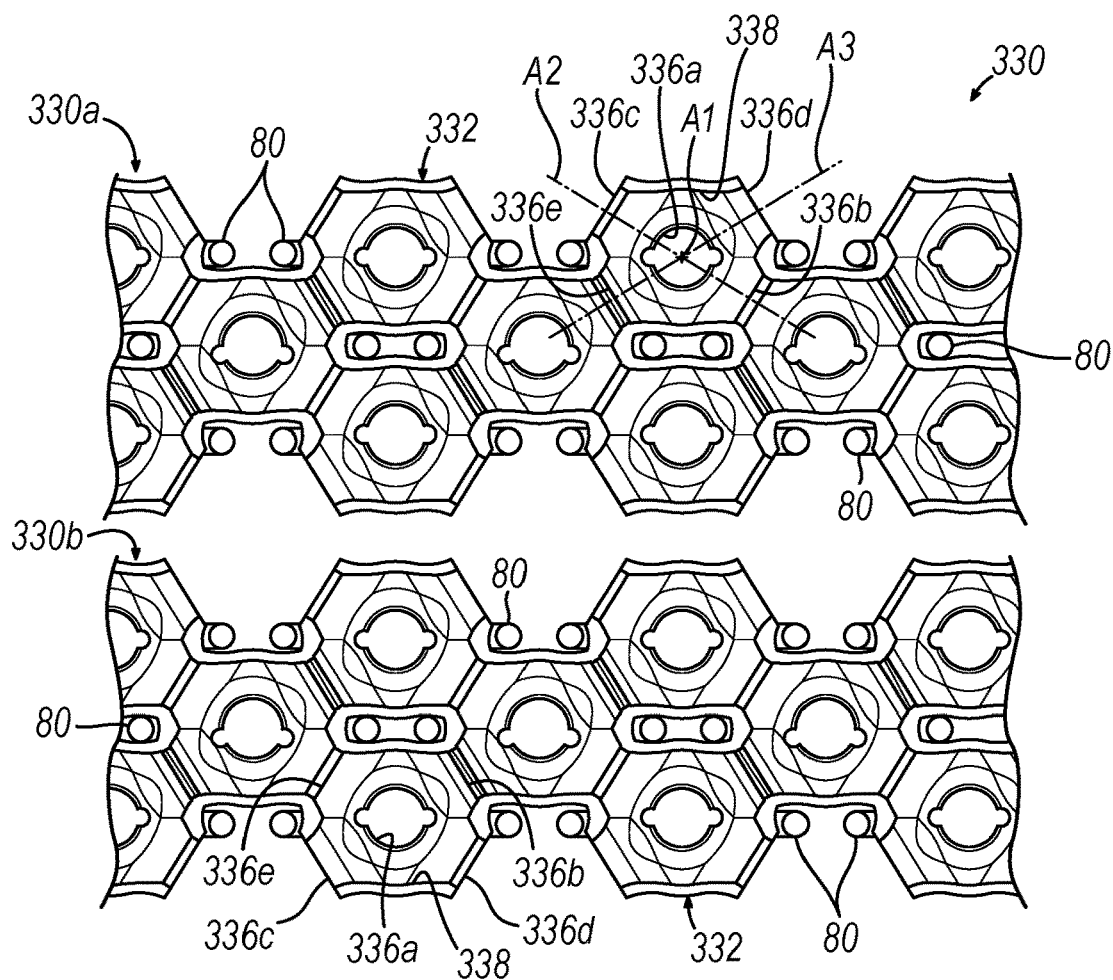
FIG. 16 depicts a partial top plan view of the adjunct of FIG. 13, schematically showing the flanking of the nodules of the adjunct by the legs of the staples deployed from the staple cartridge.

In any event, such overlying of nodules (332) relative to the corresponding recesses (312, 314, 316) may enable the legs of each staple (80) slidably housed within the respective staple opening (308) to flank the corresponding nodule (332) during deployment of staples (80), as shown in FIG. 16. In this manner, the deformed legs of each staple (80) capture and compress the corresponding nodule (332) against the crown thereof when staples (80) are formed by staple forming pockets (58) of anvil (56). Such flanking of nodules (332) by the legs of the corresponding staples (80) may also enable at least some staples (80) to avoid piercing the corresponding nodules (332) during deployment of staples (80).

Figure 17:
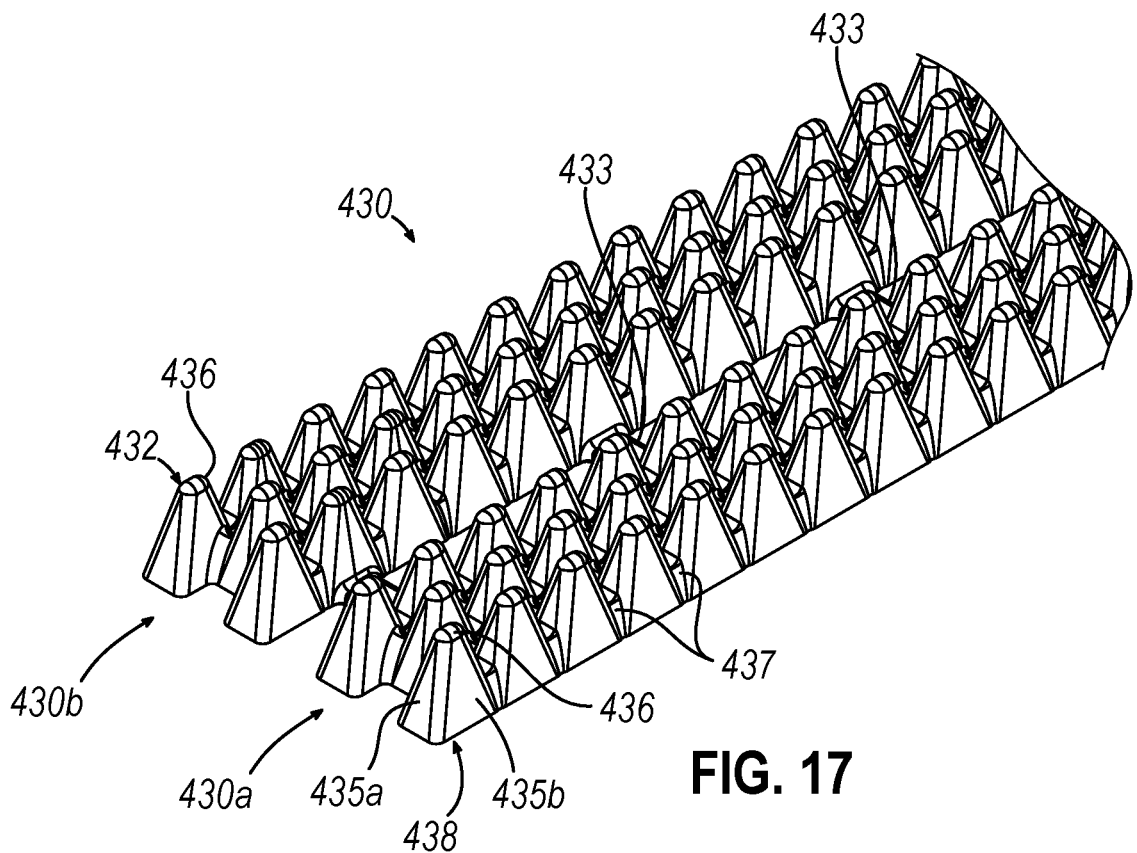
FIG. 17 depicts a partial top perspective view of another alternative exemplary adjunct that is injection-moldable and has pyramid-shaped nodules for engaging tissue, the nodules having a generally uniform configuration.

B. First Exemplary Injection-Moldable Adjunct with Pyramid-Shaped Nodules for Engaging Tissue FIG. 17 shows another exemplary compressible unitary (e.g., monolithic) adjunct (430) configured for releasable attachment to a staple cartridge (not shown) similar to staple cartridge (200). Adjunct (430) is configured for use with end effector (50) and is similar to adjunct (230) described above except as otherwise described below. In this regard, adjunct (430) has a plurality of three-dimensional, resiliently compressible nodules (432) that are integrally connected with one another in a plurality of linear arrays defining a lattice structure having an elongate rectangular shape. In the present example, adjunct (430) includes two lateral adjunct sections (430a, 430b) configured for placement on respective sides of a staple cartridge slot, similar to staple cartridge slot (206), each including inner and outer axial rows of nodules (432) each extending in a proximal-distal direction, and a plurality of transverse rows of nodules (432) each extending in a direction transverse to a length of the staple cartridge. In the example shown, each lateral adjunct section (430a, 430b) also includes a medial axial row of nodules (432) extending in the proximal-distal direction and offset from each of the inner and outer axial rows of nodules (432) in the proximal-distal direction. Additionally, adjunct (430) of the present example has a height of only one nodule (432). It will be appreciated that adjunct (430) of other versions may have various other quantities and configurations of nodules (432). In the example shown, lateral adjunct sections (430a, 430b) are coupled to each other by a plurality of webs (433) extending therebetween and disposed at discrete locations along a length of adjunct (430). Webs (433) may be configured to be severed by cutting edge (62) of firing member (60) during translation thereof through the staple cartridge slot to separate lateral adjunct sections (430a, 430b) from each other.

Each compressible nodule (432) of adjunct (430) is symmetrical about a pair of planes (not shown) that extend through a centroid of nodule (432), including: a first vertical plane that extends parallel to the sidewalls of the staple cartridge slot; and a second vertical plane that extends transversely to the length of the staple cartridge slot. Each nodule (432) of the present example has a hollow interior and is generally pyramid-shaped, having a pair of longitudinal end walls (435a) and a pair of lateral side walls (435b) converging at a respective closed upper tip (436) to define the symmetrical geometrical configuration described above. Adjunct (430) also includes a plurality of bridges (437) extending between respective pairs of nodules (432), as described in greater detail below. In some versions, walls (435a, 435b) and/or bridges (437) may have a substantially uniform thickness for supporting biocompatibility of adjunct (430) by promoting uniform degrading of walls (435a, 435b) and/or bridges (437). For example, each wall (435a, 435b) and/or bridge (437) may have a thickness of about 0.2 mm. In addition, or alternatively, the ratio of the overall height of adjunct (430) to the thickness(es) of walls (435a, 435b) and/or bridges (437) may be between about 4:1 and about 8:1.

As shown, each inner and outer nodule (432) is interconnected with one or two laterally-adjacent medial nodule(s) (432) and with one or two longitudinally-adjacent inner or outer nodule(s) (432), via bridges (437). Each medial nodule (432) is interconnected with one or two laterally-adjacent inner nodule(s) (432), with one or two laterally-adjacent outer nodule(s) (432), and with one or two longitudinally-adjacent medial nodule(s) (432), via bridges (437). In the example shown, some of the inner nodules (432) of one lateral adjunct section (430a) are coupled to laterally-adjacent inner nodules (432) of the other lateral adjunct section (430b) by webs (433). Adjunct (430) may be formed of an elastic, bioabsorbable polymeric (e.g., elastomeric) material having a suitable degree of elasticity that enables adjunct (430) to compress and resiliently resume its original shape. In the present example, each nodule (432) of adjunct (430) is resiliently compressible in such a manner in at least the proximal-distal, transverse, and vertical directions. Additionally, adjunct (430) may be formed as a unitary (e.g., monolithic) structure via an injection molding process, for example.

In this regard, the lower portions of the walls (435a, 435b) of each nodule (432) opposite the corresponding upper tip (436) collectively define an open lower end (438) of the respective nodule (432) at a stapler-engaging face of adjunct (430). Lower ends (438) of each nodule (432) are devoid of any undercuts (e.g., internal undercuts, occluded undercuts, etc.) or other geometrical features extending under the hollow interior of the respective nodule (432) such that each hollow interior opens uninterruptedly to the respective lower end (438) (e.g., without constricting inwardly). In some versions, each lower end (438) may have an inner cross dimension greater than or equal to each inner cross dimension of the respective hollow interior. Adjunct (430) may have at least one undulating cross-sectional side profile, such as with upper tips (436) defining peaks of the undulating cross-sectional side profile and with bridges (437) between longitudinally-adjacent pairs of nodules (432) defining valleys of the undulating cross-sectional side profile.

It will be appreciated that the absence of undercuts or other geometrical features extending under the hollow interiors of nodules (432) at lower ends (438) may enable injection molding of adjunct (430), since the presence of such undercuts or other geometrical features might otherwise interfere with the ability of two mold halves to be separated (e.g., opened) after injection molding adjunct (430) therein. More particularly, a first mold half (not shown) may include a cavity configured to receive molten material for producing the external features of adjunct (430) while a second mold half (not shown) may include a core configured to extend into the cavity for producing the internal features of adjunct (430). Due to the absence of undercuts or other geometrical features extending under the hollow interiors of nodules (432) at lower ends (438), such first and second mold halves may be readily separated from each other (e.g., along a horizontal parting line) after injection molding adjunct (430) therein without disrupting the structural integrity of adjunct (430) or of either mold half.

As shown, the walls (435a, 435b) of each nodule (432) taper outwardly from the respective upper tip (436) toward (e.g., to) the respective lower end (438) at one or more corresponding positive draft angles (e.g., relative to a vertical plane perpendicular to the horizontal parting line of the mold halves) for assisting with separation of the mold halves after injection molding adjunct (430) therein. Likewise, the hollow interior of each nodule (432) may taper and/or curve outwardly from an upper end of the hollow interior toward the respective lower end (438) at one or more corresponding positive draft angles (e.g., relative to a vertical plane perpendicular to the horizontal parting line of the mold halves) for assisting with separation of the mold halves after injection molding adjunct (430) therein.

Each nodule (432) of adjunct (430) may be configured to overlie a corresponding staple cartridge recess, similar to recesses (212, 214, 216), and/or a corresponding staple opening, similar to staple openings (208), of the staple cartridge. In some versions, the lower end (438) of each nodule (432) may be configured to rest on the staple cartridge deck over the corresponding staple cartridge recess.

In any event, such overlying of nodules (432) relative to the corresponding staple cartridge recesses may enable the legs of each staple (not shown) slidably housed within the respective staple opening to flank the corresponding nodule (432) during deployment of the staples. In this manner, the deformed legs of each staple may capture and compress the corresponding nodule (432) against the crown thereof when the staples are formed by staple forming pockets (58) of anvil (56). Such flanking of nodules (432) by the legs of the corresponding staples may also enable at least some staples to avoid piercing the corresponding nodules (432) during deployment of the staples. Rather, one or both legs of each staple may pierce through one or more bridges (437) longitudinally-adjacent to the corresponding nodule (432). It will also be appreciated that upper tips (436) of nodules (432) may engage and apply pressure to the stapled tissue to thereby assist with compressing the stapled tissue. In some versions, adjunct (430) may be configured to provide a stress plateau when compressed for optimally compressing the stapled tissue over a predefined range of tissue thicknesses.

Figure 18:
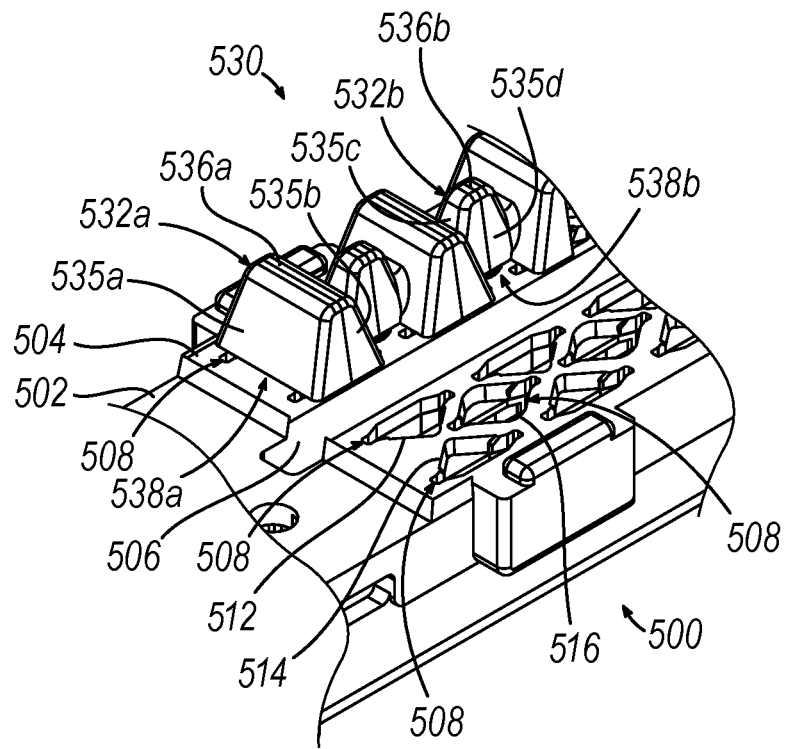
FIG. 18 depicts a partial top perspective view of another exemplary staple cartridge in combination with another alternative exemplary adjunct that is injection-moldable and has pyramid-shaped nodules for engaging tissue, the nodules including narrow nodules and wide nodules.

C. Second Exemplary Injection-Moldable Adjunct with Pyramid-Shaped Nodules for Engaging Tissue FIG. 18 shows a portion of another exemplary compressible unitary (e.g., monolithic) adjunct (530) configured for releasable attachment to a staple cartridge (500). Staple cartridge (500) and adjunct (530) are configured for use with end effector (50) and are similar to staple cartridge (200) and adjunct (430) described above except as otherwise described below. In this regard, staple cartridge (500) includes a cartridge body (502) having an upwardly facing deck (504), an elongate slot (506) extending along a central axis of cartridge body (502) and opening upwardly through deck (504), and a plurality of staple openings (508) extending through deck (504) on each side of elongate slot (506). Each staple opening (508) slidably houses an unformed staple (not shown), similar to staple (80), and a respective staple driver (not shown), similar to staple driver (82), configured to drive the corresponding staple outwardly toward anvil (56) to be formed. A lower tray (not shown) of staple cartridge (500) retains the staples and the staple drivers within cartridge body (502). Cartridge body (502) of the present example further includes a plurality of upwardly-opening recesses (512, 514, 516) formed in deck (504) and having base surfaces through which staple openings (508) extend. More specifically, on each side of elongate slot (506), deck (504) includes an inner row of triangular recesses (512) each having a medial apex that points transversely away from elongate slot (506); an outer row of triangular recesses (514) each having a medial apex that points transversely toward elongate slot (506); and a middle row of diamond-shaped recesses (516) each having an inner medial apex that points transversely toward elongate slot (506) and an opposed outer medial apex that points transversely away from elongate slot (506).

Adjunct (530) has a plurality of three-dimensional, resiliently compressible nodules (532a, 532b) that are integrally connected with one another in a linear array defining a lattice structure having an elongate rectangular shape. In the present example, adjunct (530) includes two lateral adjunct sections (one shown) configured for placement on respective sides of staple cartridge slot (506), each including an axial row of nodules (532a, 532b) extending in a proximal-distal direction and alternating between wide nodules (532a) and narrow nodules (532b). Additionally, adjunct (530) of the present example has a height of only one nodule (532a, 532b). It will be appreciated that adjunct (530) of other versions may have various other quantities and configurations of nodules (532a, 532b).

Each compressible nodule (532a, 532b) of adjunct (530) is symmetrical about a pair of planes (not shown) that extend through a centroid of nodule (532), including: a first vertical plane that extends parallel to the sidewalls of staple cartridge slot (506); and a second vertical plane that extends transversely to the length of staple cartridge slot (506). Each wide nodule (532a) of the present example has a hollow interior and is generally pyramid-shaped, having a pair of longitudinal end walls (535a) and a pair of lateral side walls (535b) converging at a respective closed upper tip (536a), while each narrow nodule (532b) of the present example has a hollow interior and is generally pyramid-shaped, having a pair of longitudinal end walls (535c) and a pair of lateral side walls (535d) converging at a respective closed upper tip (536b) to define the symmetrical geometrical configurations described above. Adjunct (530) also includes a plurality of bridges (537) extending between respective pairs of nodules (532a, 532b). As shown, each wide nodule (532a) is interconnected with one or two longitudinally-adjacent narrow nodule(s) (532b), via bridges (537). Each narrow nodule (532b) is interconnected with one or two longitudinally-adjacent wide nodule(s) (532a), via bridges (537).

The lower portions of the walls (535a, 535b, 535c, 535d) of each nodule (532a, 532b) opposite the corresponding upper tip (536a, 536b) collectively define an open lower end (538a, 538b) of the respective nodule (532a, 532b) at a stapler-engaging face of adjunct (530). Lower ends (538a, 538b) of each nodule (532a, 532b) are devoid of any undercuts (e.g., internal undercuts, occluded undercuts, etc.) or other geometrical features extending under the hollow interior of the respective nodule (532a, 532b) such that each hollow interior opens uninterruptedly to the respective lower end (538a, 538b) to enable injection molding of adjunct (530), in a manner similar to that described above in connection with FIG. 17. Adjunct (530) may have at least one undulating cross-sectional side profile, such as with upper tips (536a, 536b) defining peaks of the undulating cross-sectional side profile and with bridges (537) between longitudinally-adjacent pairs of nodules (532a, 532b) defining valleys of the undulating cross-sectional side profile.

As shown in FIG. 18, each nodule (532a, 532b) of adjunct (530) is configured to overlie one or more corresponding recess(es) (512, 514, 516) and/or a corresponding staple opening (508) of staple cartridge (500). More particularly, each wide nodule (532a) is configured to overlie a corresponding pair of laterally-adjacent triangular recesses (512, 514), and each narrow nodule (532b) is configured to overlie a corresponding diamond-shaped recess (516). In some versions, the lower end (538a, 538b) of each nodule (532a, 532b) may be configured to rest on deck (504) over the corresponding recess(es) (512, 514, 516).

In any event, such overlying of nodules (532a, 532b) relative to the corresponding recess(es) (512, 514, 516) may enable the legs of each staple (not shown) slidably housed within the respective staple opening (508) to flank the corresponding nodule (532a, 532b) during deployment of the staples. In this manner, the deformed legs of each staple may capture and compress the corresponding nodule (532a, 532b) against the crown thereof when the staples are formed by staple forming pockets (58) of anvil (56). Such flanking of nodules (532a, 532b) by the legs of the corresponding staples may also enable at least some staples to avoid piercing the corresponding nodules (532a, 532b) during deployment of the staples. Rather, one or both legs of each staple flanking a corresponding narrow nodule (532b) may pierce through one or more bridges (537) longitudinally-adjacent to the corresponding narrow nodule (532b). It will also be appreciated that upper tips (536) of nodules (532a, 532b) may engage and apply pressure to the stapled tissue to thereby assist with compressing the stapled tissue. In some versions, adjunct (530) may be configured to provide a stress plateau when compressed for optimally compressing the stapled tissue over a predefined range of tissue thicknesses.

Figure 19:
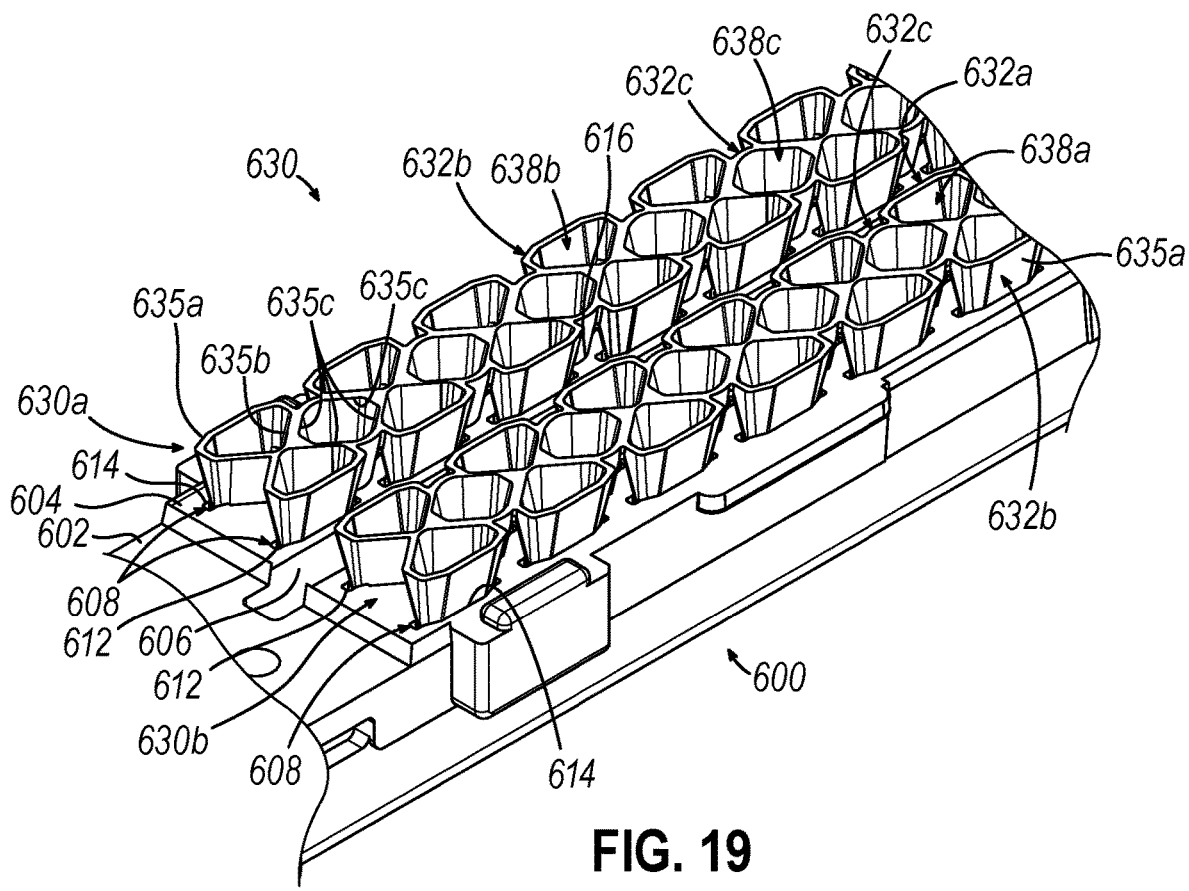
FIG. 19 depicts a partial top perspective view of another exemplary staple cartridge in combination with another alternative exemplary adjunct that is injection-moldable and has pyramid-shaped nodules for engaging the staple cartridge.
Figure 20:
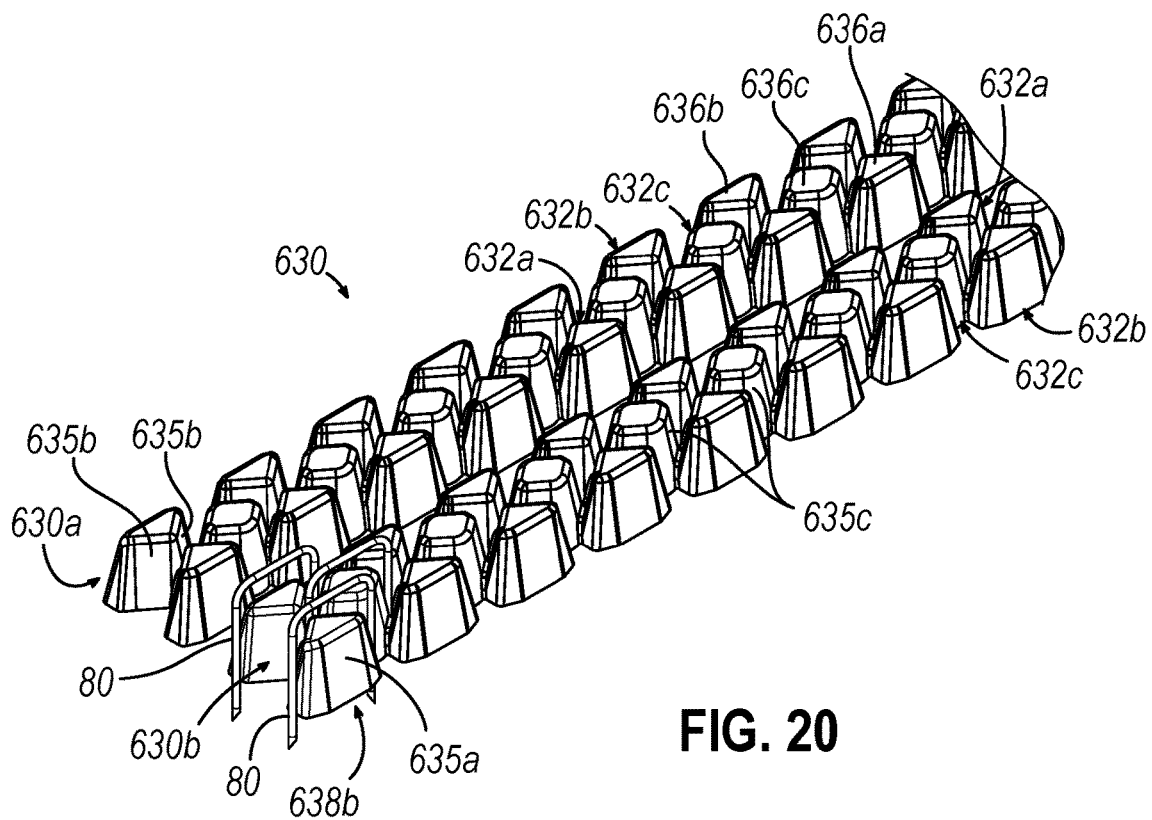
FIG. 20 depicts a partial bottom perspective view of the adjunct of FIG. 19, schematically showing the flanking of the nodules of the adjunct by the legs of the staples deployed from the staple cartridge.

D. First Exemplary Injection-Moldable Adjunct with Pyramid-Shaped Nodules for Engaging Staple Cartridge FIGS. 19-20 show another exemplary compressible unitary (e.g., monolithic) adjunct (630) configured for releasable attachment to a staple cartridge (600). Staple cartridge (600) and adjunct (630) are configured for use with end effector (50) and are similar to staple cartridge (200) and adjunct (230) described above except as otherwise described below. In this regard, staple cartridge (600) includes a cartridge body (602) having an upwardly facing deck (604), an elongate slot (606) extending along a central axis of cartridge body (602) and opening upwardly through deck (604), and a plurality of staple openings (608) extending through deck (604) on each side of elongate slot (606). Each staple opening (608) slidably houses an unformed staple (80) (FIG. 20), and a respective staple driver (not shown), similar to staple driver (82), configured to drive the corresponding staple (80) outwardly toward anvil (56) to be formed. A lower tray (not shown) of staple cartridge (600) retains staples (80) and the staple drivers within cartridge body (602). Cartridge body (602) of the present example further includes a plurality of upwardly-opening recesses (612, 614, 616) formed in deck (604) and having base surfaces through which staple openings (608) extend. More specifically, on each side of elongate slot (606), deck (604) includes an inner row of triangular recesses (612) each having a medial apex that points transversely away from elongate slot (606); an outer row of triangular recesses (614) each having a medial apex that points transversely toward elongate slot (606); and a middle row of diamond-shaped recesses (616) each having an inner medial apex that points transversely toward elongate slot (606) and an opposed outer medial apex that points transversely away from elongate slot (606).

Adjunct (630) has a plurality of three-dimensional, resiliently compressible nodules (632a, 632b, 632c) that are integrally connected with one another in a plurality of linear arrays defining a lattice structure having an elongate rectangular shape. In the present example, adjunct (630) includes two lateral adjunct sections (630a, 630b) configured for placement on respective sides of staple cartridge slot (606), each including inner and outer axial rows of nodules (632a, 632b) each extending in a proximal-distal direction, and a plurality of transverse rows of nodules (632a, 632b) each extending in a direction transverse to a length of the staple cartridge. In the example shown, each lateral adjunct section (630a, 630b) also includes a medial axial row of nodules (632c) extending in the proximal-distal direction and offset from each of the inner and outer axial rows of nodules (632a, 632b) in the proximal-distal direction. Additionally, adjunct (630) of the present example has a height of only one nodule (632a, 632b, 632c). It will be appreciated that adjunct (630) of other versions may have various other quantities and configurations of nodules (632a, 632b, 632c). In some versions, lateral adjunct sections (630a, 630b) may be coupled to each other by one or more webs (not shown) extending therebetween. For example, a plurality of such webs may be disposed at discrete locations along a length of adjunct (630). In any event, such web(s) may be configured to be severed by cutting edge (62) of firing member (60) during translation thereof through staple cartridge slot (606) to separate lateral adjunct sections (630a, 630b) from each other.

Each inner and outer compressible nodule (632a, 632b) of adjunct (630) is symmetrical about a single vertical plane (not shown) that extends through a centroid of nodule (632a, 632b) and transversely to the length of staple cartridge slot (606). Each inner and outer nodule (632a, 632b) of the present example has a hollow interior and is generally pyramid-shaped, having a first, longitudinally-extending wall (635a) and a pair of equally-sized, obliquely-extending second walls (635b) converging toward a respective closed lower end (636a, 636b) to define the symmetrical geometrical configuration described above. More specifically, each inner nodule (632a) has a generally triangular cross-section with a medial apex that points transversely away from elongate slot (606), and each outer nodule (632b) has a generally triangular cross-section with a medial apex that points transversely toward elongate slot (606).

Each medial compressible nodule (632c) of adjunct (630) is symmetrical about a pair of planes (not shown) that extend through a centroid of nodule (632c), including: a first vertical plane that extends parallel to the sidewalls of staple cartridge slot (606); and a second vertical plane that extends transversely to the length of staple cartridge slot (606). Each medial nodule (632c) of the present example has a hollow interior and is generally pyramid-shaped, having four equally-sized, obliquely-extending walls (635c) converging toward a respective closed lower end (636c) to define the symmetrical geometrical configuration described above. More specifically, each medial nodule (632c) has a generally diamond-shaped cross-section with an inner medial apex that points transversely toward elongate slot (606) and an opposed outer medial apex that points transversely away from elongate slot (606). In some versions, walls (635a, 635b, 635c) may have a substantially uniform thickness for supporting biocompatibility of adjunct (630) by promoting uniform degrading of walls (635a, 635b, 635c). For example, each wall (635a, 635b, 635c) may have a thickness of about 0.2 mm. In addition, or alternatively, the ratio of the overall height of adjunct (630) to the thickness(es) of walls (635a, 635b, 635c) may be between about 4:1 and about 8:1.

As shown, each inner and outer nodule (632a, 632b) is interconnected with one or two laterally-adjacent medial nodule(s) (632c), via upper portions of the respective walls (635a, 635b, 635c) directly interfacing with each other. Each medial nodule (632c) is interconnected with one or two laterally-adjacent inner nodule(s) (632a) and with one or two laterally-adjacent outer nodule(s) (632b), via upper portions of the respective walls (635a, 635b, 635c) directly interfacing with each other. In some versions, at least some of the inner nodules (632a) of one lateral adjunct section (630a) may be coupled to laterally-adjacent inner nodules (632a) of the other lateral adjunct section (630b) by the aforementioned webs. Adjunct (630) may be formed of an elastic, bioabsorbable polymeric (e.g., elastomeric) material having a suitable degree of elasticity that enables adjunct (630) to compress and resiliently resume its original shape. In the present example, each nodule (632a, 632b, 632c) of adjunct (630) is resiliently compressible in such a manner in at least the proximal-distal, transverse, and vertical directions. Additionally, adjunct (630) may be formed as a unitary (e.g., monolithic) structure via an injection molding process, for example.

In this regard, the upper portions of the walls (635a, 635b, 635c) of each nodule (632a, 632b, 632c) opposite the corresponding lower end (636a, 636b, 636c) collectively define an open upper end (638a, 638b, 638c) of the respective nodule (632a, 632b, 632c) at a tissue-engaging face of adjunct (630). Upper ends (638a, 638b, 638c) of each nodule (632a, 632b, 632c) are devoid of any undercuts (e.g., internal undercuts, occluded undercuts, etc.) or other geometrical features extending over the hollow interior of the respective nodule (632a, 632b, 632c) such that each hollow interior opens uninterruptedly to the respective upper end (638a, 638b, 638c) (e.g., without constricting inwardly). In some versions, each upper end (638a, 638b, 638c) may have an inner cross dimension greater than or equal to each inner cross dimension of the respective hollow interior. Adjunct (630) may have at least one undulating cross-sectional side profile, such as with the interfaces between upper portions of the walls (635a, 635b, 635c) of longitudinally-adjacent pairs of nodules (632a, 632b, 632c) defining peaks of the undulating cross-sectional side profile and with lower ends (636a, 636b, 636c) defining valleys of the undulating cross-sectional side profile.

It will be appreciated that the absence of undercuts or other geometrical features extending over the hollow interiors of nodules (632a, 632b, 632c) at upper ends (638a, 638b, 638c) may enable injection molding of adjunct (630), since the presence of such undercuts or other geometrical features might otherwise interfere with the ability of two mold halves to be separated (e.g., opened) after injection molding adjunct (630) therein. More particularly, a first mold half (not shown) may include a cavity configured to receive molten material for producing the external features of adjunct (630) while a second mold half (not shown) may include a core configured to extend into the cavity for producing the internal features of adjunct (630). Due to the absence of undercuts or other geometrical features extending over the hollow interiors of nodules (632a, 632b, 632c) at upper ends (638a, 638b, 638c), such first and second mold halves may be readily separated from each other (e.g., along a horizontal parting line) after injection molding adjunct (630) therein without disrupting the structural integrity of adjunct (630) or of either mold half.

As shown, the walls (635a, 635b, 635c) of each nodule (632a, 632b, 632c) taper outwardly from the respective lower end (636a, 636b, 636c) toward (e.g., to) the respective upper end (638a, 638b, 638c) at one or more corresponding positive draft angles (e.g., relative to a vertical plane perpendicular to the horizontal parting line of the mold halves) for assisting with separation of the mold halves after injection molding adjunct (630) therein. Likewise, the hollow interior of each nodule (632a, 632b, 632c) may taper and/or curve outwardly from a lower end of the hollow interior toward the respective upper end (638a, 638b, 638c) at one or more corresponding positive draft angles (e.g., relative to a vertical plane perpendicular to the horizontal parting line of the mold halves) for assisting with separation of the mold halves after injection molding adjunct (630) therein.

As shown in FIG. 19, each nodule (632a, 632b, 632c) of adjunct (430) is configured to align with a corresponding recess (612, 614, 616) of staple cartridge (600). More particularly, each inner nodule (632a) is configured to align with a corresponding inner recess (612), each outer nodule (632b) is configured to align with a corresponding outer recess (614), and each medial nodule (632c) is configured to align with a corresponding medial recess (616). In the example shown, at least a portion of each nodule (632a, 632b, 632c) (e.g., at or near lower end (636a, 636b, 636c)) is configured to be received within the corresponding recess (612, 614, 616) to promote such alignment of nodules (632a, 632b, 632c) with the corresponding recesses (612, 614, 616).

Such alignment of nodules (632a, 632b, 632c) with the corresponding recesses (612, 614, 616) may enable the legs of each staple (80) slidably housed within the respective staple opening (608) to flank the corresponding nodule (632a, 632b, 632c) during deployment of staples (80), as shown in FIG. 20. In this manner, the deformed legs of each staple (80) may capture and compress the corresponding nodule (632a, 632b, 632c) against the crown thereof when staples (80) are formed by staple forming pockets (58) of anvil (56). Such flanking of nodules (632a, 632b, 632c) by the legs of the corresponding staples (80) may also enable at least some staples (80) to avoid piercing the corresponding nodules (632a, 632b, 632c) during deployment of the staples. In some versions, adjunct (630) may include notches (not shown) at the lower ends (636a, 636b, 636c) of nodules (632a, 632b, 632c) for receiving the crowns of the corresponding staples (80) to inhibit slipping of staples (80) relative to the corresponding nodules (632a, 632b, 632c) and thereby assist with achieving proper flanking of nodules (632a, 632b, 632c) by staples (80). It will also be appreciated that upper ends (638a, 638b, 638c) of nodules (632a, 632b, 632c) may engage and apply pressure to the stapled tissue to thereby assist with compressing the stapled tissue. In some versions, adjunct (630) may be configured to provide a stress plateau when compressed for optimally compressing the stapled tissue over a predefined range of tissue thicknesses.

Figure 21:
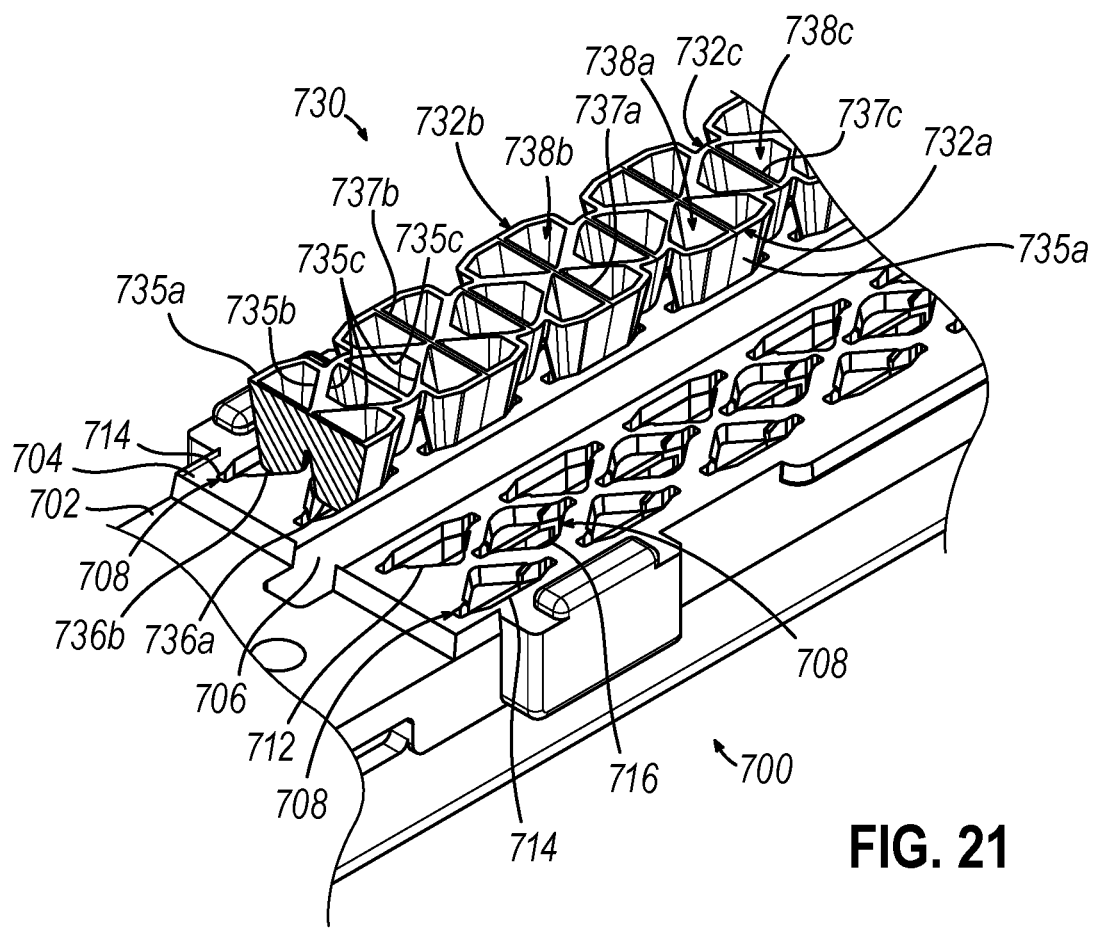
FIG. 21 depicts a partial top perspective view of another exemplary staple cartridge in combination with another alternative exemplary adjunct that is injection-moldable and has pyramid-shaped nodules for engaging the staple cartridge, the nodules including partitions extending across hollow interiors thereof.

E. Second Exemplary Injection-Moldable Adjunct with Pyramid-Shaped Nodules for Engaging Staple Cartridge FIG. 21 shows another exemplary compressible unitary (e.g., monolithic) adjunct (730) configured for releasable attachment to a staple cartridge (700). Staple cartridge (700) and adjunct (730) are configured for use with end effector (50) and are similar to staple cartridge (600) and adjunct (630) described above except as otherwise described below. In this regard, staple cartridge (700) includes a cartridge body (702) having an upwardly facing deck (704), an elongate slot (706) extending along a central axis of cartridge body (702) and opening upwardly through deck (704), and a plurality of staple openings (708) extending through deck (704) on each side of elongate slot (706). Each staple opening (708) slidably houses an unformed staple (not shown), similar to staple (80), and a respective staple driver (not shown), similar to staple driver (82), configured to drive the corresponding staple outwardly toward anvil (56) to be formed. A lower tray (not shown) of staple cartridge (700) retains the staples and the staple drivers within cartridge body (702). Cartridge body (702) of the present example further includes a plurality of upwardly-opening recesses (712, 714, 716) formed in deck (704) and having base surfaces through which staple openings (708) extend. More specifically, on each side of elongate slot (706), deck (704) includes an inner row of triangular recesses (712) each having a medial apex that points transversely away from elongate slot (706); an outer row of triangular recesses (714) each having a medial apex that points transversely toward elongate slot (706); and a middle row of diamond-shaped recesses (716) each having an inner medial apex that points transversely toward elongate slot (706) and an opposed outer medial apex that points transversely away from elongate slot (706).

Adjunct (730) has a plurality of three-dimensional, resiliently compressible nodules (732a, 732b, 732c) that are integrally connected with one another in a plurality of linear arrays defining a lattice structure having an elongate rectangular shape. In the present example, adjunct (730) includes two lateral adjunct sections (730a, 730b) configured for placement on respective sides of staple cartridge slot (706), each including inner, outer, and medial axial rows of nodules (732a, 732b, 732c) in a manner similar to that described above in connection with FIGS. 19-20.

Each inner and outer compressible nodule (732a, 732b) of adjunct (730) is symmetrical about a single vertical plane (not shown) that extends through a centroid of nodule (732a, 732b) and transversely to the length of staple cartridge slot (706). Each inner and outer nodule (732a, 732b) of the present example has a hollow interior and is generally pyramid-shaped, having a first, longitudinally-extending wall (735a) and a pair of equally-sized, obliquely-extending second walls (735b) converging toward a respective closed lower end (736a, 736b) to define the symmetrical geometrical configuration described above. More specifically, each inner nodule (732a) has a generally triangular cross-section with a medial apex that points transversely away from elongate slot (706), and each outer nodule (732b) has a generally triangular cross-section with a medial apex that points transversely toward elongate slot (706). In the example shown, each inner and outer nodule (732a, 732b) also includes at least one cross support in the form of a transverse partition (737a, 737b) extending across the hollow interior thereof and bifurcating the medial apex thereof.

Each medial compressible nodule (732c) of adjunct (730) is symmetrical about a pair of planes (not shown) that extend through a centroid of nodule (732c), including: a first vertical plane that extends parallel to the sidewalls of staple cartridge slot (706); and a second vertical plane that extends transversely to the length of staple cartridge slot (706). Each medial nodule (732c) of the present example has a hollow interior and is generally pyramid-shaped, having four equally-sized, obliquely-extending walls (735c) converging toward a respective closed lower end (not shown) to define the symmetrical geometrical configuration described above. More specifically, each medial nodule (732c) has a generally diamond-shaped cross-section with an inner medial apex that points transversely toward elongate slot (706) and an opposed outer medial apex that points transversely away from elongate slot (706). In the example shown, each medial nodule (732c) also includes at least one transverse partition (737c) extending across the hollow interior thereof and bifurcating the inner and outer medial apexes thereof. In some versions, walls (735a, 735b, 735c) and/or partitions (737a, 737b, 737c) may have a substantially uniform thickness for supporting biocompatibility of adjunct (730) by promoting uniform degrading of walls (735a, 735b, 735c) and/or partitions (737a, 737b, 737c). For example, each wall (735a, 735b, 735c) and/or partition (737a, 737b, 737c) may have a thickness of about 0.2 mm. In addition, or alternatively, the ratio of the overall height of adjunct (730) to the thickness(es) of walls (735a, 735b, 735c) and/or partitions (737a, 737b, 737c) may be between about 4:1 and about 8:1.

As shown, each inner and outer nodule (732a, 732b) is interconnected with one or two laterally-adjacent medial nodule(s) (732c), and each medial nodule (732c) is interconnected with one or two laterally-adjacent inner nodule(s) (732a) and with one or two laterally-adjacent outer nodule(s) (732b), in manners similar to those described above in connection with FIGS. 19-20.

The upper portions of the walls (735a, 735b, 735c) and partitions (737a, 737b, 737c) of each nodule (732a, 732b, 732c) opposite the corresponding lower end (736a, 736b) collectively define an open upper end (738a, 738b, 738c) of the respective nodule (732a, 732b, 732c) at a tissue-engaging face of adjunct (730). Upper ends (738a, 738b, 738c) of each nodule (732a, 732b, 732c) are devoid of any undercuts (e.g., internal undercuts, occluded undercuts, etc.) or other geometrical features extending over the hollow interior of the respective nodule (732a, 732b, 732c) such that each hollow interior opens uninterruptedly to the respective upper end (738a, 738b, 738c) to enable injection molding of adjunct (730), in a manner similar to that described above in connection with FIGS. 19-20. Adjunct (730) may have at least one undulating cross-sectional side profile, such as with the interfaces between upper portions of the walls (735a, 735b, 735c) of longitudinally-adjacent pairs of nodules (732a, 732b, 732c) defining peaks of the undulating cross-sectional side profile and with lower ends (736a, 736b) defining valleys of the undulating cross-sectional side profile.

As shown in FIG. 21, each nodule (732a, 732b, 732c) of adjunct (430) is configured to align with a corresponding recess (712, 714, 716) of staple cartridge (700) to enable the legs of each staple (not shown) slidably housed within the respective staple opening (708) to flank the corresponding nodule (732a, 732b, 732c) during deployment of the staples, in a manner similar to that described above in connection with FIGS. 19-20. It will also be appreciated that upper ends (738a, 738b, 738c) of nodules (732a, 732b, 732c) may engage and apply pressure to the stapled tissue to thereby assist with compressing the stapled tissue. In some versions, adjunct (730) may be configured to provide a stress plateau when compressed for optimally compressing the stapled tissue over a predefined range of tissue thicknesses.

Figure 22:
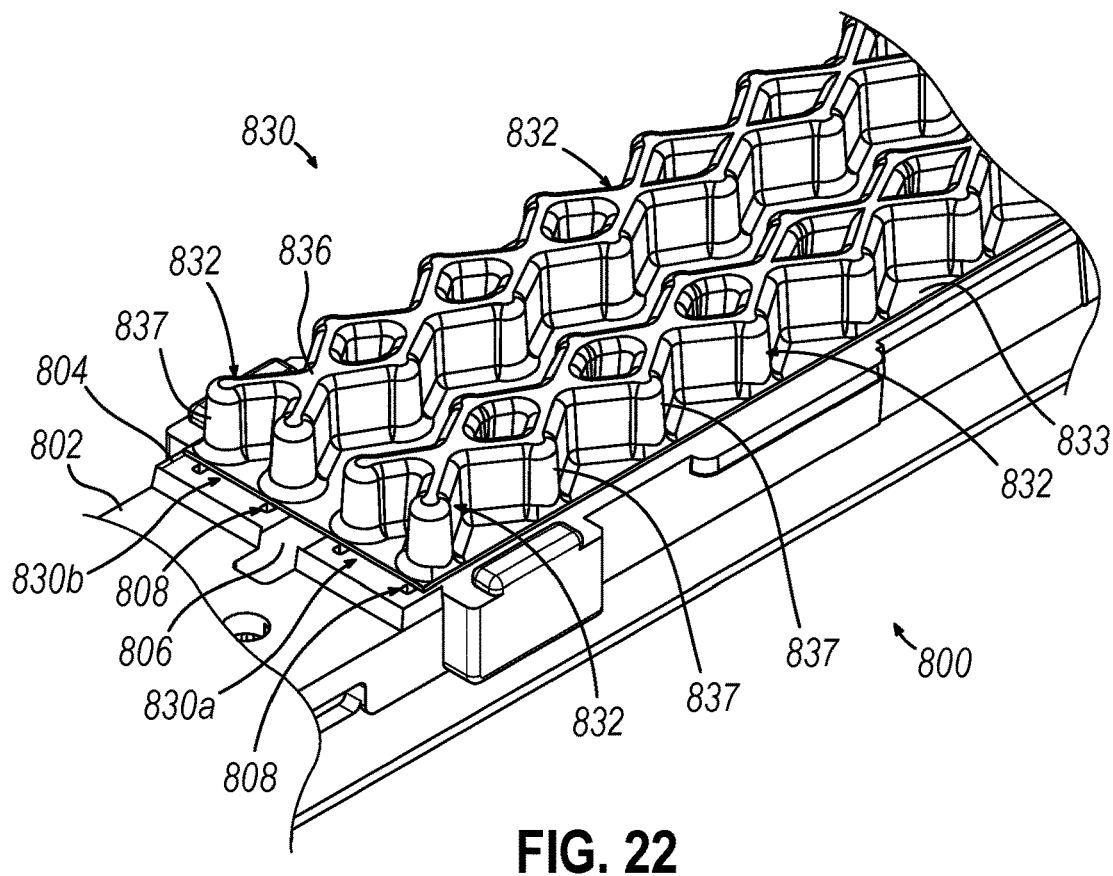
FIG. 22 depicts a partial top perspective view of another exemplary staple cartridge in combination with another alternative exemplary adjunct that is thermoformable and has X-shaped protrusions configured to be flanked by the legs of staples deployed from the staple cartridge.
Figure 23:
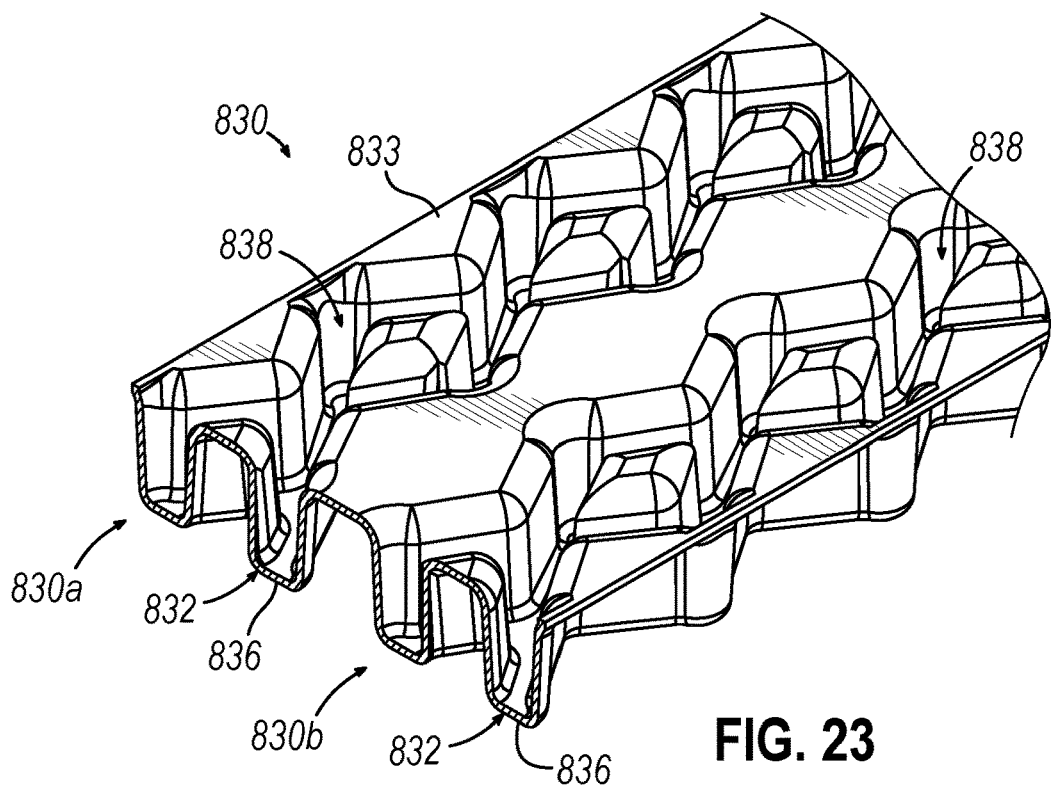
FIG. 23 depicts a partial bottom perspective view of the adjunct of FIG. 22.
Figure 24:
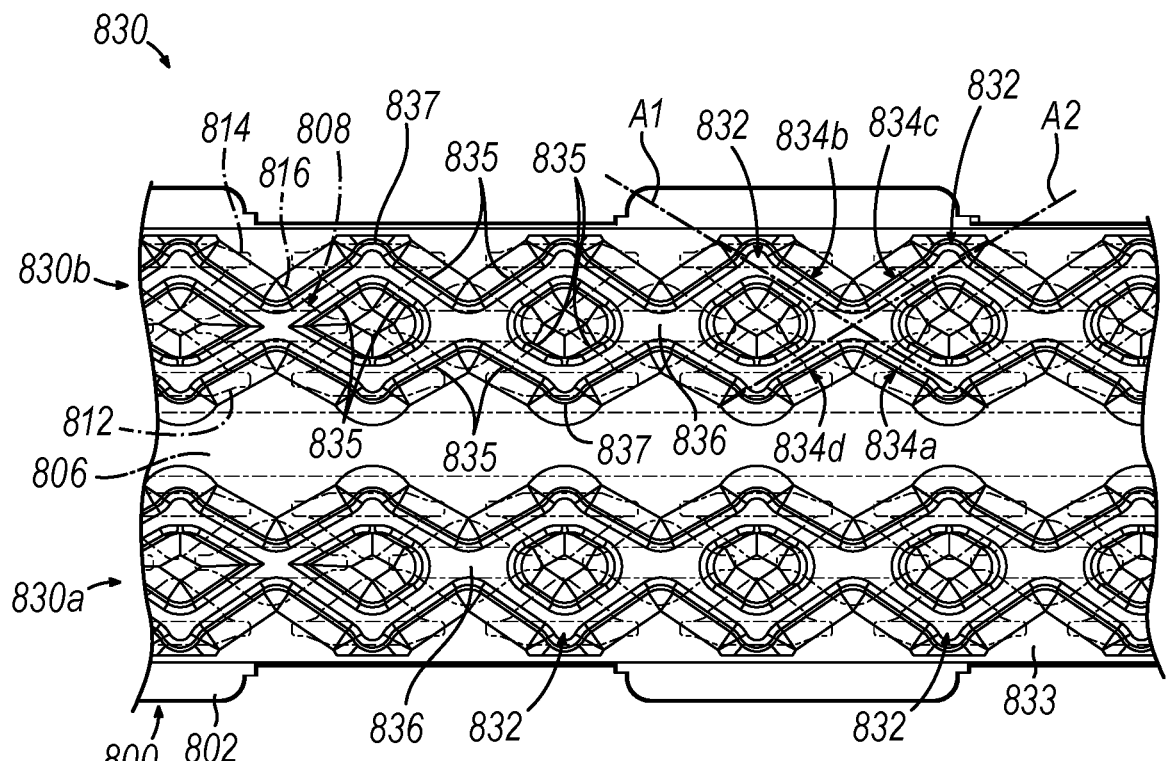
FIG. 24 depicts a partial top plan view of the staple cartridge of FIG. 22 in combination with the adjunct of FIG. 22, showing the X-shaped protrusions at least partially overlying respective recesses and/or staple openings of the staple cartridge.

F. First Exemplary Thermoformable Adjunct with X-Shaped Protrusions Configured to be Flanked by Staple Legs FIGS. 22-24 show another exemplary compressible unitary (e.g., monolithic) adjunct (830) configured for releasable attachment to a staple cartridge (800). Staple cartridge (800) and adjunct (830) are configured for use with end effector (50) and are similar to staple cartridge (200) and adjunct (230) described above except as otherwise described below. In this regard, staple cartridge (800) includes a cartridge body (802) having an upwardly facing deck (804), an elongate slot (806) extending along a central axis of cartridge body (802) and opening upwardly through deck (804), and a plurality of staple openings (808) extending through deck (804) on each side of elongate slot (806). Each staple opening (808) slidably houses an unformed staple (not shown), similar to staple (80), and a respective staple driver (not shown), similar to staple driver (82), configured to drive the corresponding staple outwardly toward anvil (56) to be formed. A lower tray (not shown) of staple cartridge (800) retains the staples and the staple drivers within cartridge body (802). Cartridge body (802) of the present example further includes a plurality of upwardly-opening recesses (812, 814, 816) formed in deck (804) and having base surfaces through which staple openings (808) extend. More specifically, on each side of elongate slot (806), deck (804) includes an inner row of triangular recesses (812) each having a medial apex that points transversely away from elongate slot (806); an outer row of triangular recesses (814)

each having a medial apex that points transversely toward elongate slot (806); and a middle row of diamond-shaped recesses (816) each having an inner medial apex that points transversely toward elongate slot (806) and an opposed outer medial apex that points transversely away from elongate slot (806).

Adjunct (830) has a plurality of three-dimensional, resiliently compressible X-shaped protrusions (832) extending upwardly from a planar base in the form of a web (833) having an elongate rectangular shape such that X-shaped protrusions (832) are integrally connected with one another in a plurality of linear arrays defining a grid structure atop web (833). In the present example, adjunct (830) includes two lateral adjunct sections (830a, 830b) configured for placement on respective sides of staple cartridge slot (806), each including an axial row of X-shaped protrusions (832) extending in a proximal-distal direction. It will be appreciated that adjunct (830) of other versions may have various other quantities and configurations of X-shaped protrusions (832). In the example shown, lateral adjunct sections (830a, 830b) are coupled to each other by a portion of web (833) extending therebetween. Web (833) may be configured to be severed by cutting edge (62) of firing member (60) during translation thereof through staple cartridge slot (806) to separate lateral adjunct sections (830a, 830b) from each other.

Each X-shaped protrusion (832) of adjunct (830) is symmetrical about a first vertical plane that extends through a central crossing point of X-shaped protrusion (832) and parallel to the sidewalls of staple cartridge slot (806); and at least some X-shaped protrusions (832) are also symmetrical about a second vertical plane that extends through the central crossing point of X-shaped protrusion (832) and transversely to the length of staple cartridge slot (806). Each X-shaped protrusion (832) of the present example has a hollow interior and includes four elongate ridges (834a, 834b, 834c, 834d) each having a pair of walls (835) converging toward a respective closed upper end (836), with ridges (834a, 834b, 834c, 834d) intersecting each other at the crossing point of X-shaped protrusion (832) to define the symmetrical geometrical configuration described above. More specifically, each X-shaped protrusion (832) includes a proximal, laterally-inner ridge (834a) and a distal, laterally-outer ridge (834b) aligned coaxially along a horizontal first axis (A1), which extends obliquely relative to the length of staple cartridge slot (806); and a proximal, laterally-outer ridge (834c) and a distal, laterally-inner ridge (834d) aligned coaxially along a horizontal second axis (A2), which also extends obliquely relative to the length of staple cartridge slot (806), where each axis (A1, A2) extends through the crossing point. In the example shown, a respective rounded pylon (837) is positioned at a terminus of each ridge (834a, 834b, 834c, 834d) opposite the crossing point of the corresponding X-shaped protrusion (832). In some versions, walls (835), upper ends (836), and/or web (833) may have a substantially uniform thickness for supporting biocompatibility of adjunct (830) by promoting uniform degrading of walls (835), upper ends (836) and/or web (833). For example, each wall (835), upper end (836), and/or web (833) may have a thickness of about 0.2 mm. In addition, or alternatively, ridges (834a, 834b, 834c, 834d) and/or pylons (837) may have a substantially uniform height relative to a bottom surface of web (833). For example, each ridge (834a, 834b) and/or pylon (837) may have a height of about 2.25 mm relative to a bottom surface of web (833). In some versions, the ratio of the overall height of adjunct (830) to the thickness(es) of walls (835) and/or pylons (837) may be between about 4:1 and about 8:1.

As shown, each X-shaped protrusion (832) is interconnected with one or two longitudinally-adjacent X-shaped protrusion(s) (832), via the respective pylons (837) directly interfacing with each other. In the example shown, inner ridges (834a, 834d) of one lateral adjunct section (830a) are coupled to adjacent inner ridges (834a, 834d) of the other lateral adjunct section (830b) by web (833). Adjunct (830) may be formed of an elastic, bioabsorbable polymeric (e.g., elastomeric) material having a suitable degree of elasticity that enables adjunct (830) to compress and resiliently resume its original shape. In the present example, each X-shaped protrusion (832) of adjunct (830) is resiliently compressible in such a manner in at least the proximal-distal, transverse, and vertical directions. Additionally, adjunct (830) may be formed as a unitary (e.g., monolithic) structure via a thermoforming and/or vacuum-forming process, for example.

In this regard, the lower portions of the walls (835) of each X-shaped protrusion (832) opposite the corresponding upper end (836) intersect with web (833) to collectively define an open lower end (838) of the respective X-shaped protrusion (832) at a stapler-engaging face of adjunct (830). Lower ends (838) of each X-shaped protrusion (832) are devoid of any undercuts (e.g., internal undercuts, occluded undercuts, etc.) or other geometrical features extending under the hollow interior of the respective X-shaped protrusion (832) such that each hollow interior opens uninterruptedly to the respective lower end (838) (e.g., without constricting inwardly). In some versions, each lower end (838) may have an inner cross dimension greater than or equal to each inner cross dimension of the respective hollow interior. Adjunct (830) may have at least one undulating cross-sectional side and/or end profile, such as with upper ends (836) defining peaks of the undulating cross-sectional side and/or end profile and with web (833) defining valleys of the undulating cross-sectional side and/or end profile.

It will be appreciated that the absence of undercuts or other geometrical features extending under the hollow interiors of X-shaped protrusions (832) at lower ends (838) may enable thermoforming and/or vacuum forming of adjunct (830), since the presence of such undercuts or other geometrical features might otherwise interfere with the ability of adjunct (830) to be formed from a sheet of heated material stretched over a mold and/or forced thereagainst by a vacuum. More particularly, a single mold (not shown) may include a single mold surface configured to produce both the internal and external features of adjunct (830) on such a heated sheet of material stretched thereover and/or forced thereagainst by a vacuum. Due to the absence of undercuts or other geometrical features extending under the hollow interiors of X-shaped protrusions (832) at lower ends (838), such a single mold may be capable of fully forming the internal and external features of adjunct (830) without additional forming steps.

As shown, the walls (835) of each X-shaped protrusion (832) taper and/or curve outwardly from the respective upper end (836) toward the respective lower end (838) (e.g., to web (833)) at one or more corresponding positive draft angles (e.g., relative to a vertical plane perpendicular to web (833)) for assisting with separation of adjunct (830) from the mold after thermoforming adjunct (830) thereover. Likewise, the hollow interior of each X-shaped protrusion (832) tapers and/or curves outwardly from an upper end of the hollow interior toward the respective lower end (838) at one or more corresponding positive draft angles (e.g., relative to a vertical plane perpendicular to web (833)) for assisting with separation of the mold halves after injection molding adjunct (830) therein.

As shown in FIG. 24, each X-shaped protrusion (832) of adjunct (830) is configured to partially overlie a plurality of corresponding recesses (812, 814, 816) and/or a plurality of corresponding staple openings (808) of staple cartridge (800). More particularly, the crossing point of each X-shaped protrusion (832) is configured to overlie a longitudinally-central region of a corresponding diamond-shaped recess (816) and of a corresponding staple opening (808), and the portions of each X-shaped protrusion (832) at or near the respective pylons (837) are each configured to overlie a longitudinally-central region of a corresponding triangular recess (812, 814) and of a corresponding staple opening (808). In some versions, the bottom surface of web (833) is configured to rest on deck (804), and the tips of the legs of each staple are configured to protrude upwardly out of the corresponding staple openings (808) at least slightly above deck (804) and pierce web (833) prior to deployment of the staples to assist with retaining adjunct (330) on deck (804) and/or to promote such partial overlying of X-shaped protrusions (832) over the corresponding recess (812, 814, 816).

In any event, such partial overlying of X-shaped protrusions (832) relative to the corresponding recesses (812, 814, 816) may enable the legs of each staple (not shown) slidably housed within the respective staple opening (808) to flank a portion of one or more corresponding X-shaped protrusions (832) during deployment of the staples. More particularly, the legs of each staple slidably housed within a corresponding diamond-shaped recess (816) may flank the crossing point of the corresponding X-shaped protrusion (832), and the legs of each staple slidably housed within a corresponding triangular recess (812, 814) may flank the portion(s) of one or more corresponding X-shaped protrusions (832) at or near the respective pylons (837). In this manner, the deformed legs of each staple to capture and compress the corresponding X-shaped protrusion(s) (832) against the crown thereof when the staples are formed by staple forming pockets (58) of anvil (56). Such flanking of X-shaped protrusions (832) by the legs of the corresponding staples may also enable at least some staples to avoid piercing the corresponding X-shaped protrusion(s) (832) during deployment of the staples. It will also be appreciated that upper ends (836) of X-shaped protrusions (832) may engage and apply pressure to the stapled tissue to thereby assist with compressing the stapled tissue. In some versions, adjunct (830) may be configured to provide a stress plateau when compressed for optimally compressing the stapled tissue over a predefined range of tissue thicknesses.

Figure 25:
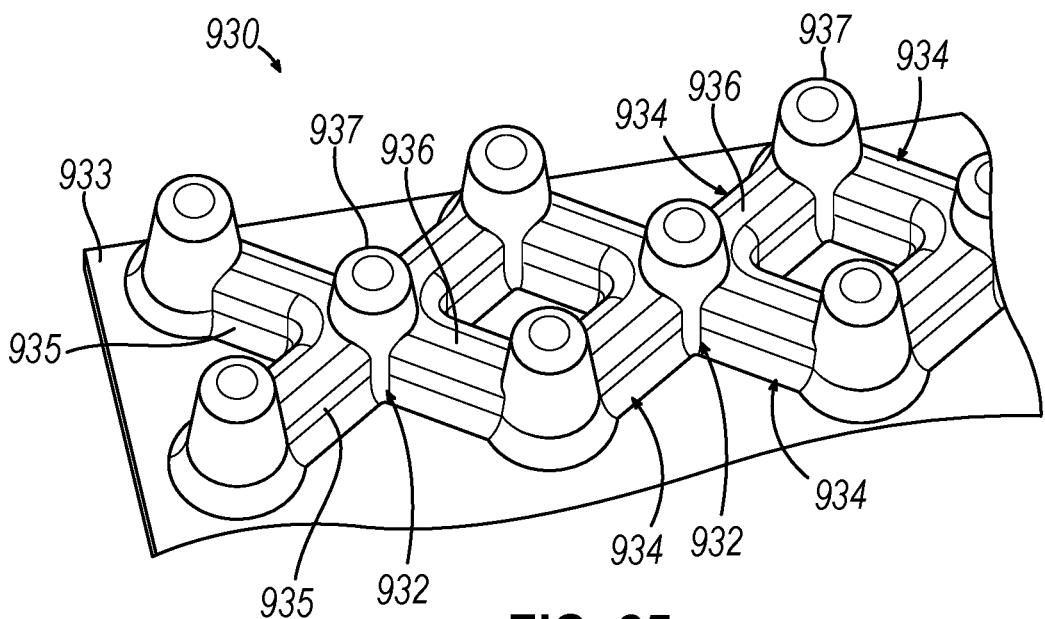
FIG. 25 depicts a partial top perspective view of another alternative exemplary adjunct that is thermoformable and has X-shaped protrusions configured to be flanked by the legs of staples deployed from the staple cartridge, and that further has pylons protruding upwardly beyond the X-shaped protrusions.

G. Second Exemplary Thermoformable Adjunct with X-Shaped Protrusions Configured to be Flanked by Staple Legs FIG. 25 shows another exemplary compressible unitary (e.g., monolithic) adjunct (930) configured for releasable attachment to a staple cartridge (not shown) similar to staple cartridge (800). Adjunct (930) is configured for use with end effector (50) and is similar to adjunct (830) described above except as otherwise described below. In this regard, adjunct (930) has a plurality of three-dimensional, resiliently compressible X-shaped protrusions (932) extending upwardly from a planar base in the form of a web (933) having an elongate rectangular shape such that X-shaped protrusions (932) are integrally connected with one another in at least one linear array defining a grid structure atop web (933). In the present example, adjunct (930) includes at least one axial row of X-shaped protrusions (932) in a manner similar to that described above in connection with FIGS. 22-24.

Each X-shaped protrusion (932) of the present example has a hollow interior and includes four elongate ridges (934) each having a pair of walls (935) converging toward a respective closed upper end (936), with ridges (934) intersecting each other at a crossing point of X-shaped protrusion (932). In the example shown, a respective rounded pylon (937) is positioned at the crossing point of each X-shaped protrusion (932) and at a terminus of each ridge (934) opposite the crossing point of the corresponding X-shaped protrusion (932). The illustrated ridges (934) have a substantially uniform first height relative to web (933), and the illustrated pylons (937) have a substantially uniform second height relative to web (933) greater than the first height, such that pylons (937) protrude upwardly beyond X-shaped protrusions (932).

As shown, each X-shaped protrusion (932) is interconnected with one or two longitudinally-adjacent X-shaped protrusion(s) (932), in manners similar to those described above in connection with FIGS. 22-24.

The lower portions of the walls (935) of each X-shaped protrusion (932) opposite the corresponding upper end (936) intersect with web (933) to collectively define an open lower end (not shown) of the respective X-shaped protrusion (932) at a stapler-engaging face of adjunct (930). Lower ends of each X-shaped protrusion (932) are devoid of any undercuts (e.g., internal undercuts, occluded undercuts, etc.) or other geometrical features extending under the hollow interior of the respective X-shaped protrusion (932) such that each hollow interior opens uninterruptedly to the respective lower end to enable thermoforming and/or vacuum forming of adjunct (930), in a manner similar to that described above in connection with FIGS. 22-24. Adjunct (930) may have at least one undulating cross-sectional side and/or end profile, such as with upper ends (936) and/or pylons (937) defining peaks of the undulating cross-sectional side and/or end profile and with web (933) defining valleys of the undulating cross-sectional side and/or end profile.

Each X-shaped protrusion (932) of adjunct (930) is configured to partially overlie a plurality of corresponding recesses (912, 914, 916) and/or a plurality of corresponding staple openings (908) of staple cartridge (900) to enable the legs of each staple (not shown) slidably housed within the respective staple opening (908) to flank a portion of one or more corresponding X-shaped protrusions (932) during deployment of the staples, in a manner similar to that described above in connection with FIGS. 22-24. It will also be appreciated that upper ends (936) of X-shaped protrusions (932) and/or pylons (937) may engage and apply pressure to the stapled tissue to thereby assist with compressing the stapled tissue. In some versions, adjunct (930) may be configured to provide a stress plateau when compressed for optimally compressing the stapled tissue over a predefined range of tissue thicknesses.

H. First Exemplary Laminable Adjunct

Figure 26:
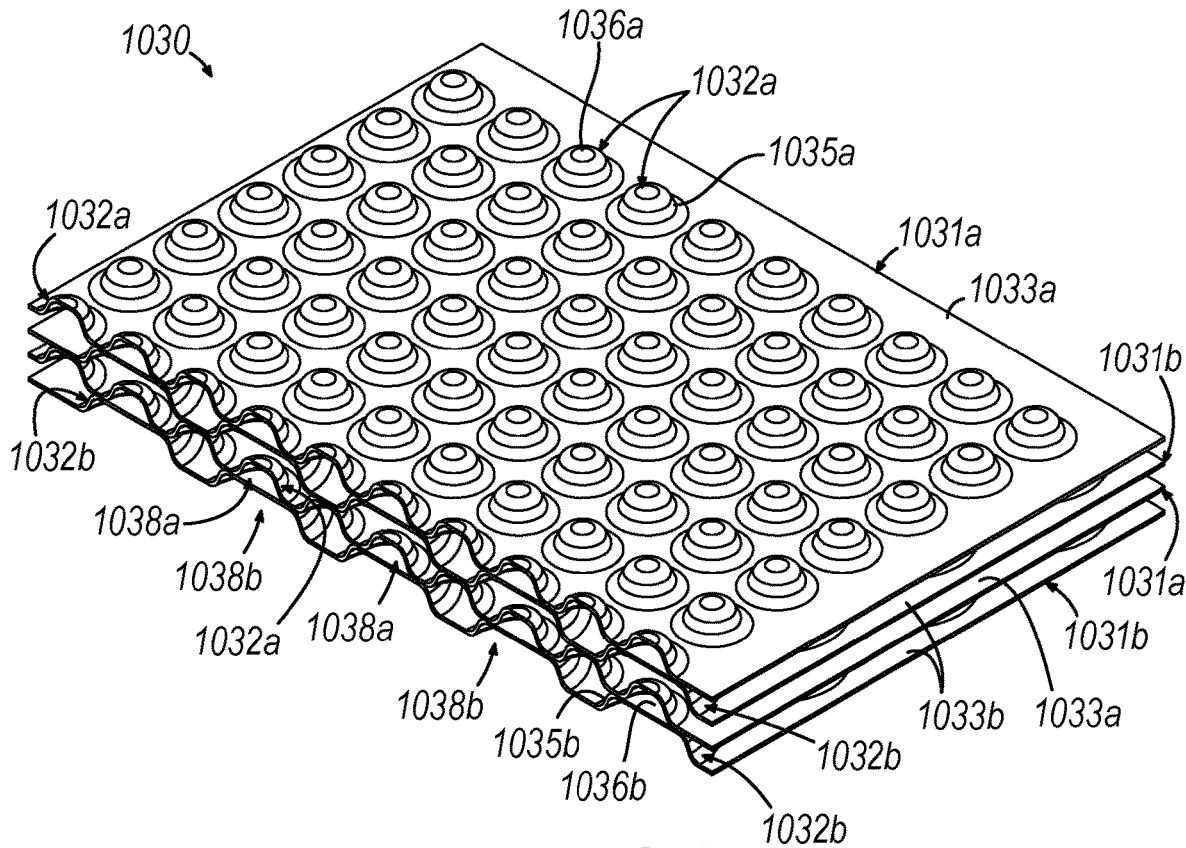
FIG. 26 depicts a partial top perspective view of another alternative exemplary adjunct that is laminable and has a plurality of layers each having bubble-shaped protrusions, the bubble-shaped protrusions including narrow bubble-shaped protrusions and wide bubble-shaped protrusions.
Figure 27:
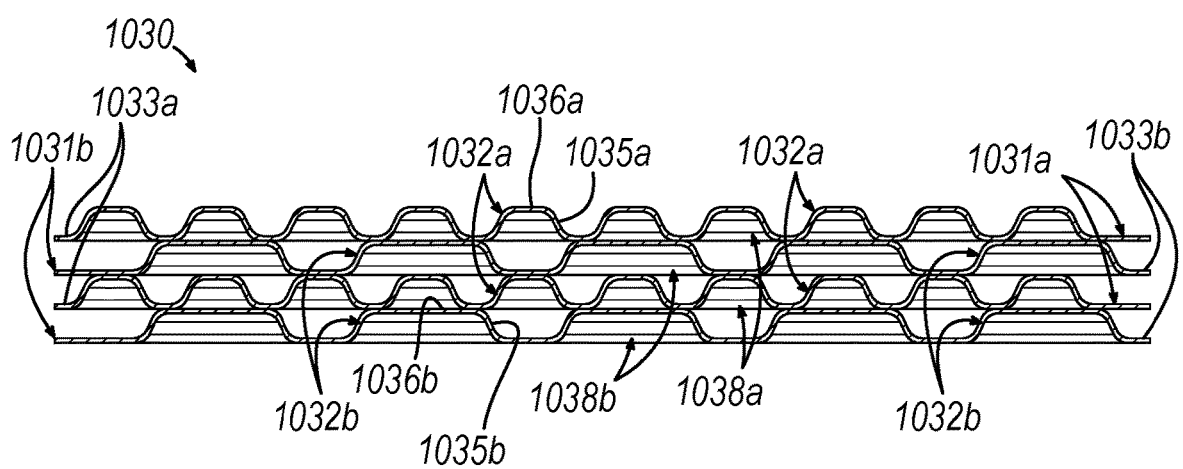
FIG. 27 depicts a cross-sectional view of the adjunct of FIG. 26.

FIGS. 26-27 show another exemplary compressible adjunct (1030) configured for releasable attachment to a staple cartridge (not shown) similar to staple cartridge (200). Adjunct (1030) is configured for use with end effector (50) and is similar to adjunct (230) described above except as otherwise described below. In this regard, adjunct (1030) has at least two stacked layers (1031*a*, 1031*b*) each having a plurality of respective three-dimensional, resiliently compressible bubble-shaped protrusions (1032*a*, 1032*b*) extending upwardly from a respective planar base in the form of a web (1033*a*, 1033*b*) having an elongate rectangular shape such that bubble-shaped protrusions (1032a, 1032b) are integrally connected with one another in a plurality of linear arrays defining a grid structure atop the respective web (1033a, 1033b). In the example shown, adjunct (1030) includes at least one first layer (1031a) and at least one second layer (1031b) having a different configuration from that of the at least one first layer (1031a). More particularly, adjunct (1030) includes a pair of first layers (1031a) having narrow bubble-shaped protrusions (1032a) and a pair of second layers (1031b) having wide bubble-shaped protrusions (1032b), with the first and second layers (1031a, 1031b) arranged in an alternating stacked configuration such that adjunct (1030) has four layers (1031a, 1031b). In some versions, adjunct (1030) may include two lateral adjunct sections (not shown) configured for placement on respective sides of the staple cartridge slot, with the corresponding layers (1031a, 1031b) each including a plurality of axial rows of the respective bubble-shaped protrusions (1032a, 1032b) extending in a proximal-distal direction, and a plurality of transverse rows of the respective bubble-shaped protrusions (1032a, 1032b) each extending in a direction transverse to a length of the staple cartridge. It will be appreciated that adjunct (1030) of other versions may have various other quantities and configurations of bubble-shaped protrusions (1032a, 1032b) and/or layers (1031a, 1031b). In some versions, the lateral adjunct sections may be coupled to each other by a portion of each web (1033a, 1033b) extending therebetween. Webs (1033a, 1033b) may be configured to be severed by cutting edge (62) of firing member (60) during translation thereof through the staple cartridge slot to separate such lateral adjunct sections from each other.

Each bubble-shaped protrusion (1032a, 1032b) of adjunct (1030) is symmetrical about a pair of planes (not shown) that extend through a centroid of bubble-shaped protrusion (1032a, 1032b), including: a first vertical plane that extends parallel to the sidewalls of the staple cartridge slot; and a second vertical plane that extends transversely to the length of the staple cartridge slot. Each bubble-shaped protrusion (1032a, 1032b) of the present example has a hollow interior and has a generally dome-shaped sidewall (1035a, 1035b) terminating at a respective closed upper end (1036a, 1036b) to define the symmetrical geometrical configuration described above. In some versions, walls (1035a, 1035b), upper ends (1036a, 1036b), and/or webs (1033a, 1033b) may have a substantially uniform thickness for supporting biocompatibility of adjunct (1030) by promoting uniform degrading of walls (1035a, 1035b), upper ends (1036a, 1036b), and/or webs (1033a, 1033b). For example, each wall (1035a, 1035b), upper end (1036a, 1036b), and/or web (1033a, 1033b) may have a thickness of about 0.0015 inch. In addition, or alternatively, bubble-shaped protrusions (1032a, 1032b) may have a substantially uniform height relative to a bottom surface of the respective web (1033a, 1033b). In some versions, the overall height of adjunct (1030) may be between about 1 mm and about 4 mm.

As shown, each bubble-shaped protrusion (1032a, 1032b) is interconnected with one or two longitudinally-adjacent bubble-shaped protrusion(s) (1032a, 1032b) and with one or two laterally-adjacent bubble-shaped protrusion(s) (1032a, 1032b) by the respective web (1033a, 1033b). Adjunct (1030) may be formed of an elastic, bioabsorbable polymeric (e.g., elastomeric) material having a suitable degree of elasticity that enables adjunct (1030) to compress and resiliently resume its original shape. In the present example, each bubble-shaped protrusion (1032a, 1032b) of adjunct (1030) is resiliently compressible in such a manner in at least the proximal-distal, transverse, and vertical directions. Additionally, each layer (1031a, 1031b) of adjunct (1030) may be formed as a unitary (e.g., monolithic) structure via a thermoforming, vacuum forming, and/or injection molding process, for example, and adjunct (1030) may be formed as a laminated structure via a laminating process, for example.

In this regard, the lower portions of the walls (1035a, 1035b) of each bubble-shaped protrusion (1032a, 1032b) opposite the corresponding upper end (1036a, 1036b) intersect with the respective web (1033a, 1033b) to collectively define an open lower end (1038a, 1038b) of the respective bubble-shaped protrusion (1032a, 1032b). Lower ends (1038a, 1038b) of each bubble-shaped protrusion (1032a, 1032b) are devoid of any undercuts (e.g., internal undercuts, occluded undercuts, etc.) or other geometrical features extending under the hollow interior of the respective bubble-shaped protrusion (1032a, 1032b) such that each hollow interior opens uninterruptedly to the respective lower end (1038a, 1038b) (e.g., without constricting inwardly). In some versions, each lower end (1038a, 1038b) may have an inner cross dimension greater than or equal to each inner cross dimension of the respective hollow interior. Each layer (1031a, 1031b) of adjunct (1030) may have at least one undulating cross-sectional side and/or end profile, such as with the respective upper ends (1036a, 1036b) defining peaks of the undulating cross-sectional side and/or end profile and with the respective web (1033a, 1033b) defining valleys of the undulating cross-sectional side and/or end profile. In the example shown, bubble-shaped protrusions (1032a, 1032b) of each layer (1031a, 1031b) are equally sized and equally spaced apart from each other along their respective rows, such that the undulating cross-sectional side and/or end profile(s) may be periodic.

It will be appreciated that the absence of undercuts or other geometrical features extending under the hollow interiors of bubble-shaped protrusions (1032a, 1032b) at lower ends (1038a, 1038b) may enable thermoforming and/or vacuum forming of each layer (1031a, 1031b) of adjunct (1030), since the presence of such undercuts or other geometrical features might otherwise interfere with the ability of each layer (1031a, 1031b) of adjunct (1030) to be formed from a sheet of heated material stretched over a mold and/or forced thereagainst by a vacuum. More particularly, a single mold (not shown) may include a single mold surface configured to produce both the internal and external features of a respective layer (1031a, 1031b) of adjunct (1030) on such a heated sheet of material stretched thereover and/or forced thereagainst by a vacuum. Due to the absence of undercuts or other geometrical features extending under the hollow interiors of bubble-shaped protrusion (1032a, 1032b) at lower ends (1038a, 1038b), such a single mold may be capable of fully forming the internal and external features of the respective layer (1031a, 1031b) of adjunct (1030) without additional forming steps.

It will also be appreciated that the absence of undercuts or other geometrical features extending under the hollow interiors of bubble-shaped protrusions (1032a, 1032b) at lower ends (1038a, 1038b) may enable injection molding of each layer (1031a, 1031b) of adjunct (1030), since the presence of such undercuts or other geometrical features might otherwise interfere with the ability of two mold halves to be separated (e.g., opened) after injection molding a respective layer (1031a, 1031b) of adjunct (1030) therein. More particularly, a first mold half (not shown) may include a cavity configured to receive molten material for producing the external features of the respective layer (1031a, 1031b) of adjunct (1030) while a second mold half (not shown) may include a core configured to extend into the cavity for producing the internal features of the respective layer (1031a, 1031b) of adjunct (1030). Due to the absence of undercuts or other geometrical features extending under the hollow interiors of bubble-shaped protrusions (1032a, 1032b) at lower ends (1038a, 1038b), such first and second mold halves may be readily separated from each other (e.g., along a horizontal parting line) after injection molding the respective layer (1031a, 1031b) of adjunct (1030) therein without disrupting the structural integrity of the respective layer (1031a, 1031b) of adjunct (1030) or of either mold half.

As shown, the walls (1035a, 1035b) of each bubble-shaped protrusion (1032a, 1032b) taper and/or curve outwardly from the respective upper end (1036a, 1036b) toward the respective lower end (1038a, 1038b) (e.g., to the respective web (1033a, 1033b) at one or more corresponding positive draft angles (e.g., relative to a vertical plane perpendicular to the respective web (1033a, 1033b) and/or perpendicular to the horizontal parting line of the mold halves) for assisting with separation of each layer (1031a, 1031b) of adjunct (1030) from the respective mold after thermoforming the respective layer (1031a, 1031b) of adjunct (1030) thereover and/or for assisting with separation of the mold halves after injection molding a respective layer (1031a, 1031b) of adjunct (1030) therein. Likewise, the hollow interior of each bubble-shaped protrusion (1032a, 1032b) tapers and/or curves outwardly from an upper end of the hollow interior toward the respective lower end (1038a, 1038b) at one or more corresponding positive draft angles (e.g., relative to a vertical plane perpendicular to the respective web (1033a, 1033b) and/or perpendicular to the horizontal parting line of the mold halves) for assisting with separation of each layer (1031a, 1031b) of adjunct (1030) from the respective mold after thermoforming the respective layer (1031a, 1031b) of adjunct (1030) thereover and/or for assisting with separation of the mold halves after injection molding a respective layer (1031a, 1031b) of adjunct (1030) therein.

Layers (1031a, 1031b) may be secured to each other in any suitable manner. For example, layers (1031a, 1031b) may be glued to each other via an adhesive material, such as a buttress adhesive material. In addition, or alternatively, layers (1031a, 1031b) may be secured to each other via any suitable bonding technique(s), such as any one or more of thermal bonding, chemical bonding, and/or mechanical bonding techniques. In some versions, layers (1031a, 1031b) may initially be laminated together in large sheets, which may then be cut to form one or more adjuncts (1030).

As shown in FIG. 27, each narrow bubble-shaped protrusion (1032a) of the upper first layer (1031a) overlies a corresponding narrow bubble-shaped protrusion (1032a) of the lower first layer (1031a), and each wide bubble-shaped protrusion (1032b) of the upper second layer (1031b) overlies a corresponding wide bubble-shaped protrusion (1032b) of the upper second layer (1031b). At least some narrow bubble-shaped protrusions (1032a) of each first layer (1031a) overlie corresponding wide bubble-shaped protrusions (1032b) of each second layer (1031b), while at least some other narrow bubble-shaped protrusions (1032a) of each first layer (1031a) overlie the space between a corresponding pair of adjacent wide bubble-shaped protrusions (1032b) of each second layer (1031b). For example, narrow bubble-shaped protrusions (1032a) may alternate (e.g., longitudinally and/or laterally) between overlying corresponding wide bubble-shaped protrusions (1032b) and overlying the space between a corresponding pair of adjacent wide bubble-shaped protrusions (1032b). Likewise, at least some wide bubble-shaped protrusions (1032b) overlie corresponding narrow bubble-shaped protrusions (1032a). For example, each wide bubble-shaped protrusion (1032b) of the second layer (1031b) sandwiched between first layers (1031a) may overlie corresponding narrow bubble-shaped protrusions (1032a) of the first layer (1031a) sandwiched between second layers (1031b). In this manner, layers (1031a, 1031b) may be configured to collapse together to define a substantially flat state of adjunct (1030). More particularly, at least some narrow bubble-shaped protrusions (1032a) may collapse into the underlying space between the corresponding pair of adjacent wide bubble-shaped protrusions (1032b), and at least some wide bubble-shaped protrusions (1032b) may collapse into the space between the underlying corresponding narrow bubble-shaped protrusions (1032a) and the adjacent narrow bubble-shaped protrusions (1032a). In some versions, layers (1031a, 1031b) may be configured to provide adjunct (1030) with a predetermined minimum crush height when adjunct (1030) is in the flat state. In addition, or alternatively, each first layer (1031a) may be configured to compress to a first percentage of the uncompressed height of each first layer (1031a) during compression of adjunct (1030), while each second layer (1031b) may be configured to compress to a second percentage of the uncompressed height of each second layer (1031b) different from the first percentage during compression of adjunct (1030). For example, each first layer (1031a) may have a first stiffness, and each second layer (1031b) may have a second stiffness different from the first stiffness.

At least some bubble-shaped protrusions (1032a, 1032b) (e.g., at least some narrow bubble-shaped protrusions (1032a) and/or at least some wide bubble-shaped protrusions (1032b)) of adjunct (1030) may be configured to overlie a corresponding staple cartridge recess, similar to recesses (212, 214, 216), and/or a corresponding staple opening, similar to staple openings (208), of the staple cartridge. In some versions, the bottom surface of the respective web (1033a, 1033b) of the bottom layer (1031a, 1031b) (e.g., the bottom surface of web (1033b) of the lowermost second layer (1031b)) may be configured to rest on the staple cartridge deck, and the tips of the legs of each staple may be configured to protrude upwardly out of the corresponding staple openings at least slightly above the staple cartridge deck and pierce the respective web (1033a, 1033b) of the bottom layer (1031a, 1031b) prior to deployment of the staples to assist with retaining adjunct (1030) on the staple cartridge deck and/or to promote such overlying of at least some bubble-shaped protrusions (1032a, 1032b) over the corresponding staple cartridge recess.

In any event, such overlying of at least some bubble-shaped protrusions (1032a, 1032b) relative to the corresponding staple cartridge recesses may enable the legs of each staple (not shown) slidably housed within the respective staple opening to flank the corresponding bubble-shaped protrusion (1032a, 1032b) during deployment of the staples. In this manner, the deformed legs of each staple may capture and compress the corresponding bubble-shaped protrusion (1032a, 1032b) against the crown thereof when the staples are formed by staple forming pockets (58) of anvil (56). Such flanking of at least some bubble-shaped protrusions (1032a, 1032b) by the legs of the corresponding staples may also enable at least some staples to avoid piercing the corresponding bubble-shaped protrusions (1032a, 1032b) during deployment of the staples. It will also be appreciated that upper ends (1036a, 1036b) of bubble-shaped protrusions (1032a, 1032b) of the top layer (1031a, 1031b) (e.g., upper ends (1036a) of bubble-shaped protrusions (1032a) of the uppermost first layer (1031a)) may engage and apply pressure to the stapled tissue to thereby assist with compressing the stapled tissue. In some versions, adjunct (1030) may be configured to provide a stress plateau when compressed for optimally compressing the stapled tissue over a predefined range of tissue thicknesses.

Second Exemplary Laminable Adjunct

Figure 28:
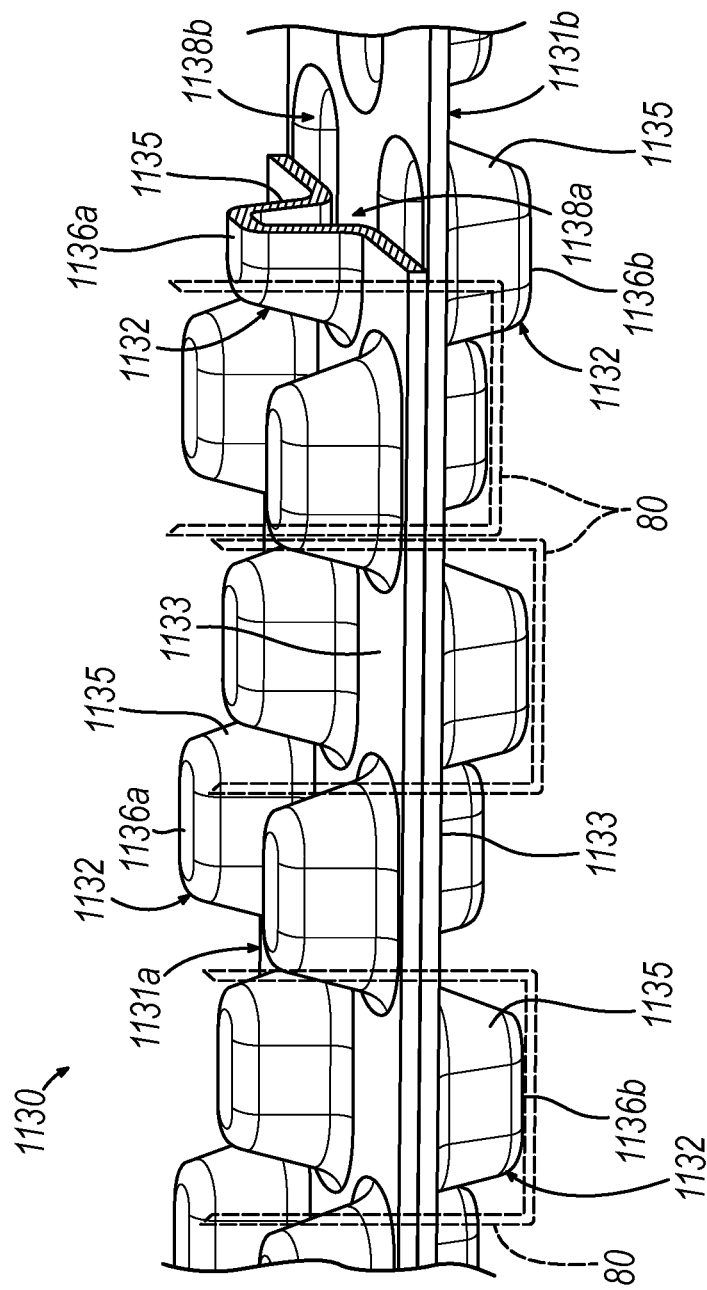
FIG. 28 depicts a partial top perspective view of another alternative exemplary adjunct that is laminable and has a plurality of layers each having bubble-shaped protrusions, the bubble-shaped protrusions having a generally uniform configuration, schematically showing the flanking of the bubble-shaped protrusions of the adjunct by the legs of staples deployed from a staple cartridge.

FIG. 28 shows another exemplary compressible adjunct (1130) configured for releasable attachment to a staple cartridge (not shown) similar to staple cartridge (200). Adjunct (1130) is configured for use with end effector (50) and is similar to adjunct (1030) described above except as otherwise described below. In this regard, adjunct (1130) has at least two stacked layers (1131a, 1131b) each having a plurality of respective three-dimensional, resiliently compressible bubble-shaped protrusions (1132) extending outwardly from a respective planar base in the form of a web (1133) having an elongate rectangular shape such that bubble-shaped protrusions (1132) are integrally connected with one another in a plurality of linear arrays defining a grid structure atop or under the respective web (1133). In the example shown, adjunct (1130) includes at least one first layer (1131a) and at least one second layer (1131b) having a same configuration as that of the at least one first layer (1131a) and oriented in an opposing direction as that of the at least one first layer (1131a). More particularly, adjunct (1130) includes a single first layer (1131a) having bubble-shaped protrusions (1132) extending upwardly from the respective web (1133) and a single second layer (1131b) having bubble-shaped protrusions (1132) extending downwardly from the respective web (1133), such that adjunct (1130) has two layers (1131a, 1131b). In the present example, each layer (1131a, 1131b) of adjunct (1130) includes and outer axial rows of bubble-shaped protrusions (1132) each extending in a proximal-distal direction, and a plurality of transverse rows of bubble-shaped protrusions (1132) each extending in a direction transverse to a length of the staple cartridge. In the example shown, each layer (1131a, 1131b) of adjunct (1130) also includes a medial axial row of bubble-shaped protrusions (1132) extending in the proximal-distal direction and offset from each of the inner and outer axial rows of bubble-shaped protrusions (1132) in the proximal-distal direction.

Each bubble-shaped protrusion (1132) of first layer (1131a) of the present example has a hollow interior and a generally elongate dome-shaped sidewall (1135) terminating at a respective closed upper end (1136a), while each bubble-shaped protrusion (1132) of second layer (1131b) of the present example similarly has a hollow interior and a generally elongate dome-shaped sidewall (1135) terminating at a respective closed lower end (1136b). In some versions, walls (1135), upper and lower ends (1136a, 1136b), and/or webs (1133) may have a substantially uniform thickness for supporting biocompatibility of adjunct (1230) by promoting uniform degrading of walls (1135), upper and lower ends (1136a, 1136b), and/or webs (1133). For example, each wall (1135), upper and lower end (1136a, 1136b), and/or web (1133) may have a thickness of about 0.0015 inch. In addition, or alternatively, bubble-shaped protrusions (1132) may have a substantially uniform height relative to a bottom surface of the respective web (1133). In some versions, the overall height of adjunct (1130) may be between about 1 mm and about 4 mm.

As shown, each inner and outer bubble-shaped protrusion (1132) is interconnected with one or two laterally-adjacent medial bubble-shaped protrusion(s) (1132) and with one or two longitudinally-adjacent inner or outer bubble-shaped protrusion(s) (1132), and each medial bubble-shaped protrusion (1132) is interconnected with one or two laterally-adjacent inner bubble-shaped protrusion(s) (1132), with one or two laterally-adjacent outer bubble-shaped protrusion(s) (1132), and with one or two longitudinally-adjacent medial bubble-shaped protrusion(s) (1132), in manners similar to those described above in connection with FIGS. 26-27.

The lower portions of the walls (1135) of each bubble-shaped protrusion (1132) of first layer (1131a) opposite the corresponding upper end (1136a) intersect with the respective web (1133) to collectively define an open lower end (1138a) of the respective bubble-shaped protrusion (1132). Lower ends (1138a) of each bubble-shaped protrusion (1132) of first layer (1131a) are devoid of any undercuts (e.g., internal undercuts, occluded undercuts, etc.) or other geometrical features extending under the hollow interior of the respective bubble-shaped protrusion (1132) such that each hollow interior opens uninterruptedly to the respective lower end (1138a) to enable thermoforming, vacuum forming, and/or injection molding of first layer (1131a) of adjunct (1130), in a manner similar to that described above in connection with FIGS. 26-27. Likewise, the upper portions of the walls (1135) of each bubble-shaped protrusion (1132) of second layer (1131b) opposite the corresponding lower end (1136b) intersect with the respective web (1133) to collectively define an open upper end (1138b) of the respective bubble-shaped protrusion (1132). Upper ends (1138b) of each bubble-shaped protrusion (1132) of second layer (1131b) are devoid of any undercuts (e.g., internal undercuts, occluded undercuts, etc.) or other geometrical features extending over the hollow interior of the respective bubble-shaped protrusion (1132) such that each hollow interior opens uninterruptedly to the respective upper end (1138b) to enable thermoforming, vacuum forming, and/or injection molding of second layer (1131b) of adjunct (1130), in a manner similar to that described above in connection with FIGS. 26-27.

First layer (1131a) of adjunct (1130) may have at least one undulating cross-sectional side and/or end profile, such as with upper ends (1136a) defining peaks of the undulating cross-sectional side and/or end profile and with the respective web (1133) defining valleys of the undulating cross-sectional side and/or end profile. Likewise, second layer (1131b) of adjunct (1130) may have at least one undulating cross-sectional side and/or end profile, such as with the respective web (1133) defining peaks of the undulating cross-sectional side and/or end profile and with lower ends (1136b) defining valleys of the undulating cross-sectional side and/or end profile. In the example shown, bubble-shaped protrusions (1132) of each layer (1131a, 1131b) are equally sized and equally spaced apart from each other along their respective rows, such that the undulating cross-sectional side and/or end profile(s) may be periodic. Layers (1131a, 1131b) may be secured to each other in any suitable manner, such as any of those described above in connection with FIGS. 26-27.

As shown in FIG. 28, each bubble-shaped protrusion (1132) of first layer (1131a) overlies the space between a corresponding pair of adjacent bubble-shaped protrusions (1132) of second layer (1131b), while the space between each pair of adjacent bubble-shaped protrusions (1132) of first layer (1131a) overlies a corresponding bubble-shaped protrusion (1132) of second layer (1131b). In this manner, each bubble-shaped protrusion (1132) of first layer (1131a) may be offset from each bubble-shaped protrusion (1132) of second layer (1131b) in the vertical direction.

At least some bubble-shaped protrusions (1132) (e.g., at least some bubble-shaped protrusions (1132) of first layer (1131a) and/or at least some bubble-shaped protrusions (1132) of second layer (1131b)) of adjunct (1130) may be configured to overlie a corresponding staple cartridge recess, similar to recesses (212, 214, 216), and/or a corresponding staple opening, similar to staple openings (208), of the staple cartridge to enable the legs of each staple (80) slidably housed within the respective staple opening to flank the corresponding bubble-shaped protrusion (1132) during deployment of staples (80), in a manner similar to that described above in connection with FIGS. 26-27. It will also be appreciated that upper ends (1136a) of bubble-shaped protrusions (1132) of first layer (1131a) may engage and apply pressure to the stapled tissue to thereby assist with compressing the stapled tissue. In some versions, adjunct (1130) may be configured to provide a stress plateau when compressed for optimally compressing the stapled tissue over a predefined range of tissue thicknesses.

J. First Exemplary Extrudable Adjunct

Figure 29:
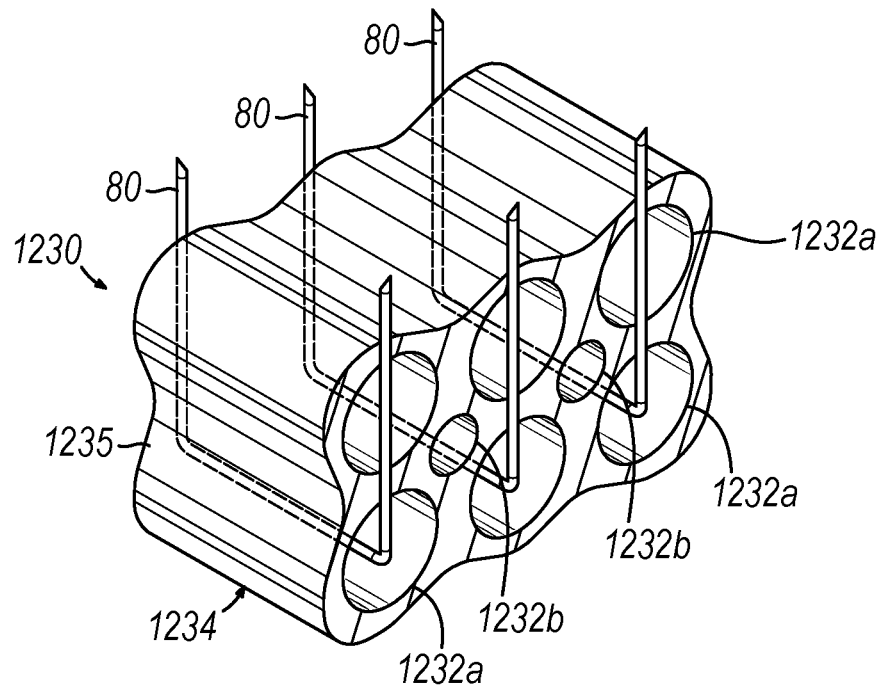
FIG. 29 depicts a partial top perspective view of another alternative exemplary adjunct that is extrudable and has a plurality of circular bores extending along a length thereof, schematically showing the legs of staples deployed from a staple cartridge passing vertically through corresponding bores of the adjunct.

FIG. 29 shows another exemplary compressible unitary (e.g., monolithic) adjunct (1230) configured for releasable attachment to a staple cartridge (not shown) similar to staple cartridge (200). Adjunct (1230) is configured for use with end effector (50) and is similar to adjunct (230) described above except as otherwise described below. In this regard, adjunct (1230) has an elongate body (1234) having a contoured exterior surface (1235) such that the exterior of body (1234) has a generally undular cross-sectional profile. Adjunct (1230) also has a plurality of axial bores (1232a, 1232b) extending in a proximal-distal direction along an entire length of body (1234). More particularly, adjunct (1230) has two transverse rows of wide circular bores (1232a) each extending in a direction transverse to a length of the staple cartridge, and three vertical rows of wide circular bores (1232a) each extending in a vertical direction. In the example shown, adjunct (1230) also includes a transverse row of narrow bores (1232b) extending in a direction transverse to the length of the staple cartridge and offset from each of the transverse and vertical rows of wide bores (1232a) in the transverse and vertical directions. It will be appreciated that adjunct (1230) of other versions may have various other quantities and configurations of bores (1232a, 1232b).

Adjunct (1230) may be formed of an elastic, bioabsorbable polymeric (e.g., elastomeric) material having a suitable degree of elasticity that enables adjunct (1230) to compress and resiliently resume its original shape. In the present example, each bore (1232a, 1232b) of adjunct (1230) is resiliently collapsible in at least the transverse and vertical directions. Additionally, adjunct (1230) may be formed as a unitary (e.g., monolithic) structure via an extruding and/or drawing process, for example. In this regard, adjunct (1230) may have a substantially uniform cross-sectional shape along a length thereof. It will be appreciated that this substantially uniform cross-section may enable extruding and/or drawing of adjunct (1230). More particularly, material may be forced through a die configured to produce both the internal and external features of adjunct (1230) on such material.

As shown in FIG. 29, each wide bore (1232a) of adjunct (1230) is configured to overlie a corresponding staple cartridge recess, similar to recesses (212, 214, 216), and/or a corresponding staple opening, similar to staple openings (208), of the staple cartridge to enable the legs of each staple (80) slidably housed within the respective staple opening to pass vertically through the corresponding wide bore(s) (1232a) during deployment of staples (80) for assisting with guiding staples (80) through adjunct (1230). While not shown, an underside of body (1234) configured to confront the cartridge deck may include a series of perforations or openings (e.g., slots, channels, and/or gaps) each aligned with a respective lower wide bore (1232a) and configured to enable the crown of a respective staple (80) to pass through the underside of body (1234) and into the respective lower wide bore (1232a) with minimal resistance during deployment of staples (80). In any event, the deformed legs of each staple (80) may collapse the corresponding bore(s) (1232a, 1232b) against the crown thereof when staples (80) are formed by staple forming pockets (58) of anvil (56). It will also be appreciated that an upper portion of exterior surface (1235) may engage and apply pressure to the stapled tissue to thereby assist with compressing the stapled tissue. In some versions, adjunct (1230) may be configured to provide a stress plateau when compressed for optimally compressing the stapled tissue over a predefined range of tissue thicknesses.

K. Second Exemplary Extrudable Adjunct

Figure 30:
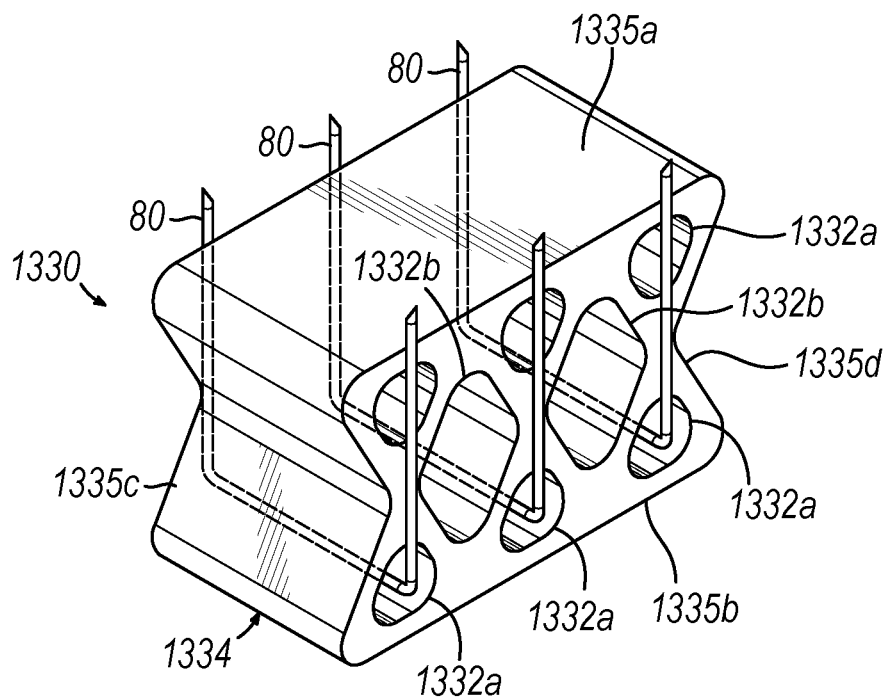
FIG. 30 depicts a partial top perspective view of another alternative exemplary adjunct that is extrudable and has a plurality of rounded triangular bores extending along a length thereof, schematically showing the legs of staples deployed from a staple cartridge passing vertically through corresponding bores of the adjunct.

FIG. 30 shows another exemplary compressible unitary (e.g., monolithic) adjunct (1330) configured for releasable attachment to a staple cartridge (not shown) similar to staple cartridge (200). Adjunct (1330) is configured for use with end effector (50) and is similar to adjunct (1230) described above except as otherwise described below. In this regard, adjunct (1330) has an elongate body (1334) having flat exterior top and bottom surfaces (1335a, 1335b) and a pair of generally V-shaped exterior side surfaces (1335c, 1335d) directed inwardly such that the exterior of body (1334) has a generally hourglass-shaped cross-sectional profile. Adjunct (1330) also has a plurality of axial bores (1332a, 1332b) extending in a proximal-distal direction along an entire length of body (1334). More particularly, adjunct (1330) has two transverse rows of rounded triangular bores (1332a) each extending in a direction transverse to a length of the staple cartridge, and three vertical rows of rounded triangular bores (1332a) each extending in a vertical direction. In the example shown, adjunct (1330) also includes a transverse row of diamond-shaped bores (1332b) extending in a direction transverse to the length of the staple cartridge and offset from each of the transverse and vertical rows of rounded triangular bores (1332a) in the transverse and vertical directions. Adjunct (1330) may have a substantially uniform cross-sectional shape along a length thereof to enable extruding and/or drawing of adjunct (1330), in a manner similar to that described above in connection with FIG. 29.

As shown in FIG. 30, each rounded triangular bore (1332a) of adjunct (1330) is configured to overlie a corresponding staple cartridge recess, similar to recesses (212, 214, 216), and/or a corresponding staple opening, similar to staple openings (208), of the staple cartridge to enable the legs of each staple (80) slidably housed within the respective staple opening to pass vertically through the corresponding rounded triangular bore(s) (1332a) during deployment of staples (80), in a manner similar to that described above in connection with FIG. 29. It will also be appreciated that at least a portion of exterior top surface (1335a) may engage and apply pressure to the stapled tissue to thereby assist with compressing the stapled tissue. In some versions, adjunct (1330) may be configured to provide a stress plateau when compressed for optimally compressing the stapled tissue over a predefined range of tissue thicknesses.

L. Third Exemplary Extrudable Adjunct

Figure 31:
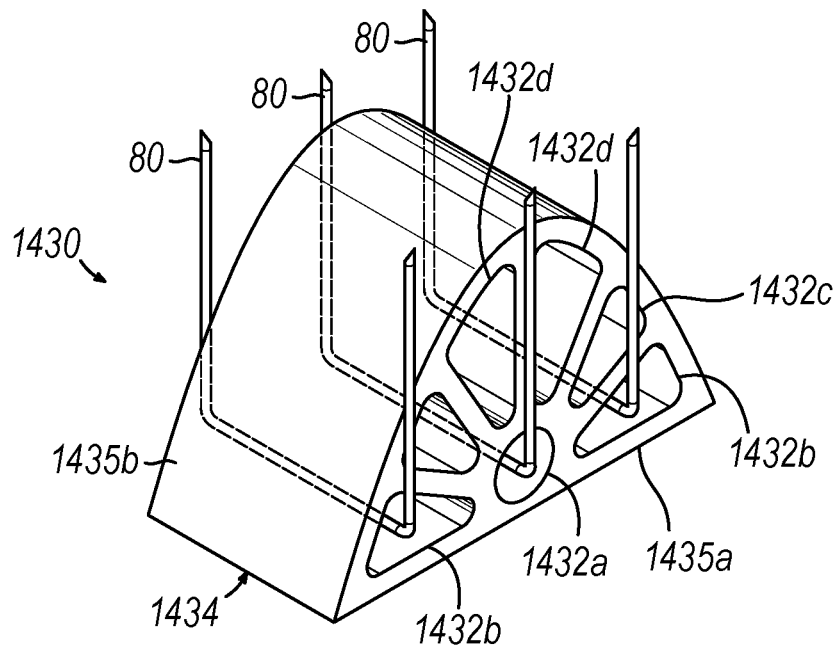
FIG. 31 depicts a partial top perspective view of another alternative exemplary adjunct that is extrudable and has a circular bore extending along a length thereof and a plurality of triangular bores extending along the length thereof, schematically showing the legs of staples deployed from a staple cartridge passing vertically through corresponding bores of the adjunct.

FIG. 31 shows another exemplary compressible unitary (e.g., monolithic) adjunct (1430) configured for releasable attachment to a staple cartridge (not shown) similar to staple cartridge (200). Adjunct (1430) is configured for use with end effector (50) and is similar to adjunct (1230) described above except as otherwise described below. In this regard, adjunct (1430) has an elongate body (1434) having a flat exterior bottom surface (1435a) and a generally C-shaped exterior top surface (1435b) such that the exterior of body (1434) has a generally D-shaped cross-sectional profile. Adjunct (1430) also has a plurality of axial bores (1432a, 1432b, 1432c, 1432d) extending in a proximal-distal direction along an entire length of body (1434). More particularly, adjunct (1430) has a single circular bore (1432a) and a plurality of triangular bores (1432b, 1432c, 1432d) extending radially between circular bore (1432a) and top surface (1435b). Adjunct (1430) may have a substantially uniform cross-sectional shape along a length thereof to enable extruding and/or drawing of adjunct (1430), in a manner similar to that described above in connection with FIG. 29.

As shown in FIG. 31, at least some bores (1432a, 1432b, 1432c, 1432d) of adjunct (1430) are configured to overlie a corresponding staple cartridge recess, similar to recesses (212, 214, 216), and/or a corresponding staple opening, similar to staple openings (208), of the staple cartridge to enable the legs of each staple (80) slidably housed within the respective staple opening to pass vertically through the corresponding bore(s) (1432a, 1432b, 1432c, 1432d) during deployment of staples (80), in a manner similar to that described above in connection with FIG. 29. It will also be appreciated that an upper portion of top surface (1435b) may engage and apply pressure to the stapled tissue to thereby assist with compressing the stapled tissue. In some versions, adjunct (1430) may be configured to provide a stress plateau when compressed for optimally compressing the stapled tissue over a predefined range of tissue thicknesses.

M. Fourth Exemplary Extrudable Adjunct

Figure 32:
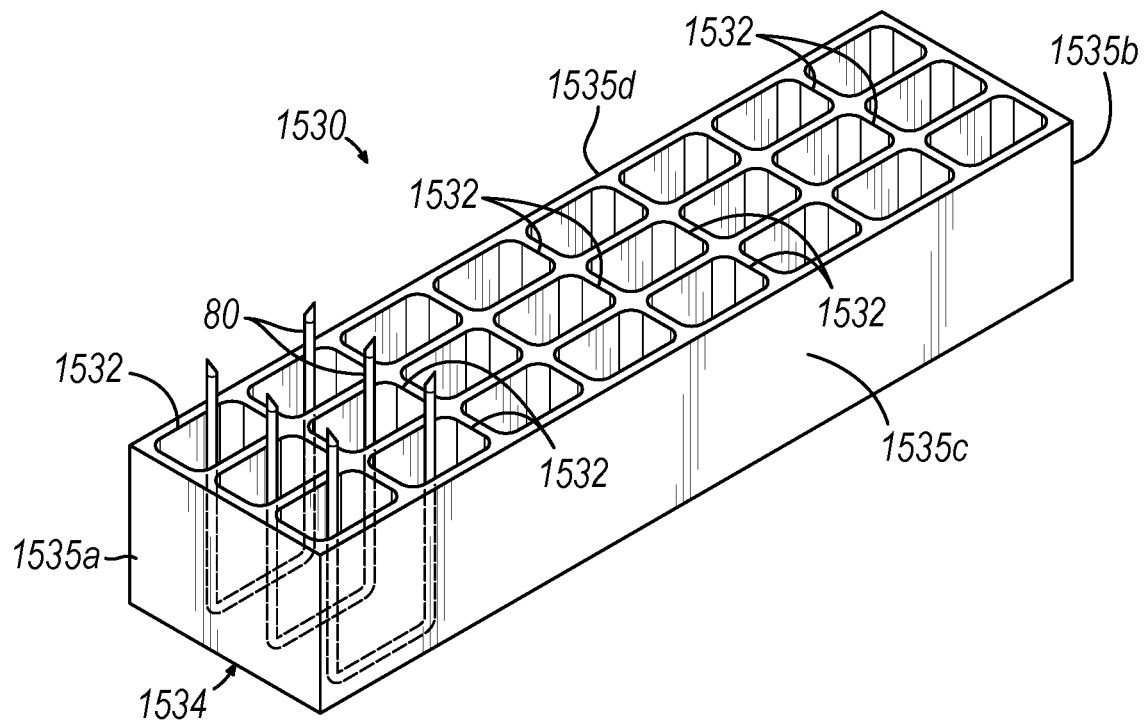
FIG. 32 depicts a top perspective view of another alternative exemplary adjunct that is extrudable and has a plurality of rectangular bores extending along a height thereof, schematically showing the legs of staples deployed from a staple cartridge passing vertically through corresponding bores of the adjunct.

FIG. 32 shows another exemplary compressible unitary (e.g., monolithic) adjunct (1530) configured for releasable attachment to a staple cartridge (not shown) similar to staple cartridge (200). Adjunct (1530) is configured for use with end effector (50) and is similar to adjunct (1230) described above except as otherwise described below. In this regard, adjunct (1530) has an elongate body (1534) having a pair of flat exterior longitudinal end surfaces (1535a, 1535b) and a pair of flat exterior side surfaces (1535c, 1535d) such that the exterior of body (1534) has a generally rectangular cross-sectional profile. Adjunct (1530) also has a plurality of vertical bores (1532) extending in a vertical direction along an entire height of body (1534). More particularly, adjunct (1530) has three axial rows of rectangular bores (1532) each extending in a proximal-distal direction, and eight transverse rows of rectangular bores (1532) each extending in a direction transverse to a length of the staple cartridge. Adjunct (1530) may have a substantially uniform cross-sectional shape along a height thereof to enable extruding and/or drawing of adjunct (1530), in a manner similar to that described above in connection with FIG. 29.

As shown in FIG. 32, each longitudinally-adjacent pair of rectangular bores (1532) of adjunct (1530) is configured to overlie the longitudinal ends of a corresponding staple cartridge recess, similar to recesses (212, 214, 216), and/or of a corresponding staple opening, similar to staple openings (208), of the staple cartridge to enable the leg of each staple (80) slidably housed within the respective staple opening to pass vertically through the corresponding rectangular bore (1532) during deployment of staples (80), in a manner similar to that described above in connection with FIG. 29. It will also be appreciated that at least an upper portion of body (1534) may engage and apply pressure to the stapled tissue to thereby assist with compressing the stapled tissue. In some versions, adjunct (1530) may be configured to provide a stress plateau when compressed for optimally compressing the stapled tissue over a predefined range of tissue thicknesses.

Figure 33:
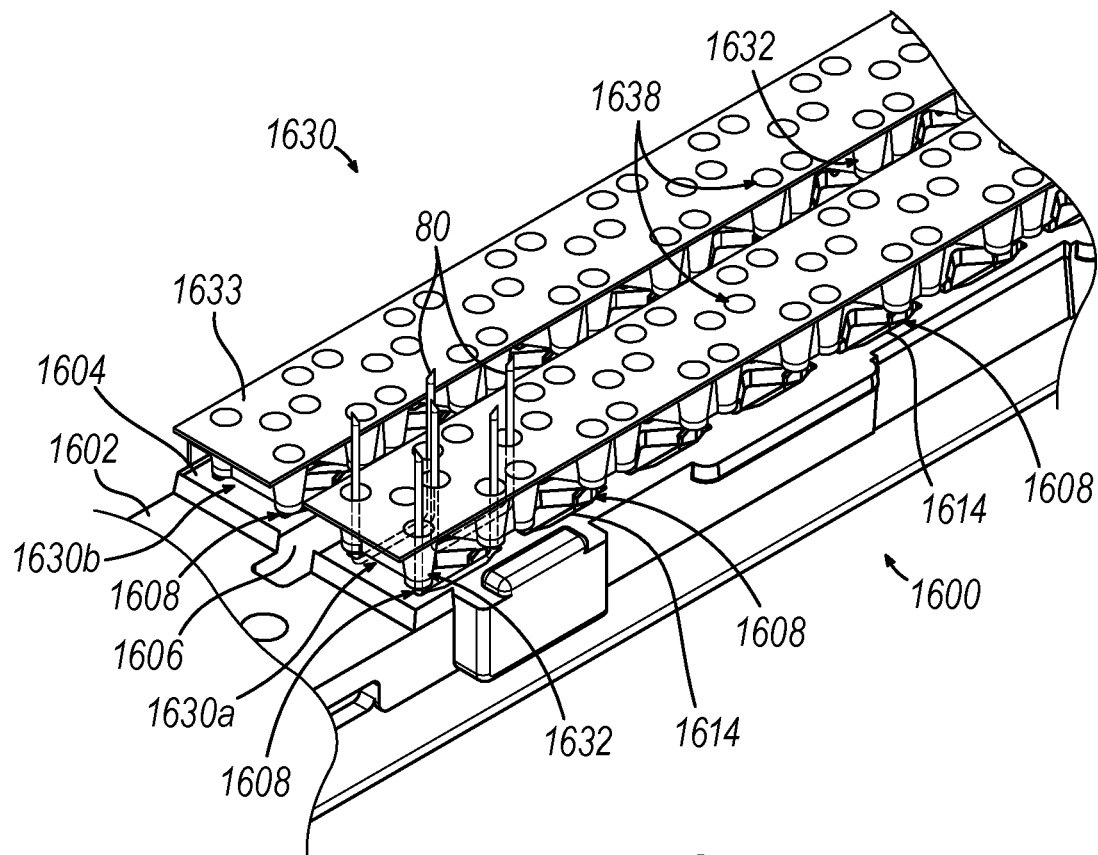
FIG. 33 depicts a partial top perspective view of another exemplary staple cartridge in combination with another alternative exemplary adjunct that is injection-moldable and has sleeve-shaped protrusions, schematically showing the legs of staples deployed from the staple cartridge received by corresponding sleeve-shaped protrusions of the adjunct.
Figure 34:
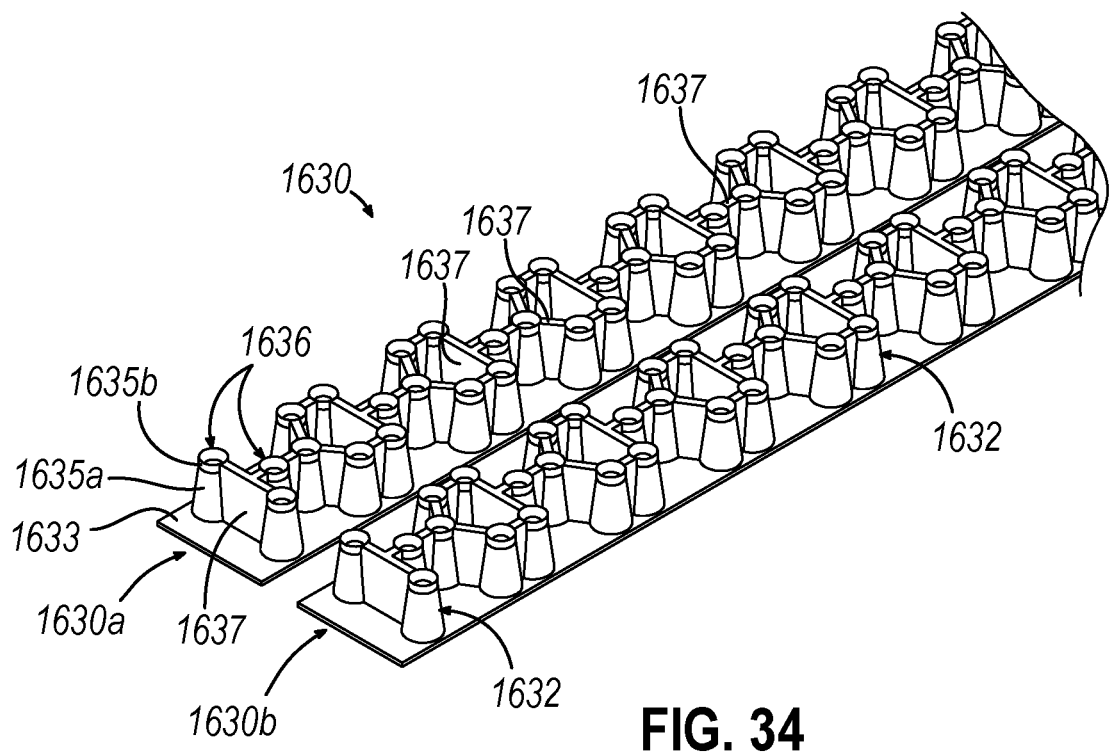
FIG. 34 depicts a partial bottom perspective view of the adjunct of FIG. 33.

N. Exemplary Injection-Moldable Adjunct with Sleeve-Shaped Protrusions Configured to Receive Staple Legs FIGS. 33-34 show another exemplary compressible unitary (e.g., monolithic) adjunct (1630) configured for releasable attachment to a staple cartridge (1600). Staple cartridge (1600) and adjunct (1630) are configured for use with end effector (50) and are similar to staple cartridge (200) and adjunct (230) described above except as otherwise described below. In this regard, staple cartridge (1600) includes a cartridge body (1602) having an upwardly facing deck (1604), an elongate slot (1606) extending along a central axis of cartridge body (1602) and opening upwardly through deck (1604), and a plurality of staple openings (1608) extending through deck (1604) on each side of elongate slot (1606). Each staple opening (1608) slidably houses an unformed staple (80), and a respective staple driver (not shown), similar to staple driver (82), configured to drive the corresponding staple outwardly toward anvil (56) to be formed. A lower tray (not shown) of staple cartridge (1600) retains the staples and the staple drivers within cartridge body (1602). Cartridge body (1602) of the present example further includes a plurality of upwardly-opening recesses (1614) formed in deck (1604) and having base surfaces through which staple openings (1608) extend.

Adjunct (1630) has a plurality of three-dimensional, resiliently compressible sleeve-shaped protrusions (1632) extending downwardly from a planar base in the form of a web (1633) having an elongate rectangular shape. In the present example, adjunct (1630) includes two lateral adjunct sections (1630a, 1630b) configured for placement on respective sides of staple cartridge slot (1606), each including inner and outer axial rows of sleeve-shaped protrusions (1632), and a medial axial row of sleeve-shaped protrusions (1632) extending in the proximal-distal direction and offset from each of the inner and outer axial rows of sleeve-shaped protrusions (1632) in the proximal-distal direction. Each sleeve-shaped protrusion (1632) of the present example has a hollow interior and includes a generally frustoconical upper sidewall (1635a) tapering inwardly toward a corresponding generally cylindrical lower sidewall (1635b) terminating at a respective open lower end (1636). Adjunct (1630) also includes a plurality of stiffening ribs (1637) extending between respective pairs of sleeve-shaped protrusions (1632). In some versions, walls (1635a, 1635b), ribs (1637), and/or web (1633) may have a substantially uniform thickness for supporting biocompatibility of adjunct (1630) by promoting uniform degrading of walls (1635a, 1635b), ribs (1637), and/or web (1633). As shown, each sleeve-shaped protrusion (1632) is interconnected with one, two, or three adjacent (e.g., laterally-adjacent and/or longitudinally-adjacent) sleeve-shaped protrusion(s) (1632), via ribs (1637).

The upper portions of the upper sidewalls (1635a) of each sleeve-shaped protrusion (1632) opposite the corresponding lower end (1636) intersect with web (1633) to collectively define an open upper end (1638) of the respective sleeve-shaped protrusion (1632). Upper ends (1638) of each sleeve-shaped protrusion (1632) are devoid of any undercuts or other geometrical features extending over the hollow interior of the respective sleeve-shaped protrusion (1632) such that each hollow interior opens uninterruptedly to the respective upper end (1638) to enable injection molding of adjunct (1630).

As shown in FIG. 33, each longitudinally-adjacent pair of sleeve-shaped protrusions (1632) of adjunct (1630) is configured to overlie the longitudinal ends of a corresponding staple cartridge recess (1614) and/or of a corresponding staple opening (1608), of staple cartridge (1600) to enable the leg of each staple (80) slidably housed within the respective staple opening (1608) to pass vertically through the corresponding sleeve-shaped protrusion (1632) during deployment of staples (80). In some versions, the lower end (1636) of each sleeve-shaped protrusion (1632) is configured to rest on deck (1604), and the tips of the legs of each staple (80) are configured to protrude upwardly out of the corresponding staple openings (1608) at least slightly above deck (1604) and into the hollow interior of the corresponding sleeve-shaped protrusion (1632) prior to deployment of staples (80) to assist with retaining adjunct (1630) on deck (1604) and/or to protect the tips of the legs of each staple (80) within the corresponding sleeve-shaped protrusion (1632). To that end, an adhesive material may be deposited within the hollow interior(s) of any one or more of sleeve-shaped protrusions (1632) to further secure adjunct (1630) to staples (80), which may themselves be retained within staple cartridge (1600), to thereby inhibit inadvertent dislodgement of adjunct (1630) from staple cartridge (1600).

In any event, such overlying of sleeve-shaped protrusions (1632) relative to the corresponding recesses (1614) may enable the deformed legs of each staple (80) to capture and compress the corresponding sleeve-shaped protrusion (1632) against the crown thereof when the staples are formed by staple forming pockets (58) of anvil (56). In this regard, sleeve-shaped protrusions (1632) may assist with the formation of staples (80) by guiding the tips of the legs of staples (80) toward respective target locations (e.g., within the corresponding staple forming pockets (58)) for achieving proper formation of staples (80). It will also be appreciated that the top surface of web (1633) may engage and apply pressure to the stapled tissue to thereby assist with compressing the stapled tissue. In some versions, adjunct (1630) may be configured to provide a stress plateau when compressed for optimally compressing the stapled tissue over a predefined range of tissue thicknesses. While adjunct (1630) is shown having sharp corners and edges, it will be appreciated that adjunct (1630) may be molded with smooth corners and edges that may be atraumatic to the tissue engaged thereby.

Figure 35:
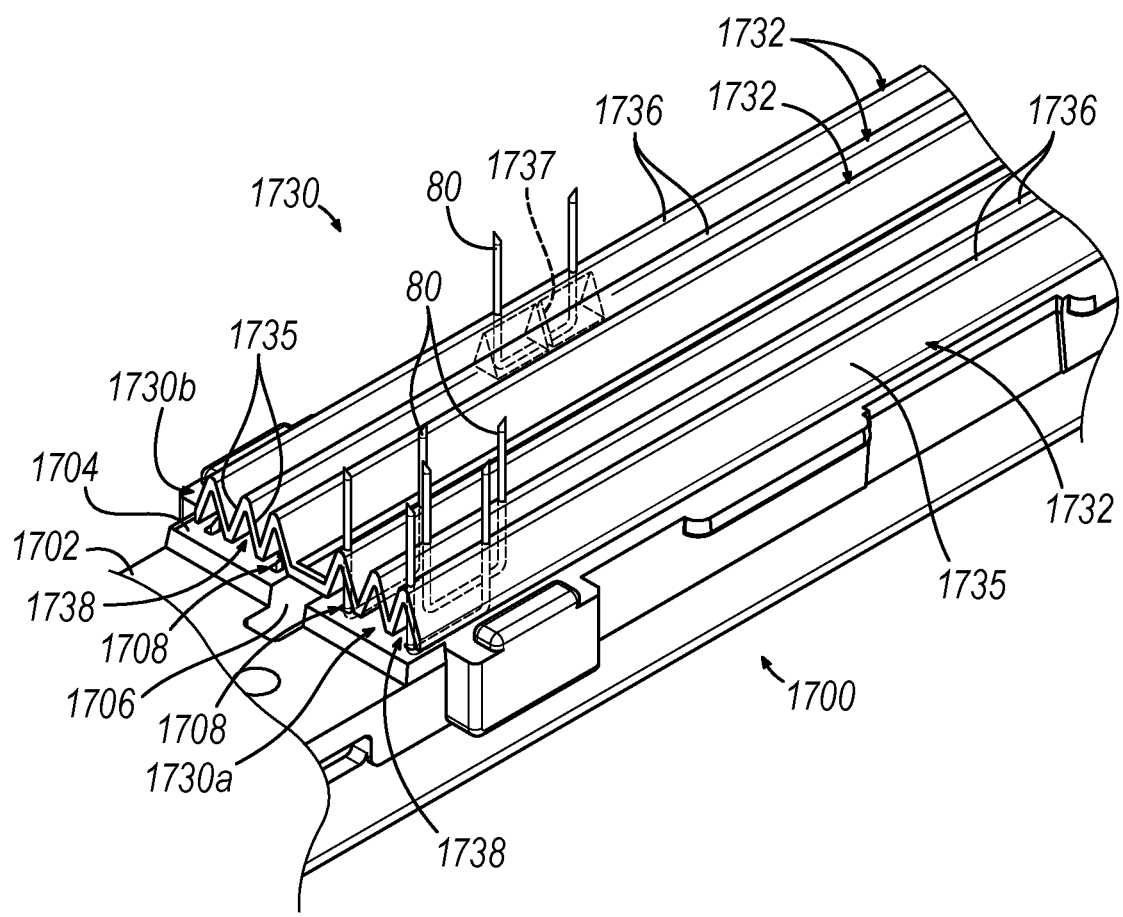
FIG. 35 depicts a partial top perspective view of another exemplary staple cartridge in combination with another alternative exemplary adjunct that is injection-moldable and has V-shaped corrugations, schematically showing the legs of staples deployed from the staple cartridge passing vertically through corresponding V-shaped corrugations of the adjunct.

O. Exemplary Injection-Moldable Adjunct with V-Shaped Corrugations Configured to Receive Staple Legs FIG. 35 shows another exemplary compressible unitary (e.g., monolithic) adjunct (1730) configured for releasable attachment to a staple cartridge (1700). Staple cartridge (1700) and adjunct (1730) are configured for use with end effector (50) and are similar to staple cartridge (200) and adjunct (230) described above except as otherwise described below. In this regard, staple cartridge (1700) includes a cartridge body (1702) having an upwardly facing deck (1704), an elongate slot (1706) extending along a central axis of cartridge body (1702) and opening upwardly through deck (1704), and a plurality of staple openings (1708) extending through deck (1704) on each side of elongate slot (1706). Each staple opening (1708) slidably houses an unformed staple (80), and a respective staple driver (not shown), similar to staple driver (82), configured to drive the corresponding staple outwardly toward anvil (56) to be formed. A lower tray (not shown) of staple cartridge (1700) retains the staples and the staple drivers within cartridge body (1702). Cartridge body (1702) of the present example further includes a plurality of upwardly-opening recesses (not shown), similar to recesses (212, 214, 216), formed in deck (1704) and having base surfaces through which staple openings (1708) extend.

Adjunct (1730) has a plurality of three-dimensional, resiliently compressible V-shaped corrugations (1732) defining a corrugated structure having an elongate rectangular shape. In the present example, adjunct (1730) includes two lateral adjunct sections (1730a, 1730b) configured for placement on respective sides of staple cartridge slot (1706), each including inner, outer, and medial V-shaped corrugations (1732) extending in the proximal-distal direction. Each V-shaped corrugation (1732) of the present example has a hollow interior and includes a pair of walls (1735) converging at a respective closed upper end (1736). In some versions, walls (1735) may have a substantially uniform thickness for supporting biocompatibility of adjunct (1730) by promoting uniform degrading of walls (1735). As shown, each medial V-shaped corrugation (1732) is interconnected with the laterally-adjacent inner and outer V-shaped corrugations (1732), via lower portions of the respective walls (1735) directly interfacing with each other. Adjunct (1730) also includes a plurality of lower stiffening ribs (1737) (one shown) extending between respective walls (1735) of each V-shaped corrugation (1732). In some versions, each medial V-shaped corrugation (1732) may also be interconnected with the laterally-adjacent inner and outer V-shaped corrugations (1732) via one or more upper stiffening ribs (not shown).

The lower portions of the walls (1735) of each V-shaped corrugation (1732) opposite the corresponding upper end (1736) collectively define an open lower end (1738) of the respective V-shaped corrugation (1732). Lower ends (1738) of each V-shaped corrugation (1732) are devoid of any undercuts or other geometrical features extending under the hollow interior of the respective V-shaped corrugation (1732) such that each hollow interior opens uninterruptedly to the respective lower end (1738) to enable injection molding and/or thermoforming of adjunct (1730).

As shown in FIG. 33, each V-shaped corrugation (1732) of adjunct (1730) is configured to overlie a corresponding axial row of staple cartridge recesses and/or of staple openings (1708) of staple cartridge (1700) to enable the leg of each staple (80) slidably housed within the respective staple opening (1708) to pass vertically through the corresponding V-shaped corrugation (1732) during deployment of staples (80). In some versions, the lower end (1738) of each V-shaped corrugation (1732) is configured to rest on deck (1704), and the tips of the legs of each staple (80) are configured to protrude upwardly out of the corresponding staple openings (1708) at least slightly above deck (1704) and into the hollow interior of the corresponding V-shaped corrugation (1732) prior to deployment of staples (80) to assist with retaining adjunct (1730) on deck (1604) and/or to protect the tips of the legs of each staple (80) within the corresponding V-shaped corrugation (1732). To that end, an adhesive material may be deposited within the hollow interior(s) of any one or more of V-shaped corrugations (1732) to further secure adjunct (1730) to staples (80), which may themselves be retained within staple cartridge (1700), to thereby inhibit inadvertent dislodgement of adjunct (1730) from staple cartridge (1700). In some versions, adjunct (1730) may include attachment features (not shown)

at or near an outer perimeter of adjunct (1730) for assisting with securing adjunct (1730) to staple cartridge (1700).

In any event, such overlying of V-shaped corrugations (1732) relative to the corresponding staple cartridge recesses may enable the deformed legs of each staple (80) to capture and compress the corresponding V-shaped corrugation (1732) and/or lower stiffening ribs (1737) against the crown thereof when the staples are formed by staple forming pockets (58) of anvil (56). In this regard, V-shaped corrugations (1732) may assist with the formation of staples (80) by guiding the tips of the legs of staples (80) toward respective target locations (e.g., within the corresponding staple forming pockets (58)) for achieving proper formation of staples (80). It will also be appreciated that upper ends (1736) of V-shaped corrugations (1732) may engage and apply pressure to the stapled tissue to thereby assist with compressing the stapled tissue. While not shown, adjunct (1730) may include a thin layer laminated onto the top (or bottom) of V-shaped corrugations (1732) for providing a smooth tissue-contacting surface. In some versions, adjunct (1730) may be configured to provide a stress plateau when compressed for optimally compressing the stapled tissue over a predefined range of tissue thicknesses. While adjunct (1730) is shown having sharp corners and edges, it will be appreciated that adjunct (1730) may be molded or thermoformed with smooth corners and edges that may be atraumatic to the tissue engaged thereby.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An adjunct configured for use with an end effector of a surgical stapler, comprising: (a) a plurality of resiliently compressible elements interconnected with each other; (b) a tissue-engaging face configured to contact tissue clamped by the end effector during closure thereof; and (c) a stapler-engaging face configured to be releasably secured to a stapling surface of the end effector, wherein each resiliently compressible element of the plurality of resiliently compressible elements includes a hollow interior and an open end at one of the tissue-engaging or stapler-engaging faces, wherein the hollow interior expands outwardly toward the open end, wherein each resiliently compressible element of the plurality of resiliently compressible elements is configured to be captured and compressed by a corresponding staple ejected from the end effector into the clamped tissue and thereby reinforce the engagement between the ejected staples and the clamped tissue.

Example 2

The adjunct of Example 1, wherein the resiliently compressible elements are integrally formed together with each other as a unitary piece.

Example 3

The adjunct of any one or more of Examples 1 through 2, wherein the plurality of resiliently compressible elements includes a plurality of resiliently compressible nodules.

Example 4

The adjunct of any one or more of Examples 1 through 2, further comprising a planar base, wherein the plurality of resiliently compressible elements includes a plurality of resiliently compressible protrusions extending from the planar base.

Example 5

The adjunct of any one or more of Examples 1 through 4, wherein the adjunct has a height, wherein each resiliently compressible element of the plurality of resiliently compressible elements includes at least wall having a thickness, wherein a ratio of the height to the thickness is between about 4:1 and about 8:1.

Example 6

The adjunct of any one or more of Examples 1 through 5, wherein each resiliently compressible element of the plurality of resiliently compressible elements includes a bioabsorbable polymeric material.

Example 7

The adjunct of any one or more of Examples 1 through 6, wherein the plurality of resiliently compressible elements collectively define an undulating cross-sectional profile of the adjunct.

Example 8

The adjunct of any one or more of Examples 1 through 7, wherein the hollow interior tapers outwardly toward the open end.

Example 9

The adjunct of any one or more of Examples 1 through 7, wherein the hollow interior curves outwardly toward the open end.

Example 10

The adjunct of any one or more of Examples 1 through 9, wherein the open end is devoid of undercuts.

Example 11

A surgical stapler, comprising: (a) an end effector including: (i) a first stapling surface, and (ii) a second stapling surface configured to cooperate with the first stapling surface to clamp and staple tissue; and (b) the adjunct of any one or more of Examples 1 through 10, wherein the stapler-engaging face of the adjunct is releasably secured to one of the first stapling surface or the second stapling surface.

Example 12

The surgical stapler of Example 11, wherein the end effector further includes a plurality of recesses formed in the one of the first stapling surface or the second stapling surface, wherein each resiliently compressible element of the plurality of resiliently compressible elements at least partially overlies at least one corresponding recess of the plurality of recesses.

Example 13

The surgical stapler of any one or more of Examples 11 through 12, wherein the end effector further includes a plurality of staple openings extending through the one of the first stapling surface or the second stapling surface, wherein each resiliently compressible element of the plurality of resiliently compressible elements at least partially overlies at least one corresponding staple opening of the plurality of staple openings.

Example 14

The surgical stapler of any one or more of Examples 11 through 13, further comprising a plurality of staples configured to be ejected from the one of the first stapling surface or the second stapling surface into the clamped tissue, wherein each staple of the plurality of staples includes a pair of legs, where each pair of legs is configured to flank a corresponding resiliently compressible element of the plurality of resiliently compressible elements during ejection of the respective staple from the one of the first stapling surface or the second stapling surface.

Example 15

The surgical stapler of Example 14, wherein each pair of legs is configured to be deformed by the other of the first stapling surface or the second stapling surface during ejection of the respective staple from the one of the first stapling surface or the second stapling surface to capture and compress the corresponding resiliently compressible element of the plurality of resiliently compressible elements.

Example 16

An adjunct configured for use with an end effector of a surgical stapler, comprising: (a) a stack of layers secured to each other, wherein each layer of the stack of layers includes a plurality of resiliently compressible elements; (b) a tissue-engaging face configured to contact tissue clamped by the end effector during closure thereof; and (c) a stapler-engaging face configured to be releasably secured to a stapling surface of the end effector, wherein each resiliently compressible element of the plurality of resiliently compressible elements is configured to be captured and compressed by a corresponding staple ejected from the end effector into the clamped tissue and thereby reinforce the engagement between the ejected staples and the clamped tissue.

Example 17

The adjunct of Example 16, wherein the plurality of resiliently compressible elements of each layer of the stack of layers collectively define a periodic undulating cross-sectional profile of the respective layer.

Example 18

The adjunct of any one or more of Examples 16 through 17, wherein the plurality of resiliently compressible elements have a substantially uniform height.

Example 19

The adjunct of any one or more of Examples 16 through 18, wherein the adjunct has a height of between about 1 mm and about 4 mm.

Example 20

An adjunct configured for use with an end effector of a surgical stapler, comprising: (a) a planar base; and (b) a plurality of resiliently compressible protrusions extending from the planar base, wherein each resiliently compressible protrusion of the plurality of resiliently compressible protrusions has a hollow interior, wherein each resiliently compressible protrusion of the plurality of resiliently compressible protrusions is configured to be captured and compressed by a corresponding staple ejected from the end effector into the clamped tissue and thereby reinforce the engagement between the ejected staples and the clamped tissue VI. Miscellaneous It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/704,075, filed Mar. 25, 2022, entitled "Tissue Cushion Adjuncts for Surgical Stapler End Effector," issued as U.S. Pat. No. 12,295,557 on May 13, 2025; U.S. patent application Ser. No. 17/704,082, filed Mar. 25, 2022, entitled "Thermally Formed Tissue Cushion Adjunct for Surgical Stapler End Effector," issued as U.S. Pat. No. 12,161,331 on Dec. 10, 2024; U.S. patent application Ser. No. 17/704,083, filed Mar. 25, 2022, entitled "Tissue Cushion Adjunct With Staple Leg Support Features for Surgical Stapler End Effector," issued as U.S. Pat. No. 12,082,834 on Sep. 10, 2024; and U.S. patent application Ser. No. 17/704,094, filed Mar. 25, 2022, entitled "Surgical Stapler Features for Stapling Variable Thickness Tissue," issued as U.S. Pat. No. 12,114,882 on Oct. 15, 2024. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An adjunct configured for use with an end effector of a surgical stapler, comprising:
   (a) a plurality of resiliently compressible protrusions interconnected with each other;
   (b) a tissue-engaging face configured to contact tissue clamped by the end effector during closure thereof; and
   (c) a stapler-engaging face configured to be releasably secured to a stapling surface of the end effector,
   wherein each resiliently compressible protrusion of the plurality of resiliently compressible protrusions includes a hollow interior and an open end at one of the tissue-engaging or stapler-engaging faces, wherein the hollow interior expands radially outwardly relative to a vertical central axis of the respective compressible protrusion toward the open end,
   wherein each resiliently compressible protrusion of the plurality of resiliently compressible protrusions is configured to be captured and compressed by a corresponding staple ejected from the end effector into the clamped tissue and thereby reinforce an engagement between the ejected staples and the clamped tissue.

2. The adjunct of claim 1, wherein the resiliently compressible protrusions are integrally formed together with each other as a unitary piece.

3. The adjunct of claim 1, wherein the plurality of resiliently compressible protrusions includes a plurality of resiliently compressible nodules.

4. The adjunct of claim 1, further comprising a planar base, wherein the plurality of resiliently compressible protrusions includes a plurality of resiliently compressible protrusions extending from the planar base.

5. The adjunct of claim 1, wherein the adjunct has a height, wherein each resiliently compressible protrusion of the plurality of resiliently compressible protrusions includes at least a wall having a thickness, wherein a ratio of the height to the thickness is between about 4:1 and about 8:1.

6. The adjunct of claim 1, wherein each resiliently compressible protrusion of the plurality of resiliently compressible protrusions includes a bioabsorbable polymeric material.

7. The adjunct of claim 1, wherein the plurality of resiliently compressible protrusions collectively define an undulating cross-sectional profile of the adjunct.

8. The adjunct of claim 1, wherein the hollow interior tapers outwardly toward the open end.

9. The adjunct of claim 1, wherein the hollow interior curves outwardly toward the open end.

10. The adjunct of claim 1, wherein the open end is devoid of undercuts.

11. A surgical stapler, comprising:
   (a) an end effector including:
      (i) a first stapling surface, and
      (ii) a second stapling surface configured to cooperate with the first stapling surface to clamp and staple tissue; and
   (b) the adjunct of claim 1, wherein the stapler-engaging face of the adjunct is releasably secured to one of the first stapling surface or the second stapling surface.

12. The surgical stapler of claim 11, wherein the end effector further includes a plurality of recesses formed in the one of the first stapling surface or the second stapling surface, wherein each resiliently compressible protrusion of the plurality of resiliently compressible protrusions at least partially overlies at least one corresponding recess of the plurality of recesses.

13. The surgical stapler of claim 11, wherein the end effector further includes a plurality of staple openings extending through the one of the first stapling surface or the second stapling surface, wherein each resiliently compressible protrusion of the plurality of resiliently compressible protrusions at least partially overlies at least one corresponding staple opening of the plurality of staple openings.

14. The surgical stapler of claim 11, further comprising a plurality of staples configured to be ejected from the one of the first stapling surface or the second stapling surface into the clamped tissue, wherein each staple of the plurality of staples includes a pair of legs, where each pair of legs is configured to flank a corresponding resiliently compressible protrusion of the plurality of resiliently compressible protrusions during ejection of the respective staple from the one of the first stapling surface or the second stapling surface.

15. The surgical stapler of claim 14, wherein each pair of legs is configured to be deformed by the other of the first stapling surface or the second stapling surface during ejection of the respective staple from the one of the first stapling surface or the second stapling surface to capture and compress the corresponding resiliently compressible protrusion of the plurality of resiliently compressible protrusions.

16. An adjunct configured for use with an end effector of a surgical stapler, comprising:
(a) a stack of layers secured to each other, wherein each layer of the stack of layers includes:
(i) a planar base, and
(ii) a plurality of resiliently compressible elements extending upwardly from the planar base;
(b) a tissue-engaging face configured to contact tissue clamped by the end effector during closure thereof; and
(c) a stapler-engaging face configured to be releasably secured to a stapling surface of the end effector,
wherein each resiliently compressible element of the plurality of resiliently compressible elements is configured to be captured and compressed by a corresponding staple ejected from the end effector into the clamped tissue and thereby reinforce an engagement between the ejected staples and the clamped tissue.

17. The adjunct of claim 16, wherein the plurality of resiliently compressible elements of each layer of the stack of layers collectively define a periodic undulating cross-sectional profile of the respective layer.

18. The adjunct of claim 16, wherein the plurality of resiliently compressible elements have a substantially uniform height.

19. The adjunct of claim 16, wherein the adjunct has a height of between about 1 mm and about 4 mm.

20. An adjunct configured for use with an end effector of a surgical stapler, comprising:
(a) a planar base; and
(b) a plurality of resiliently compressible X-shaped protrusions extending upwardly from the planar base to respective X-shaped upper ends, wherein each resiliently compressible X-shaped protrusion of the plurality of resiliently compressible X-shaped protrusions has a hollow interior,
wherein each resiliently compressible X-shaped protrusion of the plurality of resiliently compressible X-shaped protrusions is configured to be captured and compressed by a corresponding staple ejected from the end effector into the clamped tissue and thereby reinforce an engagement between the ejected staples and the clamped tissue.

* * * * *